(12) United States Patent
Huang et al.

(10) Patent No.: US 11,390,624 B2
(45) Date of Patent: Jul. 19, 2022

(54) PYRAZOLOPYRIDINES AND TRIAZOLOPYRIDINES AS A2A / A2B INHIBITORS

(71) Applicant: Incyte Corporation, Wilmington, DE (US)

(72) Inventors: Taisheng Huang, Wilmington, DE (US); Xiaozhao Wang, Mt. Laurel, NJ (US)

(73) Assignee: Incyte Corporation, Wilmington, DE (US)

( * ) Notice: Subject to any disclaimer, the term of this patent is extended or adjusted under 35 U.S.C. 154(b) by 89 days.

(21) Appl. No.: 16/774,086

(22) Filed: Jan. 28, 2020

(65) Prior Publication Data

US 2020/0270244 A1    Aug. 27, 2020

Related U.S. Application Data

(60) Provisional application No. 62/798,180, filed on Jan. 29, 2019.

(51) Int. Cl.
*C07D 471/04* (2006.01)

(52) U.S. Cl.
CPC .................................. *C07D 471/04* (2013.01)

(58) Field of Classification Search
CPC .................................................. C07D 471/04
USPC .................................................... 514/253.04
See application file for complete search history.

(56) References Cited

U.S. PATENT DOCUMENTS

| | | |
|---|---|---|
| 6,222,035 B1 | 4/2001 | Tsumuki et al. |
| 6,545,000 B1 | 4/2003 | Shimada et al. |
| 6,921,762 B2 | 7/2005 | Cai et al. |
| 7,041,666 B2 | 5/2006 | Matasi et al. |
| 7,306,631 B2 | 12/2007 | Glenn, Jr. et al. |
| 7,452,892 B2 | 11/2008 | Wu et al. |
| 7,501,411 B2 | 3/2009 | Andrews et al. |
| 7,511,050 B2 | 3/2009 | Zheng et al. |
| 7,563,788 B2 | 7/2009 | Sciotti et al. |
| 7,674,791 B2 | 3/2010 | Dowling et al. |
| 7,700,594 B2 | 4/2010 | Chen et al. |
| 7,709,468 B2 | 5/2010 | Calderwood et al. |
| 7,834,014 B2 | 11/2010 | Peng et al. |
| 8,053,574 B2 | 11/2011 | Bruce et al. |
| 8,133,895 B2 | 3/2012 | Andrews et al. |
| 8,202,869 B2 | 6/2012 | Kase et al. |
| 8,273,752 B2 | 9/2012 | Siegel et al. |
| 8,288,536 B2 | 10/2012 | Dong et al. |
| 8,349,850 B2 | 1/2013 | Tworowski et al. |
| 8,431,596 B2 | 4/2013 | Pave et al. |
| 8,569,300 B2 | 10/2013 | Borchardt et al. |
| 8,575,183 B2 | 11/2013 | Cushing et al. |
| 8,580,812 B2 | 11/2013 | Ihle et al. |
| 8,637,542 B2 | 1/2014 | Liu et al. |
| 8,865,731 B2 | 10/2014 | Ouchi et al. |
| 8,865,734 B2 | 10/2014 | No et al. |
| 9,029,389 B2 | 5/2015 | No et al. |
| 9,029,393 B2 | 5/2015 | Schann et al. |
| 9,034,872 B2 | 5/2015 | Tworowski et al. |
| 9,085,560 B2 | 7/2015 | Ren et al. |
| 9,127,000 B2 | 9/2015 | Ren et al. |
| 9,249,162 B2 | 2/2016 | Campbell et al. |
| 9,254,283 B2 | 2/2016 | Ikeda et al. |
| 9,328,121 B1 | 5/2016 | Takahashi et al. |
| 9,394,301 B2 | 7/2016 | Pave et al. |
| 9,394,311 B2 | 7/2016 | Flohr et al. |
| 9,573,948 B2 | 2/2017 | Cole et al. |
| 9,695,167 B2 | 7/2017 | Wu et al. |
| 9,944,647 B2 | 4/2018 | He et al. |
| 11,161,850 B2 | 11/2021 | Wang et al. |
| 11,168,089 B2 | 11/2021 | Want et al. |
| 2002/0193376 A1 | 12/2002 | Gall |
| 2003/0027820 A1 | 2/2003 | Gall |
| 2003/0143199 A1 | 7/2003 | Carson et al. |
| 2004/0186148 A1 | 9/2004 | Shankar et al. |

(Continued)

FOREIGN PATENT DOCUMENTS

| | | |
|---|---|---|
| AU | 2005260031 | 1/2006 |
| CN | 109535161 | 3/2019 |

(Continued)

OTHER PUBLICATIONS

International Preliminary Report on Patentability in International Application No. PCT/US2019/019582, dated Sep. 3, 2020, 11 pages.

International Preliminary Report on Patentability in International Application No. PCT/US2019/032948, dated Nov. 24, 2020, 9 pages.

Allard et al., "Immunosuppressive activities of adenosine in cancer," Curr Opin in Pharma., 2016, 29:7-16.

(Continued)

*Primary Examiner* — Taofiq A Solola
(74) *Attorney, Agent, or Firm* — Fish & Richardson P.C.

(57) ABSTRACT

This application relates to compounds of Formula (I):

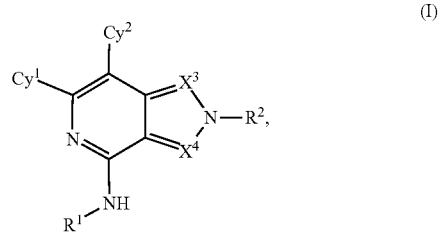

(I)

or pharmaceutically acceptable salts thereof, which modulate the activity of adenosine receptors, such as subtypes A2A and A2B receptors, and are useful in the treatment of diseases related to the activity of adenosine receptors including, for example, cancer, inflammatory diseases, cardiovascular diseases, and neurodegenerative diseases.

42 Claims, No Drawings

(56) References Cited

U.S. PATENT DOCUMENTS

| | | |
|---|---|---|
| 2005/0272765 A1 | 12/2005 | Feng et al. |
| 2005/0288502 A1 | 12/2005 | Anderson et al. |
| 2006/0040944 A1 | 2/2006 | Gosselin et al. |
| 2006/0058320 A1 | 3/2006 | Iida et al. |
| 2006/0154930 A1 | 7/2006 | Brown et al. |
| 2006/0178399 A1 | 8/2006 | Nishizawa et al. |
| 2006/0211739 A1 | 9/2006 | Perez-Medrano et al. |
| 2007/0010522 A1 | 1/2007 | Vu et al. |
| 2007/0117804 A1 | 5/2007 | Zhao et al. |
| 2007/0213332 A1 | 9/2007 | Burkamp et al. |
| 2007/0281942 A1 | 12/2007 | Cao et al. |
| 2008/0021026 A1 | 1/2008 | Kahraman |
| 2008/0021217 A1 | 1/2008 | Borchardt et al. |
| 2008/0096892 A1 | 4/2008 | Cheng et al. |
| 2008/0132501 A1 | 6/2008 | Sun et al. |
| 2008/0293739 A1 | 11/2008 | Trede |
| 2009/0105277 A1 | 4/2009 | Kadowaki et al. |
| 2009/0118301 A1 | 5/2009 | Lu et al. |
| 2009/0163489 A1 | 6/2009 | Booker et al. |
| 2009/0176778 A1 | 7/2009 | Schmitz et al. |
| 2009/0258877 A1 | 10/2009 | Siegel et al. |
| 2010/0105733 A1 | 4/2010 | Lyttle et al. |
| 2010/0160355 A1 | 6/2010 | Degoey et al. |
| 2010/0168138 A1 | 7/2010 | Degoey et al. |
| 2010/0261679 A1 | 10/2010 | Sutton et al. |
| 2010/0292232 A1 | 11/2010 | Elleder et al. |
| 2011/0105457 A1 | 5/2011 | Taniyama et al. |
| 2011/0190269 A1 | 8/2011 | Baumann et al. |
| 2011/0201649 A1 | 8/2011 | Matsuzaki et al. |
| 2011/0206607 A1 | 8/2011 | Olsson et al. |
| 2011/0288074 A1 | 11/2011 | Schann et al. |
| 2012/0021519 A1 | 1/2012 | Ichida et al. |
| 2012/0083498 A1 | 4/2012 | Kashanchi |
| 2012/0121540 A1 | 5/2012 | Schmitz et al. |
| 2012/0232089 A1 | 9/2012 | Kase et al. |
| 2013/0225568 A1 | 8/2013 | Burgdorf et al. |
| 2015/0197503 A1 | 7/2015 | Russo et al. |
| 2016/0009711 A1 | 1/2016 | Wu et al. |
| 2016/0046648 A1 | 2/2016 | Petrukhin et al. |
| 2016/0096835 A1 | 4/2016 | Cole et al. |
| 2016/0168154 A1 | 6/2016 | Marineau et al. |
| 2016/0354375 A1 | 12/2016 | Sheridan et al. |
| 2017/0114077 A1 | 4/2017 | Frideman et al. |
| 2018/0009816 A1 | 1/2018 | Bueskin et al. |
| 2018/0258043 A1 | 9/2018 | Gunzner-Toste et al. |
| 2019/0055250 A1 | 2/2019 | He et al. |
| 2019/0076433 A1 | 3/2019 | Willingham et al. |
| 2019/0092784 A1 | 3/2019 | Wu et al. |
| 2019/0292188 A1 | 9/2019 | Wang et al. |
| 2019/0375752 A1 | 12/2019 | Wang et al. |
| 2020/0031835 A1 | 1/2020 | Wang et al. |
| 2020/0102315 A1 | 4/2020 | Buesking et al. |
| 2021/0061809 A1 | 3/2021 | Han et al. |
| 2021/0139485 A1 | 5/2021 | Want et al. |
| 2021/0261555 A1 | 8/2021 | Wang et al. |

FOREIGN PATENT DOCUMENTS

| | | |
|---|---|---|
| DE | 102006041292 | 3/2008 |
| DE | 102011111400 | 2/2013 |
| EP | 0976753 | 2/2000 |
| EP | 1448564 | 8/2004 |
| EP | 1453835 | 9/2004 |
| EP | 1544200 | 6/2005 |
| EP | 1902716 | 3/2008 |
| EP | 1905418 | 4/2008 |
| EP | 2155747 | 2/2010 |
| JP | 2007039633 | 2/2007 |
| WO | WO 98/42711 | 10/1998 |
| WO | WO 2001/092264 | 12/2001 |
| WO | WO 2002/000196 | 1/2002 |
| WO | WO 2003/044021 | 5/2003 |
| WO | WO 2003/048164 | 6/2003 |
| WO | WO 2003/062236 | 7/2003 |
| WO | WO 2004/092173 | 10/2004 |
| WO | WO 2004/092177 | 10/2004 |
| WO | WO 2005/016892 | 2/2005 |
| WO | WO 2003/068776 | 6/2005 |
| WO | WO 2006/129626 | 12/2006 |
| WO | WO 2007/011759 | 1/2007 |
| WO | WO 2007/028051 | 3/2007 |
| WO | WO 2007/058942 | 5/2007 |
| WO | WO 2007/150025 | 12/2007 |
| WO | WO 2008/011560 | 1/2008 |
| WO | WO 2008/037607 | 4/2008 |
| WO | WO 2008/056176 | 5/2008 |
| WO | WO 2008/113469 | 9/2008 |
| WO | WO 2009/019505 | 2/2009 |
| WO | WO 2009/023179 | 2/2009 |
| WO | WO 2009/047514 | 4/2009 |
| WO | WO 2009/085185 | 7/2009 |
| WO | WO 2009/114870 | 9/2009 |
| WO | WO 2009/117421 | 9/2009 |
| WO | WO 2009/117734 | 9/2009 |
| WO | WO 2010/075074 | 7/2010 |
| WO | WO 2010/104306 | 9/2010 |
| WO | WO 2011/019780 | 2/2011 |
| WO | WO 2011/022439 | 2/2011 |
| WO | WO 2011/060207 | 5/2011 |
| WO | WO 2011/078143 | 6/2011 |
| WO | WO 2011/101409 | 8/2011 |
| WO | WO 2011/112766 | 9/2011 |
| WO | WO 2011/135303 | 11/2011 |
| WO | WO 2011/153588 | 12/2011 |
| WO | WO 2012/061156 | 5/2012 |
| WO | WO 2012/116237 | 8/2012 |
| WO | WO 2012/129344 | 9/2012 |
| WO | WO 2012/147890 | 11/2012 |
| WO | WO 2013/026516 | 2/2013 |
| WO | WO 2013/087943 | 6/2013 |
| WO | WO 2013/106254 | 7/2013 |
| WO | WO 2014/078479 | 5/2014 |
| WO | WO 2014/126580 | 8/2014 |
| WO | WO 2016/007722 | 1/2016 |
| WO | WO 2016/057522 | 4/2016 |
| WO | WO 2016/144703 | 9/2016 |
| WO | WO 2016/161282 | 10/2016 |
| WO | WO 2016/129684 | 11/2017 |
| WO | WO 2018/136265 | 7/2018 |
| WO | WO 2018/166493 | 9/2018 |
| WO | WO 2018/184590 | 10/2018 |
| WO | WO 2018/226976 | 12/2018 |
| WO | WO 2019/002606 | 1/2019 |
| WO | WO 2019/081353 | 5/2019 |
| WO | WO 2019/152678 | 8/2019 |
| WO | WO 2019/152687 | 8/2019 |
| WO | WO 2019/159120 | 8/2019 |
| WO | WO 2019/168847 | 9/2019 |
| WO | WO 2019/222677 | 11/2019 |
| WO | WO 2020/035424 | 2/2020 |
| WO | WO 2020/035425 | 2/2020 |
| WO | WO 2020/038983 | 2/2020 |
| WO | WO 2020/039051 | 2/2020 |
| WO | WO 2020/052631 | 3/2020 |
| WO | WO 2020/069027 | 4/2020 |
| WO | WO 2020/073945 | 4/2020 |
| WO | WO 2020/106560 | 5/2020 |
| WO | WO 2020/108613 | 6/2020 |

OTHER PUBLICATIONS

Antonioli et al., "Immunity, Inflammation and Cancer: a leading role for adenosine," Nature Reviews Cancer, Nov. 14, 2013, 13:842-857.

Baraldi et al., "Adenosine receptor antagonists: translating medicinal chemistry and pharmacology into clinical utility," Chem. Rev., Jan. 2008, 108(1):238-263.

Beavis et al., "Blockade of A2A receptors potently suppresses the metastasis of CD73+ tumors," Proc Natl Acad Sci. USA, Sep. 3, 2013, 110(36):14711-14716.

Beavis et al., "Targeting the adenosine 2A receptor enhances chimeric antigen receptor T cell efficacy," Journ. of Clin Invest., Mar. 2017, 127(3):929-941.

(56) References Cited

OTHER PUBLICATIONS

Berge et al., "Pharmaceutical Salts," Journal of Pharmaceutical Science, 1977, vol. 66, 21 pages.
Borrmann et al., "1-alkyl-8-(piperazine-1-sulfonyl)phenylxanthines: development and characterization of adenosine A2B receptor antagonists and a new radioligand with subnanomolar affinity and subtype specificity," J. Med. Chem., 2009, 52(13):3994-4006.
Carlsson et al., "Structure-based discovery of A2A adenosine receptor ligands," J. Med. Chem., 2010, 53(9):3748-3755.
Cekic et al., "Adenosine A2B receptor blockade slows growth of bladder and breast tumors," J Immunol, Jan. 1, 2012, 188(1):198-205.
Collins et al., "The novel adenosine A2A antagonist Lu AA47070 reverses the motor and motivational effects produced by dopamine D2 receptor blockade," Pharmacol. Biochem. Behav., Jan. 2012, 100(3):498-505.
Dowling et al., "Synthesis of [1,2,4]triazolo[1,5-a]pyrazines as adenosine A2A receptor antagonists," Bioorganic & Medicinal Chemistiy Letters., Nov. 1, 2005, 15(21):4809-4813.
Eisenstein et al., "The Many Faces of the A2b Adenosine Receptor in Cardiovascular and Metabolic Diseases," J Cell Physiol., Dec. 2015, 230(12):2891-2897.
Figler et al. "Links Between Insulin Resistance, Adenosine A2B Receptors, and Inflammatory Markers in Mice and Humans," Diabetes, Feb. 2011, 60(2):669-679.
Globenewswire.com [website], "Corvus Pharmaceuticals Announces Interim Results from Ongoing Phase 1/1b Study Demonstrating Safety and Clinical Activity of Lead Checkpoint Inhibitor CPI-444 in Patients with Advanced Cancers," Apr. 4, 2017, [retrieved on Apr. 4, 2019] retrieved from URL <https://globenewswire.com/news-release/2017/04/04/954192/0/en/Corvus-Pharmaceuticals-Announces-Interim-Results-from-Ongoing-Phase-1-1b-Study-Demonstrating-Safety-and-Clinical-Activity-of-Lead-Checkpoint-Inhibitor-CPI-444-in-Patients-with-Adva.html>, 7 pages.
Hasko et al., "Shaping of monocyte and macrophage function by adenosine receptors," Pharmacol. Ther., Feb. 2007, 113(2):264-275.
Iannone et al., "Adenosine limits the therapeutic effectiveness of anti-CTLA4 mAb in a mouse melanoma model," Am. J. Cancer Res. 2014, 4(2):172-181.
Iannone et al., "Blockade of A2b Adenosine Receptor Reduces Tumor Growth and Immune Suppression Mediated by Myeloid-Derived Suppressor Cells in a Mouse Model of Melanoma," Neoplasia, 2013, 15:1400-1410.
International Search Report and Written Opinion in International Application No. PCT/US2019/019582, dated Jul. 18, 2019, 19 pages.
International Search Report and Written Opinion in International Application No. PCT/US2019/032948, dated Aug. 8, 2019, 15 pages.
International Search Report and Written Opinion in International Application No. PCT/US2019/040496, dated Sep. 17, 2019, 17 pages.
Invitation to Pay Additional Fees in International Application No. PCT/US2019/019582, dated May 20, 2019, 9 pages.
Kerekes et al., "Aurora kinase inhibitors based on the imidazo[1,2-a]pyrazine core: fluorine and deuterium incorporation improve oral absorption and exposure," J. Med. Chem., Jan. 13, 2011, 54(1):201-210.
Leone et al., "A2aR antagonists: Next generation checkpoint blockade for cancer immunotherapy," Computational and Structural Biotechnology Journal, 2015, 13:365-272.
Livingston et al., "Adenosine, inflammation and asthma—a review," Inflamm. Res., May 2004, 53(5):171-178.
Matsumoto et al., "Alterations in vasoconstrictor responses to the endothelium-derived contracting factor uridine adenosine tetraphosphate are region specific in DOCA-salt hypertensive rats," Pharmacol. Res., Jan. 2012, 65(1):81-90.
Remington's Pharmaceutical Sciences, 17th ed., Mack Publishing Company, Easton, Pa., 1985, p. 1418.
Ryzhov et al., "Host A(2B) adenosine receptors promote carcinoma growth," Neoplasia, 2008, 10(9):987-995.
Sachdeva et al., "Adenosine and its receptors as therapeutic targets: An overview," Saudi Pharma Journ., Jun. 23, 2012, 21(3):245-253.
Sattin et al., "The effect of adenosine and adenine nucleotides on the cyclic adenosine 3', 5'-phosphate content of guinea pig cerebral cortex slices," Mol. Pharmacol., Jan. 1970, 6(1):13-23.
STN Search Report, 2017-078, dated Jul. 19, 2017, 73 pages.
STN Search Report, 2017-133, dated Nov. 22, 2017, 140 pages.
STN Search Report, 2018-080, dated Aug. 7, 2018, 399 pages.
Tamura et al., "A general synthesis of s-triazolo[1,5-x] diazines," J Hetero Chem., Feb. 1975, 12(1):107-110.
Tautenhahn et al. "Purinergic modulation of the excitatory synaptic input onto rat striatal neurons," Neuropharmacology, Mar. 2012, 62(4):4756-1766.
Yao et al., "Synthesis of alkyne derivatives of a novel triazolopyrazine as A2A adenosine receptor antagonists," Bioorganic & Medicinal Chemistry Letters, 2005, 15:511-515.
International Preliminary Report on Patentability in International Application No. PCT/US2020/015294, dated Jul. 27, 2021, 7 pages.
International Search Report and Written Opinion in International Application No. PCT/US2020/015294, dated May 6, 2020, 12 pages.
Ecuador Opposition in Ecuador Application No. SENADI-2020-60827, dated Apr. 27, 2021, 20 pages.
International Search Report and Written Opinion in International Application No. PCT/US2020/047714, dated Oct. 29, 2020, 15 pages.
International Preliminary Report on Patentability in International Application No. PCT/US2019/040496, dated Jan. 5, 2021, 9 pages.
Matasi et al., "2-(2-Furanyl)-7-phenyl[1,2,4]triazolo[1,5-c]pyrimidin-5-amine analogs: Highly potent, orally active, adenosine A2A antagonists. Part 1," Bioorganic & Medicinal Chemistry Letters, Aug. 15, 2005, 15(16):3670-3674.
Vietnamese Office Action in Vietnamese Application No. 1-2020-05531, dated Jan. 11, 2021, 2 pages.
Chilean Office Action in Chilean Application No. 2198-2020, dated Oct. 13, 2021, 24 pages.
Eurasian Office Action in Eurasian Application No. 202092016, dated Oct. 18, 2021, 7 pages.
Georgian Office Action in Georgian Application No. AP2019 15551, dated Dec. 2, 2021, 4 pages.
Georgian Office Action in Georgian Application No. AP 2019 15761, dated Jan. 11, 2022, 4 pages.

PYRAZOLOPYRIDINES AND TRIAZOLOPYRIDINES AS A2A / A2B INHIBITORS

TECHNICAL FIELD

The present invention provides fused heterocycles and derivatives thereof that modulate the activity of adenosine receptors, such as subtypes A2A and A2B, and are useful in the treatment of diseases related to the activity of adenosine receptors including, for example, cancer, inflammatory diseases, cardiovascular diseases and neurodegenerative diseases.

BACKGROUND

Adenosine is an extracellular signaling molecule that can modulate immune responses through many immune cell types. Adenosine was first recognized as a physiologic regulator of coronary vascular tone by Drury and Szent-Györgyu (Sachdeva, S. and Gupta, M. *Saudi Pharmaceutical Journal*, 2013, 21, 245-253), however it was not until 1970 that Sattin and Rall showed that adenosine regulates cell function via occupancy of specific receptors on the cell surface (Sattin, A., and Rall, T. W., 1970. Mol. Pharmacol. 6, 13-23; Hasko', G., at al., 2007, *Pharmacol. Ther.* 113, 264-275).

Adenosine plays a vital role in various other physiological functions. It is involved in the synthesis of nucleic acids and when linked to three phosphate groups, it forms ATP, the integral component of the cellular energy system. Adenosine can be generated by the enzymatic breakdown of extracellular ATP, or can also be released from injured neurons and glial cells by passing the damaged plasma membrane (Tautenhahn, M. et al. *Neuropharmacology*, 2012, 62, 1756-1766). Adenosine produces various pharmacological effects, both in the periphery and in the central nervous system (CNS), through an action on specific receptors localized on cell membranes (Matsumoto, T. et al. *Pharmacol. Res.*, 2012, 65, 81-90). Alternative pathways for extracellular adenosine generation have been described. These pathways include the production of adenosine from nicotinamide dinucleotide (NAD) instead of ATP by the concerted action of CD38, CD203a and CD73. CD73-independent production of adenosine can also occur by other phosphates such as alkaline phosphatase or prostate-specific phosphatase.

There are four known subtypes of adenosine receptor in humans including A1, A2A, A2B and A3 receptors. Al and A2A are high affinity receptors, whereas A2B and A3 are low affinity receptors. Adenosine and its agonists can act via one or more of these receptors and can modulate the activity of adenylate cyclase, the enzyme responsible for increasing cyclic AMP (cAMP). The different receptors have differential stimulatory and inhibitory effects on this enzyme. Increased intracellular concentrations of cAMP can suppress the activity of immune and inflammatory cells (Livingston, M. et al., *Inflamm. Res.*, 2004, 53, 171-178).

The A2A adenosine receptor can signal in the periphery and the CNS, with agonists explored as anti-inflammatory drugs and antagonists explored for neurodegenerative diseases (Carlsson, J. et al., *J. Med. Chem.*, 2010, 53, 3748-3755). In most cell types the A2A subtype inhibits intracellular calcium levels whereas the A2B potentiates them. The A2A receptor generally appears to inhibit inflammatory response from immune cells (Borrmann, T. et al., *J. Med. Chem.*, 2009, 52(13), 3994-4006).

A2B receptors are highly expressed in the gastrointestinal tract, bladder, lung and on mast cells (Antonioli, L. et al., *Nature Reviews Cancer*, 2013, 13, 842-857). The A2B receptor, although structurally closely related to the A2A receptor and able to activate adenylate cyclase, is functionally different. It has been postulated that this subtype may utilize signal transduction systems other than adenylate cyclase (Livingston, M. et al., *Inflamm. Res.*, 2004, 53, 171-178). Among all the adenosine receptors, the A2B adenosine receptor is a low affinity receptor that is thought to remain silent under physiological conditions and to be activated in consequence of increased extracellular adenosine levels (Ryzhov, S. et al. *Neoplasia*, 2008, 10, 987-995). Activation of A2B adenosine receptor can stimulate adenylate cyclase and phospholipase C through activation of Gs and Gq proteins, respectively. Coupling to mitogen activated protein kinases has also been described (Boiiniann, T. et al., *J. Med. Chem.*, 2009, 52(13), 3994-4006).

In the immune system, engagement of adenosine signaling can be a critical regulatory mechanism that protects tissues against excessive immune reactions. Adenosine can negatively modulate immune responses through many immune cell types, including T-cells, natural-killer cells, macrophages, dendritic cells, mast cells and myeloid-derived suppressor cells (Allard, B. et al. *Current Opinion in Pharmacology*, 2016, 29, 7-16).

In tumors, this pathway is hijacked by tumor microenvironments and sabotages the antitumor capacity of immune system, promoting cancer progression. In the tumor micro-environment, adenosine was mainly generated from extracellular ATP by CD39 and CD73. Multiple cell types can generate adenosine by expressing CD39 and CD73. This is the case for tumor cells, T-effector cells, T-regulatory cells, tumor associated macrophages, myeloid derived suppressive cells (MDSCs), endothelial cells, cancer-associated fibroblast (CAFs) and mesenchymal stromal/stem cells (MSCs). Hypoxia, inflammation and other immune-suppressive signaling in tumor micro-environment can induce expression of CD39, CD73 and subsequent adenosine production. As a result, adenosine level in solid tumors is unusually high compared to normal physiological conditions.

A2A are mostly expressed on lymphoid-derived cells, including T-effector cells, T regulatory cells and nature killing cells. Blocking A2A receptor can prevent downstream immunosuppressive signals that temporarily inactivate T cells. A2B receptors are mainly expressed on monocyte-derived cells including dendritic cells, tumor-associated macrophages, myeloid derived suppressive cells (MDSCs), and mesenchymal stromal/stem cells (MSCs). Blocking A2B receptor in preclinical models can suppress tumor growth, block metastasis, and increase the presentation of tumor antigens.

In terms of safety profile of ADORA2A/ADORA2B (A2A/A2B) blockage, the A2A and A2B receptor knockout (KO) mice are all viable, showing no growth abnormalities and are fertile (Allard, B. et al. *Current Opinion in Pharmacology*, 2016, 29, 7-16). A2A KO mice displayed increased levels of pro-inflammatory cytokines only upon challenge with LPS and no evidence of inflammation at baseline (Antonioli, L. et al., *Nature Reviews Cancer*, 2013, 13, 842-857). A2B KO mice exhibited normal platelet, red blood, and white cell counts but increased inflammation at baseline (TNF-alpha, IL-6) in naive A2B KO mice (Antonioli, L. et al., *Nature Reviews Cancer*, 2013, 13, 842-857). Exaggerated production of TNF-alpha and IL-6 was detected following LPS treatment. A2B KO mice also exhibited increased vascular adhesion molecules that mediate inflammation as well leukocyte adhesion/rolling; enhanced mast-cell activation; increased sensitivity to IgE-mediated anaphylaxis and increased vascular leakage and neutrophil influx under hypoxia (Antonioli, L. et al., *Nature Reviews Cancer*, 2013, 13, 842-857).

In summary, there is a need to develop new adenosine receptor selective ligands, such as for subtypes A2A and A2B, for the treatment of diseases such as cancer, inflammatory diseases, cardiovascular diseases and neurodegenerative diseases. This application is directed to this need and others.

SUMMARY

The present invention relates to, inter alia, compounds of Formula (I):

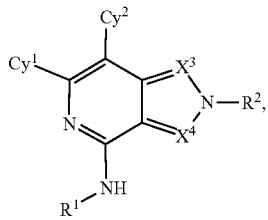

or pharmaceutically acceptable salts thereof, wherein constituent members are defined herein.

The present invention further provides pharmaceutical compositions comprising a compound of Formula (I), or a pharmaceutically acceptable salt thereof, and a pharmaceutically acceptable carrier.

The present invention further provides methods of inhibiting an activity of an adenosine receptor, comprising contacting the receptor with a compound of Formula (I), or a pharmaceutically acceptable salt thereof.

The present invention further provides methods of treating a disease or a disorder associated with abnormal expression of adenosine receptors, comprising administering to said patient a therapeutically effective amount of a compound of Formula (I), or a pharmaceutically acceptable salt thereof.

The present invention further provides a compound of Formula (I), or a pharmaceutically acceptable salt thereof, for use in any of the methods described herein.

The present invention further provides use of a compound of Formula (I), or a pharmaceutically acceptable salt thereof, for the preparation of a medicament for use in any of the methods described herein.

DETAILED DESCRIPTION

Compounds

The present application provides, inter alia, a compound of Formula (I):

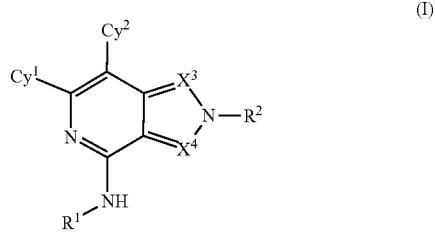

or a pharmaceutically acceptable salt thereof, wherein:

$X^3$ is N or $CR^3$;

$X^4$ is N or $CR^4$;

$Cy^1$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $Cy^1$ are each optionally substituted with 1, 2, 3, 4, 5, or 6 independently selected $R^5$ substituents;

$Cy^2$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $Cy^2$ are each optionally substituted with 1, 2, 3, 4, 5, or 6 independently selected $R^6$ substituents;

$R^1$ is selected from H, $C_{1-6}$ alkyl, $C_{2-6}$ alkenyl, $C_{2-6}$ alkynyl, $C_{1-6}$ haloalkyl, $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, and $S(O)_2NR^{c1}R^{d1}$, wherein the $C_{1-6}$ alkyl, $C_{2-6}$ alkenyl, and $C_{2-6}$ alkynyl of $R^1$ are each optionally substituted with 1, 2, 3, or 4 independently selected $R^{14}$ substituents;

each $R^{a1}$, $R^{b1}$, $R^{c1}$, and $R^{d1}$ is independently selected from H, $C_{1-6}$ alkyl, $C_{2-6}$ alkenyl, $C_{2-6}$ alkynyl, and $C_{1-6}$ haloalkyl, wherein the $C_{1-6}$ alkyl, $C_{2-6}$ alkenyl, and $C_{2-6}$ alkynyl of $R^{a1}$, $R^{b1}$, $R^{c1}$, and $R^{d1}$ are each optionally substituted with 1, 2, 3, or 4 independently selected $R^{14}$ substituents;

each $R^{e1}$ is independently selected from H, OH, CN, $C_{1-6}$ alkyl, $C_{2-6}$ alkenyl, $C_{2-6}$ alkynyl, $C_{1-6}$ alkoxy, $C_{1-6}$ haloalkyl, and $C_{1-6}$ haloalkoxy;

each $R^{14}$ is independently selected from OH, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino;

$R^2$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b2}$, $C(O)NR^{c2}R^{d2}$, $C(O)OR^{a2}$, $C(=NR^{e2})R^{b2}$, $C(=NR^{e2})NR^{c2}R^{d2}$, $S(O)_2R^{b2}$, and $S(O)_2NR^{c2}R^{d2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, or 6 independently selected $R^{24}$ substituents;

each $R^{a2}$, $R^{b2}$, $R^{c2}$, and $R^{d2}$ is independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{b2}$, $R^{c2}$, and $R^{d2}$, are each optionally substituted with 1, 2, 3, 4, 5, or 6 independently selected $R^{2A}$ substituents;

or, any $R^{c2}$ and $R^{d2}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NR^{e21})NR^{c21}R^{d21}$, $NR^{c21}C(=NR^{e21})NR^{c21}R^{d21}$, $NR^{c21}C(=NR^{e21})R^{b21}$, $NR^{c21}S(O)NR^{c21}R^{d21}$, $NR^{c21}S(O)R^{b21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $OS(O)(=NR^{e21})R^{b21}$, $OS(O)_2R^{b21}$, $SF_5$, $P(O)R^{f21}R^{g21}$, $OP(O)(OR^{h21})(OR^{i21})$, $P(O)(OR^{h21})(OR^{i21})$, and $BR^{j21}R^{k21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, 4, 5, or 6 independently selected $R^{2B}$ substituents;

each $R^{a21}$, $R^{b21}$, $R^{c21}$ and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl- of $R^{a21}$, $R^{b21}$, $R^{c21}$ and $R^{d21}$ are each optionally substituted with 1, 2, 3, 4, 5, or 6 independently selected $R^{2B}$ substituents;

or, any $R^{c21}$ and $R^{d21}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{2B}$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f21}$ and $R^{g21}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h21}$ and $R^{i21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j21}$ and $R^{k21}$ is independently selected from OH, $C_{1-6}$ alkoxy, and $C_{1-6}$ haloalkoxy;

or any $R^{j21}$ and $R^{k21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $SR^{a22}$, $NHOR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}NR^{c22}R^{d22}$, $NR^{c22}C(O)R^{b22}$, $NR^{c22}C(O)OR^{a22}$, $NR^{c22}C(O)NR^{c22}R^{d22}$, $C(=NR^{e22})R^{b22}$, $C(=NR^{e22})NR^{c22}R^{d22}$, $NR^{c22}C(=NR^{e22})NR^{c22}R^{d22}$, $NR^{c22}C(=NR^{e22})R^{b22}$, $NR^{c22}S(O)NR^{c22}R^{d22}$, $NR^{c22}S(O)R^{b22}$, $NR^{c22}S(O)_2R^{b22}$, $NR^{c22}S(O)(=NR^{e22})R^{b22}$, $NR^{c22}S(O)_2NR^{c22}R^{d22}$, $S(O)R^{b22}$, $S(O)NR^{c22}R^{d22}$, $S(O)_2R^{b22}$, $S(O)_2NR^{c22}R^{d22}$, $OS(O)(=NR^{c22})R^{b22}$, $OS(O)_2R^{b22}$, $SF_5$, $P(O)R^{f22}R^{g22}$, $OP(O)(OR^{h22})(OR^{i22})$, $P(O)(OR^{h22})(OR^{i22})$, and $BR^{j22}R^{k22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, or 4 independently selected $R^{2C}$ substituents;

each $R^{a22}$, $R^{b22}$, $R^{c22}$ and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{b22}$, $R^{c22}$ and $R^{d22}$ are each optionally substituted with 1, 2, 3, or 4 independently selected $R^{2C}$ substituents;

or, any $R^{c22}$ and $R^{d22}$, attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{2C}$ substituents;

each $R^{e22}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f22}$ and $R^{g22}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h22}$ and $R^{i22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j22}$ and $R^{k22}$ is independently selected from OH, $C_{1-6}$ alkoxy, and $C_{1-6}$ haloalkoxy;

or any $R^{j22}$ and $R^{k22}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2C}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a23}$, $SR^{a23}$, $NHOR^{a23}$, $C(O)R^{b23}$, $C(O)NR^{c23}R^{d23}$, $C(O)NR^{c23}(OR^{a23})$, $C(O)OR^{a23}$, $OC(O)R^{b23}$, $OC(O)NR^{c23}R^{d23}$, $NR^{c23}R^{d23}$, $NR^{c23}NR^{c23}R^{d23}$, $NR^{c23}C(O)R^{b23}$, $NR^{c23}C(O)OR^{a23}$, $NR^{c23}C(O)NR^{c23}R^{d23}$, $C(=NR^{e23})R^{b23}$, $C(=NR^{e23})NR^{c23}R^{d23}$, $NR^{c23}C(=NR^{e23})NR^{c23}R^{d23}$, $NR^{c23}C(=NR^{e23})R^{b23}$, $NR^{c23}S(O)NR^{c23}R^{d23}$, $NR^{c23}S(O)R^{b23}$, $NR^{c23}S(O)_2R^{b23}$, $NR^{c23}S(O)(=NR^{e23})R^{b23}$, $NR^{c23}S(O)_2NR^{c23}R^{d23}$, $S(O)R^{b23}$, $S(O)NR^{c23}R^{d23}$, $S(O)_2R^{b23}$, $S(O)_2NR^{c23}R^{d23}$, $OS(O)(=NR^{e23})R^{b23}$, $OS(O)_2R^{b23}$, $SF_5$, $P(O)R^{f23}R^{g23}$, $OP(O)(OR^{h23})(OR^{i23})$, $P(O)(OR^{h23})(OR^{i23})$, and $BR^{j23}R^{k23}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2C}$ are each optionally substituted with 1, 2, 3, or 4 independently selected $R^{2D}$ substituents;

each $R^{a23}$, $R^{b23}$, $R^{c23}$, and $R^{d23}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-, $C_{1-6}$ alkyl-, and (4-10 membered heterocycloalkyl)-$C_{1-6}$ alkyl- of $R^{a23}$, $R^{b23}$, $R^{c23}$ and $R^{d23}$ are each optionally substituted with 1, 2, 3, or 4 independently selected $R^{2D}$ substituents;

or, any $R^{c23}$ and $R^{d23}$, attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{2D}$ substituents;

each $R^{e23}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f23}$ and $R^{g23}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h23}$ and $R^{i23}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j23}$ and $R^{k23}$ is independently selected from OH, $C_{1-6}$ alkoxy, and $C_{1-6}$ haloalkoxy;

or any $R^{j23}$ and $R^{k23}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2D}$ is independently selected from D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a24}$, $SR^{a24}$, $NHOR^{a24}$, $C(O)R^{b24}$, $C(O)NR^{c24}R^{d24}$, $C(O)NR^{c24}(OR^{a24})$, $C(O)OR^{a24}$, $OC(O)R^{b24}$, $OC(O)NR^{c24}R^{d24}$, $NR^{c24}R^{d24}$, $NR^{c24}NR^{c24}R^{d24}$, $NR^{c24}C(O)R^{b24}$, $NR^{c24}C(O)OR^{a24}$, $NR^{c24}C(O)NR^{c24}R^{d24}$, $C(=NR^{e24})R^{b24}$, $C(=NR^{e24})NR^{c24}R^{d24}$, $NR^{c24}C(=NR^{e24})NR^{c24}R^{d24}$, $NR^{c24}C(=NR^{e24})R^{b24}$, $NR^{c24}S(O)NR^{c24}R^{d24}$, $NR^{c24}S(O)R^{b24}$, $NR^{c24}S(O)_2R^{b24}$, $NR^{c24}S(O)(=NR^{e24})R^{b24}$, $NR^{c24}S(O)_2NR^{c24}R^{d24}$, $S(O)R^{b24}$, $S(O)NR^{c24}R^{d24}$, $S(O)_2R^{b24}$, $S(O)_2NR^{c24}R^{d24}$, $OS(O)(=NR^{e24})R^{b24}$, $OS(O)_2R^{b24}$, $SF_5$, $P(O)R^{f24}R^{g24}$, $OP(O)(OR^{h24})(OR^{i24})$, $P(O)(OR^{h24})(OR^{i24})$, and $BR^{j24}R^{k24}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{2D}$ are each optionally substituted with 1, 2, 3, or 4 independently selected $R^{2E}$ substituents;

each $R^{a24}$, $R^{b24}$, $R^{c24}$ and $R^{d24}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a24}$, $R^{b24}$, $R^{c24}$ and $R^{d24}$ are each optionally substituted with 1, 2, 3, or 4 independently selected $R^{2E}$ substituents;

or, any $R^{c24}$ and $R^{d24}$, attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{2E}$ substituents;

each $R^{e24}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f24}$ and $R^{g24}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h24}$ and $R^{i24}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j24}$ and $R^{k24}$ is independently selected from OH, $C_{1-6}$ alkoxy, and $C_{1-6}$ haloalkoxy;

or any $R^{j24}$ and $R^{k24}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2E}$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^3$ is selected from H, D, halo, OH, CN, $NO_2$, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-3}$ alkyl, HO—$C_{1-3}$ alkyl, $C_{1-3}$ alkoxy-$C_{1-3}$ alkyl, $C_{3-5}$ cycloalkyl, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl) carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^4$ is selected from H, D, halo, OH, CN, $NO_2$, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-3}$ alkyl, HO—$C_{1-3}$ alkyl, $C_{1-3}$ alkoxy-$C_{1-3}$ alkyl, $C_{3-5}$ cycloalkyl, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl) carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each $R^5$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(C)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)(=NR^{e5})R^{b5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, 4, 5, or 6 independently selected $R^{5A}$ substituents;

each $R^{a5}$, $R^{b5}$, $RC^{c5}$ and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{b5}$, $R^{c5}$ and $R^{d5}$ are each optionally substituted with 1, 2, 3, 4, 5, or 6 independently selected $R^{5A}$ substituents;

or, any $R^{c5}$ and $R^{d5}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{5A}$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f5}$ and $R^{g5}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5A}$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^6$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a6}$, SR$^{a6}$, NHOR$^{a6}$, C(O)R$^{b6}$, C(O)NR$^{c6}$R$^{d6}$, C(O)NR$^{c6}$(OR$^{a6}$), C(O)OR$^{a6}$, OC(O)R$^{b6}$, OC(O)NR$^{c6}$R$^{d6}$, NR$^{c6}$R$^{d6}$, NR$^{c6}$NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, C(=NR$^{e6}$)R$^{b6}$, C(=NR$^{e6}$)NR$^{c6}$R$^{d6}$, NR$^{c6}$C(=NR$^{e6}$)NR$^{c6}$R$^{d6}$, NR$^{c6}$C(=NR$^{e6}$)R$^{b6}$, NR$^{c6}$S(O)NR$^{c6}$R$^{d6}$, NR$^{c6}$S(O)R$^{b6}$, NR$^{c6}$S(O)$_2$R$^{b6}$, NR$^{c6}$S(O)(=NR$^{e6}$)R$^{b6}$, NR$^{c6}$S(O)NR$^{c6}$R$^{d6}$, S(O)R$^{b6}$, S(O)NR$^{c6}$R$^{d6}$, S(O)$_2$R$^{b6}$, S(O)$_2$NR$^{c6}$R$^{d6}$, OS(O)(=NR$^{e6}$)R$^{b6}$, OS(O)$_2$R$^{b6}$, SF$_6$, P(O)R$^{f6}$R$^{g6}$, OP(O)(OR$^{h6}$)(OR$^{i6}$), P(O)(OR$^{h6}$)(OR$^{i6}$), and BR$^{j6}$R$^{k6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, or 6 independently selected $R^{6A}$ substituents;

or, two $R^6$ groups together form an oxo group;

each $R^{a6}$, $R^{b6}$, $R^{c6}$ and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{b6}$, $R^{c6}$ and $R^{d6}$ are each optionally substituted with 1, 2, 3, 4, 5, or 6 independently selected $R^{6A}$ substituents;

or, any $R^{c6}$ and $R^{d6}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{6A}$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^{6A}$ is independently selected from OH, NO$_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^3$ is N and $X^4$ is N.

In some embodiments, $X^3$ is CR$^3$ and $X^4$ is N.

In some embodiments, $X^3$ is N and $X^4$ is CR$^4$.

In some embodiments, $R^3$ is selected from H and $C_{1-6}$ alkyl.

In some embodiments, $R^3$ is selected from H and methyl.

In some embodiments, $R^3$ is H.

In some embodiments, $R^4$ is selected from H and $C_{1-6}$ alkyl.

In some embodiments, $R^4$ is selected from H and methyl.

In some embodiments, $R^4$ is H.

In some embodiments, $Cy^1$ is $C_{6-10}$ aryl or 5-10 membered heteroaryl, wherein the $C_{6-10}$ aryl and 5-10 membered heteroaryl are each optionally substituted with 1, 2, 3, or 4 independently selected $R^5$ substituents.

In some embodiments, $Cy^1$ is phenyl optionally substituted with 1, 2, 3, or 4 independently selected $R^5$ substituents; and each $R^5$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a5}$, SR$^{a5}$, NHOR$^{a5}$, C(O)R$^{b5}$, C(O)NR$^{c5}$R$^{d5}$, C(O)NR$^{c5}$(OR$^{a5}$), C(O)OR$^{a5}$, OC(O)R$^{b5}$, OC(O)NR$^{c5}$R$^{d5}$, NR$^{c5}$R$^{d5}$, NR$^{c5}$NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$C(=NR$^{e5}$)R$^{b5}$, NR$^{c5}$S(C)NR$^{c5}$R$^{d5}$, NR$^{c5}$S(O)R$^{b5}$, NR$^{c5}$S(O)$_2$R$^{b5}$, NR$^{c5}$S(O)(=NR$^{e5}$)R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, S(O)$_2$NR$^{c5}$R$^{d5}$, OS(O)(=NR$^{e5}$)R$^{b5}$, and OS(O)$_2$R$^{b5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents.

In some embodiments, $Cy^1$ is phenyl optionally substituted with 1 or 2 independently selected $R^5$ substituents; and each $R^5$ is independently selected from halo, $C_{1-6}$ alkyl, $C_{1-6}$ haloalkyl, CN, and NO$_2$.

In some embodiments, $Cy^1$ is cyanophenyl optionally substituted with fluoro.

In some embodiments, $Cy^1$ is cyanophenyl.

In some embodiments, $Cy^1$ is 3-benzonitrile.

In some embodiment, $Cy^1$ is 3-(2-fluorobenzonitrile).

In some embodiments, $Cy^2$ is 5-10 membered heteroaryl or 4-10 membered heterocycloalkyl, wherein the 5-10 membered heteroaryl and 4-10 membered heterocycloalkyl are each optionally substituted with 1, 2, 3, or 4 independently selected $R^6$ substituents.

In some embodiments, $Cy^2$ is 5-10 membered heteroaryl or 4-10 membered heterocycloalkyl, wherein the 5-10 membered heteroaryl and 4-10 membered heterocycloalkyl are each optionally substituted with 1, 2, 3, or 4 independently selected $R^6$ substituents; and each $R^6$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)NR^{c6}R^{d6}$, $NR^{c6}S(O)R^{b6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, and $OS(O)_2R^{b6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{6A}$ substituents, or, two $R^6$ groups together form an oxo group.

In some embodiments, $Cy^2$ is 5-10 membered heteroaryl or 4-10 membered heterocycloalkyl, wherein the 5-10 membered heteroaryl and 4-10 membered heterocycloalkyl are each optionally substituted with 1, 2, or 3 independently selected $R^6$ substituents; and each $R^6$ is independently selected from halo, $C_{1-6}$ alkyl, and $C_{1-6}$ haloalkyl, wherein the $C_{1-6}$ alkyl is optionally substituted with OH, or, two $R^6$ groups together form an oxo group.

In some embodiments, $Cy^2$ is selected from pyrimidinyl, pyrazolyl, pyridinyl, dihydropyridinyl, oxazolyl, quinolinyl, and quionaxalinyl, wherein the pyrimidinyl, pyrazolyl, pyridinyl, dihydropyridinyl, oxazolyl, quinolinyl, and quionaxalinyl are each optionally substituted with 1, 2, or 3 independently selected $R^6$ substituents; and each $R^6$ is independently selected from halo, $C_{1-6}$ alkyl, and $C_{1-6}$ haloalkyl, wherein the $C_{1-6}$ alkyl is optionally substituted with OH, or, two $R^6$ groups together form an oxo group.

In some embodiments, $Cy^2$ is selected from pyrimidin-4-yl, 1-ethyl-1H-pyrazol-5-yl, pyridin-4-yl, 1-isopropyl-1H-pyrazol-5-yl, 1-methyl-1H-pyrazol-5-yl, 1-methyl-6-oxo-1,6-dihydropyridin-3-yl, 3-methylpyridin-4-yl, 4-(hydroxymethyl)-2-methyloxazol-5-yl, 4-methyloxazol-5-yl, oxazol-5-yl, quinolin-6-yl, and quinoxalin-6-yl.

In some embodiments, $R^1$ is selected from H, $C_{1-6}$ alkyl, $C_{2-6}$ alkenyl, $C_{2-6}$ alkynyl, and $C_{1-6}$ haloalkyl.

In some embodiments, $R^1$ is H.

In some embodiments, $R^2$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- are each optionally substituted with 1, 2, 3, or 4 independently selected $R^{2A}$ substituents.

In some embodiments, $R^2$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- are each optionally substituted with 1, 2, 3, or 4 independently selected $R^{2A}$ substituents; and each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $S(O)R^{b21}$ $S(O)NR^{c21}R^{d21}$, and $S(O)_2R^{b21}$.

In some embodiments, $R^2$ is phenyl-$C_{1-3}$ alkyl- or (5-10 membered heteroaryl)-$C_{1-3}$ alkyl-, wherein the phenyl-$C_{1-3}$ alkyl- and (5-10 membered heteroaryl)-$C_{1-3}$ alkyl- are each optionally substituted with 1, 2, 3, or 4 independently selected $R^{2A}$ substituents; and each $R^{2A}$ is independently selected from from halo, $C_{1-6}$ alkyl, and $C_{1-6}$ haloalkyl.

In some embodiments, $R^2$ is selected from benzyl, pyridinylmethyl, pyrazolylmethyl, and pyridinylethyl, wherein benzyl, pyridinylmethyl, pyrazolylmethyl, and pyridinylethyl are each optionally substituted with 1, 2, 3, or 4 independently selected $R^{2A}$ substituents; and each $R^{2A}$ is independently selected from from halo, $C_{1-6}$ alkyl, and $C_{1-6}$ haloalkyl.

In some embodiments, $R^2$ is selected from pyridin-2-ylmethyl, (1-methyl-1H-pyrazol-3-yl)methyl, (3-fluoropyridin-2-yl)methyl, (6-methylpyridin-2-yl)methyl, 1-(pyridin-2-yl)ethyl, 2-(pyridin-2-yl)ethyl, and 2-fluorobenzyl.

In some embodiments, the compound of Formula (I), or a pharmaceutically acceptable salt thereof, is a compound of Formula (II):

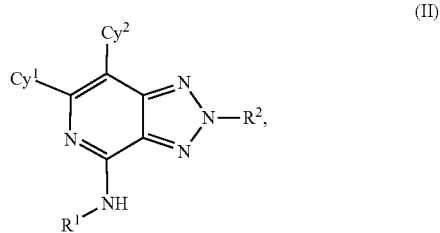

or a pharmaceutically acceptable salt thereof, wherein variables $R^1$, $R^2$, $Cy^1$ and $Cy^2$ are defined according to the definitions provided herein, such as for compounds of Formula (I).

In some embodiments, the compound of Formula (I) or Formula (II), or a pharmaceutically acceptable salt thereof, is a compound of Formula (IIa):

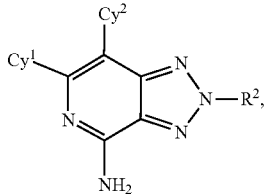

(IIa)

or a pharmaceutically acceptable salt thereof, wherein variables $R^2$, $Cy^1$ and $Cy^2$ are defined according to the definitions provided herein, such as for compounds of Formula (I).

In some embodiments, the compound of Formula (I) or Formula (II), or a pharmaceutically acceptable salt thereof, is a compound of Formula (IIb):

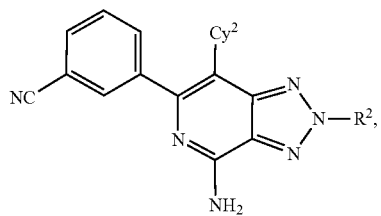

(IIb)

or a pharmaceutically acceptable salt thereof, wherein variables $R^2$ and $Cy^2$ are defined according to the definitions provided herein, such as for compounds of Formula (I).

In some embodiments, the compound of Formula (I), or a pharmaceutically acceptable salt thereof, is a compound of Formula (III):

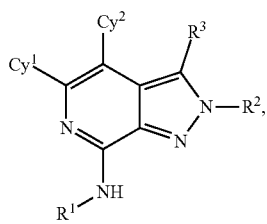

(III)

or a pharmaceutically acceptable salt thereof, wherein variables $R^1$, $R^2$, $R^3$, $Cy^1$ and $Cy^2$ are defined according to the definitions provided herein, such as for compounds of Formula (I).

In some embodiments, the compound of Formula (I) or Formula (III), or a pharmaceutically acceptable salt thereof, is a compound of Formula (IIIa):

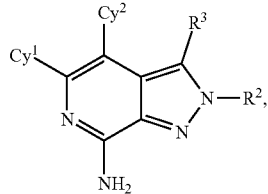

(IIIa)

or a pharmaceutically acceptable salt thereof, wherein variables $R^2$, $R^3$, $Cy^1$ and $Cy^2$ are defined according to the definitions provided herein, such as for compounds of Formula (I).

In some embodiments, the compound of Formula (I) or Formula (III), or a pharmaceutically acceptable salt thereof, is a compound of Formula (IIIb):

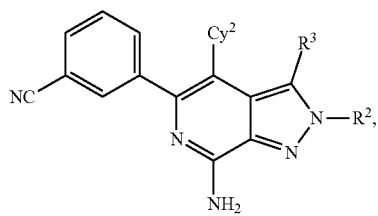

(IIIb)

or a pharmaceutically acceptable salt thereof, wherein variables $R^2$, $R^3$ and $Cy^2$ are defined according to the definitions provided herein, such as for compounds of Formula (I).

In some embodiments, the compound of Formula (I) or a pharmaceutically acceptable salt thereof, is a compound of Formula (IV):

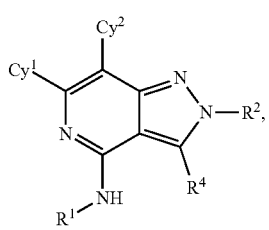

(IV)

or a pharmaceutically acceptable salt thereof, wherein variables $R^1$, $R^2$, $R^4$, $Cy^1$ and $Cy^2$ are defined according to the definitions provided herein, such as for compounds of Formula (I).

In some embodiments, the compound of Formula (I) or Formula (IV), or a pharmaceutically acceptable salt thereof, is a compound of Formula (IVa):

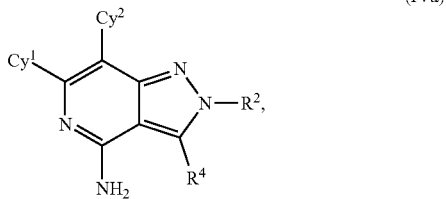

or a pharmaceutically acceptable salt thereof, wherein variables $R^2$, $R^4$, $Cy^1$ and $Cy^2$ are defined according to the definitions provided herein, such as for compounds of Formula (I).

In some embodiments, the compound of Formula (I) or Formula (IV), or a pharmaceutically acceptable salt thereof, is a compound of Formula (IVb):

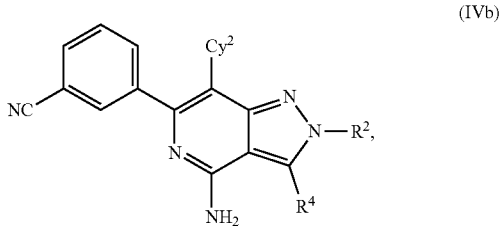

or a pharmaceutically acceptable salt thereof, wherein variables $R^2$, $R^4$, and $Cy^2$ are
defined according to the definitions provided herein, such as for compounds of Formula (I).

In some embodiments, the compound of Formula (I) or a pharmaceutically acceptable salt thereof, is a compound of Formula (V):

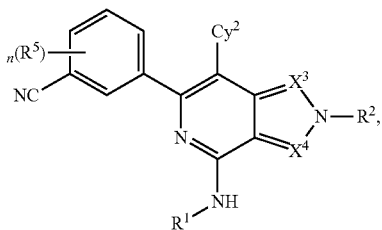

or a pharmaceutically acceptable salt thereof,
wherein n is 0, 1, or 2; and
variables $X^3$, $X^4$, $R^1$, $R^2$, $R^5$, and $Cy^2$ are defined according to the definitions provided herein, such as for compounds of Formula (I).

In some embodiments of the compound of Formula (I), or a pharmaceutically acceptable salt thereof,
$X^3$ is N or $CR^3$;
$X^4$ is N or $CR^4$;
$Cy^1$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $Cy^1$ are each optionally substituted with 1, 2, 3, or 4 independently selected $R^5$ substituents;
$Cy^2$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $Cy^2$ are each optionally substituted with 1, 2, 3, or 4 independently selected $R^6$ substituents;
$R^1$ is selected from H and $C_{1-6}$ alkyl;
$R^2$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;
each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{d21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $S(O)R^{b21}$, $S(O)NR^{c21}R^{d21}$, and $S(O)_2R^{b21}$;
each $R^{a21}$, $R^{b21}$, $R^{c21}$ and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;
or, any $R^{c21}$ and $R^{d21}$, attached to the same N atom, together with the N atom to which they are attached, form a 4-10 membered heterocycloalkyl group;
$R^3$ is selected from H, D, halo, OH, CN, $NO_2$, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-3}$ alkyl, HO—$C_{1-3}$ alkyl, $C_{1-3}$ alkoxy-$C_{1-3}$ alkyl, $C_{3-5}$ cycloalkyl, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;
$R^4$ is selected from H, D, halo, OH, CN, $NO_2$, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-3}$ alkyl, HO—$C_{1-3}$ alkyl, $C_{1-3}$ alkoxy-$C_{1-3}$ alkyl, $C_{3-5}$ cycloalkyl, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each $R^5$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(C)NR^{c5}(OR^{a5})$, $C(O)OR^{a5}$, $OC(O)R^{b5}$, $OC(O)NR^{c5}R^{d5}$, $NR^{c5}R^{d5}$, $S(O)R^{b5}$, $S(O)NR^{c5}R^{d5}$, and $S(O)_2R^{b5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents;

each $R^{a5}$, $R^{b5}$, $R^{c5}$ and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{b5}$, $R^{c5}$ and $R^{d5}$ are each optionally substituted with 1, 2, 3, or 4 independently selected $R^{5A}$ substituents;

or, any $R^{c5}$ and $R^{d5}$, attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{5A}$ substituents;

each $R^{5A}$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^6$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $S(O)R^{b6}$, $S(O)NR^{c6}R^{d6}$, and $S(O)_2R^{b6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{6A}$ substituents, or, two $R^6$ groups together form an oxo group;

each $R^{a6}$, $R^{b6}$, $R^{c6}$ and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl- of $R^{a6}$, $R^{b6}$, $R^{c6}$ and $R^{d6}$ are each optionally substituted with 1, 2, 3, or 4 independently selected $R^{6A}$ substituents;

or, any $R^{c6}$ and $R^{d6}$, attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{6A}$ substituents; and each $R^{6A}$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments of the compound of Formula (I), or a pharmaceutically acceptable salt thereof, $X^3$ is N or $CR^3$;

$X^4$ is N or $CR^4$;

wherein at least one of $X^3$ and $X^4$ is N;

$Cy^1$ is $C_{6-10}$ aryl optionally substituted with 1, 2, 3, or 4 independently selected $R^5$ substituents;

$Cy^2$ is selected from 5-10 membered heteroaryl and 4-10 membered heterocycloalkyl, wherein the 5-10 membered heteroaryl and 4-10 membered heterocycloalkyl of $Cy^2$ are each optionally substituted with 1, 2, 3, or 4 independently selected $R^6$ substituents;

$R^1$ is selected from H and $C_{1-6}$ alkyl;

$R^2$ is selected from $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, and $OR^{a21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

$R^{a21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl;

each $R^{2B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, and $OR^{a22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, or 4 independently selected $R^{2C}$ substituents;

$R^{a22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl;

each $R^{2C}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, and $OR^{a23}$ $R^{a23}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl.

$R^3$ is selected from H and $C_{1-6}$ alkyl;

$R^4$ is selected from H and $C_{1-6}$ alkyl;

each $R^5$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^5$, and $NR^{c5}R^{d5}$;

each $R^{a5}$, $R^{c5}$ and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

or, any $R^{c5}$ and $R^{d5}$, attached to the same N atom, together with the N atom to which they are attached, form a 4-10 membered heterocycloalkyl group;

each $R^6$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, and $NR^{c6}R^{d6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^{6A}$ substituents, or, two $R^6$ groups together form an oxo group;

each $R^{a6}$, $R^{c6}$ and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

or, any $R^{c6}$ and $R^{d6}$, attached to the same N atom, together with the N atom to which they are attached, form a 4-10 membered heterocycloalkyl group; and each $R^{6A}$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-6}$ cycloalkyl, $C_{1-6}$ alkoxy, $C_{1-6}$ haloalkoxy, amino, and $C_{1-6}$ alkylamino.

In some embodiments of the compound of Formula (I), or a pharmaceutically acceptable salt thereof, $X^3$ is N or CH;

$X^4$ is N or CH;

wherein at least one of $X^3$ and $X^4$ is N;

$Cy^1$ is phenyl substituted with 1 or 2 independently selected $R^5$ substituents;

$Cy^2$ is selected from pyrimidin-4-yl, 1-ethyl-1H-pyrazol-5-yl, pyridin-4-yl, 1-isopropyl-1H-pyrazol-5-yl, 1-methyl-1H-pyrazol-5-yl, 1-methyl-6-oxo-1,6-dihydropyridin-3-yl, 3-methylpyridin-4-yl, 4-(hydroxymethyl)-2-methyloxazol-5-yl, 4-methyloxazol-5-yl, oxazol-5-yl, quinolin-6-yl, and quinoxalin-6-yl;

$R^1$ is H;

$R^2$ is selected from pyridin-2-ylmethyl, (1-methyl-1H-pyrazol-3-yl)methyl, (3-fluoropyridin-2-yl)methyl, (6-methylpyridin-2-yl)methyl, 1-(pyridin-2-yl)ethyl, 2-(pyridin-2-yl)ethyl, and 2-fluorobenzyl; and each $R^5$ is independently selected from F and CN.

In some embodiments, the compound is the (S)-enantiomer of one of the preceding compounds, or a pharmaceutically acceptable salt thereof. In some embodiments, the compound is the (R)-enantiomer of one of the preceding compounds, or a pharmaceutically acceptable salt thereof.

In some embodiments, 1, 2, 3, 4, 5, 6, 7, or 8 hydrogen atoms, attached to carbon atoms of any "alkyl", "alkenyl", "alkynyl", "aryl", "phenyl", "cycloalkyl", "heterocycloalkyl", or "heteroaryl" substituents or "-$C_{1-6}$ alkyl-", "alkylene", "alkenylene", and "alkynylene" linking groups, are each optionally replaced by a deuterium atom.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both—NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the term "C." indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —$NH_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 5 to 10 carbon atoms. In some embodiments, the aryl group is phenyl or naphthyl. In some embodiments, the aryl is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "$C_{n-m}$ haloalkoxy" refers to a group of formula —O-haloalkyl having n to m carbon atoms. Example haloalkoxy groups include $OCF_3$ and $OCHF_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include $CF_3$, $C_2F_5$, $CHF_2$, $CH_2F$, $CCl_3$, $CHCl_2$, $C_2Cl_5$ and the like.

As used herein, the term "thio" refers to a group of formula —SH.

As used herein, the term "carbamyl" to a group of formula —$C(O)NH_2$.

As used herein, the term "carbonyl", employed alone or in combination with other terms, refers to a —C(O)— group.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{m-n}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{m-n}$ alkylsulfonylamino" refers to a group of formula —$NHS(O)_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —$S(O)_2NH_2$.

As used herein, the term "$C_{n-m}$ alkylaminosulfonyl" refers to a group of formula —$S(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —$S(O)_2N$(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —$NHS(O)_2NH_2$.

As used herein, the term "$C_{n-m}$ alkylaminosulfonylamino" refers to a group of formula —$NHS(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —$NHS(O)_2N$(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —$NHC(O)NH_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{m-n}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "cyano-$C_{1-n}$ alkyl" refers to a group of formula —($C_{1-n}$ alkylene)-CN, wherein the alkyl group has 1 to n carbon atoms. In some embodiments, the alkyl group has 1 to 6, 1 to 4, or 1 to 3 carbon atoms, e.g., —($C_{1-3}$ alkylene)-CN.

As used herein, the term "HO—$C_{1-n}$ alkyl" refers to a group of formula —($C_{1-n}$ alkylene)-OH, wherein the alkyl group has 1 to n carbon atoms. In some embodiments, the alkyl group has 1 to 6, 1 to 4, or 1 to 3 carbon atoms, e.g., —($C_{1-3}$ alkylene)-OH.

As used herein, the term "$C_{1-n}$ alkoxy-$C_{1-n}$ alkyl" refers to a group of formula —($C_{1-n}$ alkylene)-O($C_{1-n}$ alkyl), wherein the alkyl group has 1 to n carbon atoms. In some embodiments, the alkyl group has 1 to 6, 1 to 4, or 1 to 3 carbon atoms, e.g., —($C_{1-6}$ alkylene)-O($C_{1-6}$alkyl).

As used herein, the term "carboxy" refers to a group of formula —C(O)OH.

As used herein, the term "di($C_{n-m}$ alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$ alkyl)carbamyl" refers to a group of formula C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkylcarbonyloxy" is a group of formula —OC(O)-alkyl, wherein the alkyl group has n to m carbon atoms.

As used herein, "aminocarbonyloxy" is a group of formula —OC(O)—NH$_2$.

As used herein, "$C_{n-m}$ alkylaminocarbonyloxy" is a group of formula —OC(O)—NH-alkyl, wherein the alkyl group has n to m carbon atoms.

As used herein, "di($C_{m-n}$ alkyl)aminocarbonyloxy" is a group of formula —OC(O)—N(alkyl)$_2$, wherein each alkyl group has, independently, n to m carbon atoms.

As used herein "$C_{n-m}$ alkoxycarbonylamino" refers to a group of formula —NHC(O)O($C_{n-m}$ alkyl), wherein the alkyl group has n to m carbon atoms.

As used herein, "cycloalkyl" refers to non-aromatic cyclic hydrocarbons including cyclized alkyl and alkenyl groups. Cycloalkyl groups can include mono- or polycyclic (e.g., having 2 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (i.e., $C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2 fused rings) aromatic heterocycle having at least one heteroatom ring member selected from N, O, S and B. In some embodiments, the heteroaryl ring has 1, 2, 3, or 4 heteroatom ring members independently selected from N, O, S, and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, S, and B. In some embodiments, the heteroaryl is a 5-6 monocyclic heteroaryl having 1 or 2 heteroatom ring members independently selected from N, O, and S. In some embodiments, the heteroaryl group contains 3 to 10, 4 to 10, 5 to 10, 5 to 7, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridyl, pyrimidinyl, pyrazinyl, pyridazinyl, pyrrolyl, pyrazolyl, azolyl, oxazolyl, isoxazolyl, thiazolyl, isothiazolyl, imidazolyl, furyl, thienyl, triazolyl (e.g., 1,2,3-triazolyl, 1,2,4-triazolyl, 1,3,4 triazolyl), tetrazolyl, thiadiazolyl (e.g., 1,2,3-thiadiazolyl, 1,2,4-thiadiazolyl, 1,3,4-thiadiazolyl), quinolinyl, isoquinolinyl, indolyl, benzothienyl, benzofuran, benzisoxazole, imidazo[1,2-b]thiazolyl, purinyl, triazinyl, thieno[3,2-b]pyridinyl, imidazo[1,2-a]pyridinyl, 1,5-naphthyridinyl, 1H-pyrazolo[4,3-b]pyridinyl, and oxadiazolyl (e.g., 1,2,3-oxadiazolyl, 1,2,4-oxadiazolyl, 1,3,4-oxadiazolyl).

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S, and B, and wherein the ring-forming carbon atoms and heteroatoms of a heterocycloalkyl group can be optionally substituted by one or more oxo or sulfido (e.g., C(O), S(O), C(S), or S(O)$_2$, etc.). Heterocycloalkyl groups include monocyclic and polycyclic (e.g., having 2 fused rings) systems. Included in heterocycloalkyl are monocyclic and polycyclic 3 to 10, 4 to 10, 5 to 10, 4 to 7, 5 to 7, or 5 to 6 membered heterocycloalkyl groups. Heterocycloalkyl groups can also include spirocycles and bridged rings (e.g., a 5 to 10 membered bridged biheterocycloalkyl ring having one or more of the ring-forming carbon atoms replaced by a heteroatom independently selected from N, O, S, and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4 to 6 membered heterocycloalkyl having 1 or 2 heteroatoms independently selected from N, O, S, and B and having one or more oxidized ring members.

In some embodiments, the heterocycloalkyl is a monocyclic or bicyclic 5-10 membered heterocycloalkyl having 1, 2, 3, or 4 heteroatoms independently selected from N, O, S, and B and having one or more oxidized ring members. In some embodiments, the heterocycloalkyl is a monocyclic or bicyclic 5 to 10 membered heterocycloalkyl having 1, 2, 3, or 4 heteroatoms independently selected from N, O, and S and having one or more oxidized ring members. In some embodiments, the heterocycloalkyl is a monocyclic 5 to 6 membered heterocycloalkyl having 1, 2, 3, or 4 heteroatoms independently selected from N, O, and S and having one or more oxidized ring members.

Non-limiting examples of heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, 1,2,3,4-tetrahydroisoquinoline, benzazapene, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxaadamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl and the like. Other examples of hetereocycloalkyls include 1,6-dihydropyridinyl (e.g., 6-oxo-1,6-dihydropyridinyl).

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, an "alkyl linking group" is a bivalent straight chain or branched alkyl linking group ("alkylene group"). For example, "$C_{o-p}$ cycloalkyl-$C_{n-m}$ alkyl-", "$C_{o-p}$ aryl-$C_{n-m}$ alkyl-", "phenyl-$C_{n-m}$ alkyl-", "heteroaryl-$C_{n-m}$ alkyl-", and "heterocycloalkyl-$C_{n-m}$ alkyl-" contain alkyl linking groups. Examples of "alkyl linking groups" or "alkylene groups" include methylene, ethan-1,1-diyl, ethan-1,2-diyl, propan-1,3-dilyl, propan-1,2-diyl, propan-1,1-diyl and the like.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl, or sulfonyl group.

As used herein, the term "independently selected from" means that each occurrence of a variable or substituent, e.g., $R^{2A}$, are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula (I), (II), etc.) provided herein include stereoisomers of the compounds.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of a-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes, such as those provided in the schemes below.

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Compounds of Formula (I) can be prepared, e.g., using a process as illustrated in the schemes below:

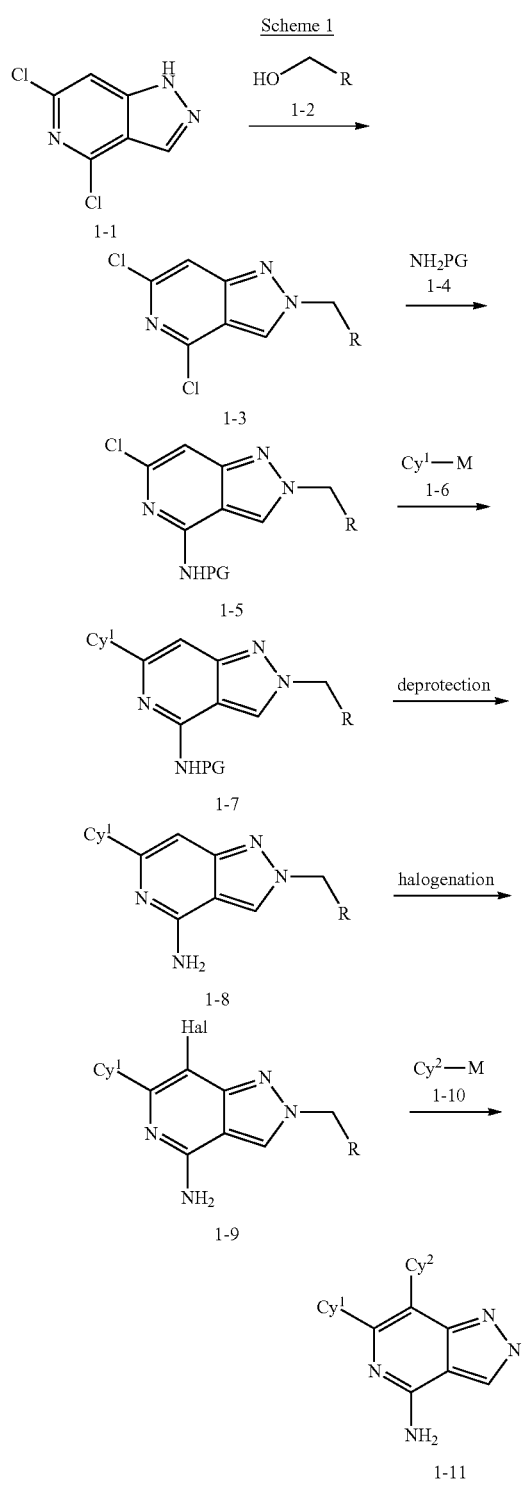

Compounds of formula 1-11 can be prepared via the synthetic route outlined in Scheme 1. An appropriate reaction, such as a Mitsunobu reaction, between starting materials 1-1 and 1-2 can be carried out under suitable conditions (such as using DEAD and Ph3P) to generate intermediate 1-3. A nucleophilic aromatic substitution (SNAr) reaction of intermediate 1-3 with amine 1-4 (PG is a suitable protecting group, such as 2,4-dimethoxybenzyl) affords compound 1-5. Compound 1-5 can then be cross-coupled with an adduct of formula 1-6, in which M is a boronic acid, boronic ester or an appropriately substituted metal (e.g., M is $B(OR)_2$, $Sn(Alkyl)_3$, or Zn-Hal), under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst) to afford the cross-coupling product, which undergoes protecting group removal to generate intermediate 1-8. Halogenation of 1-8 with an appropriate reagent, such as N-bromosuccinimide (NBS), generates intermediate 1-9. The final product 1-11 can then be prepared by reacting compound 1-9 with an adduct of formula 1-10 using reaction conditions similar to that described for the preparation of 1-7 from 1-5. The sequence of the above mentioned synthetic steps can be rearranged, as deemed appropriate, to fit each analogue synthesis.

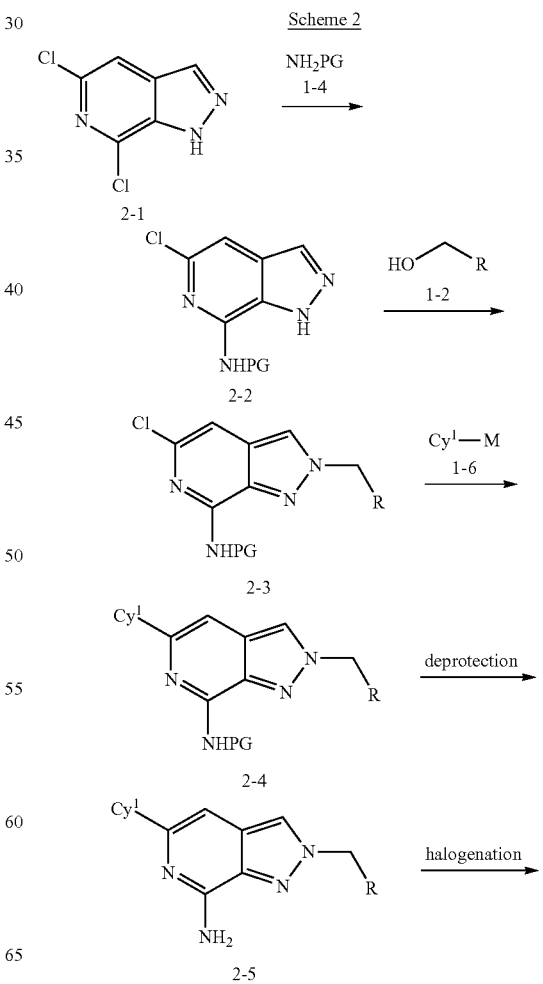

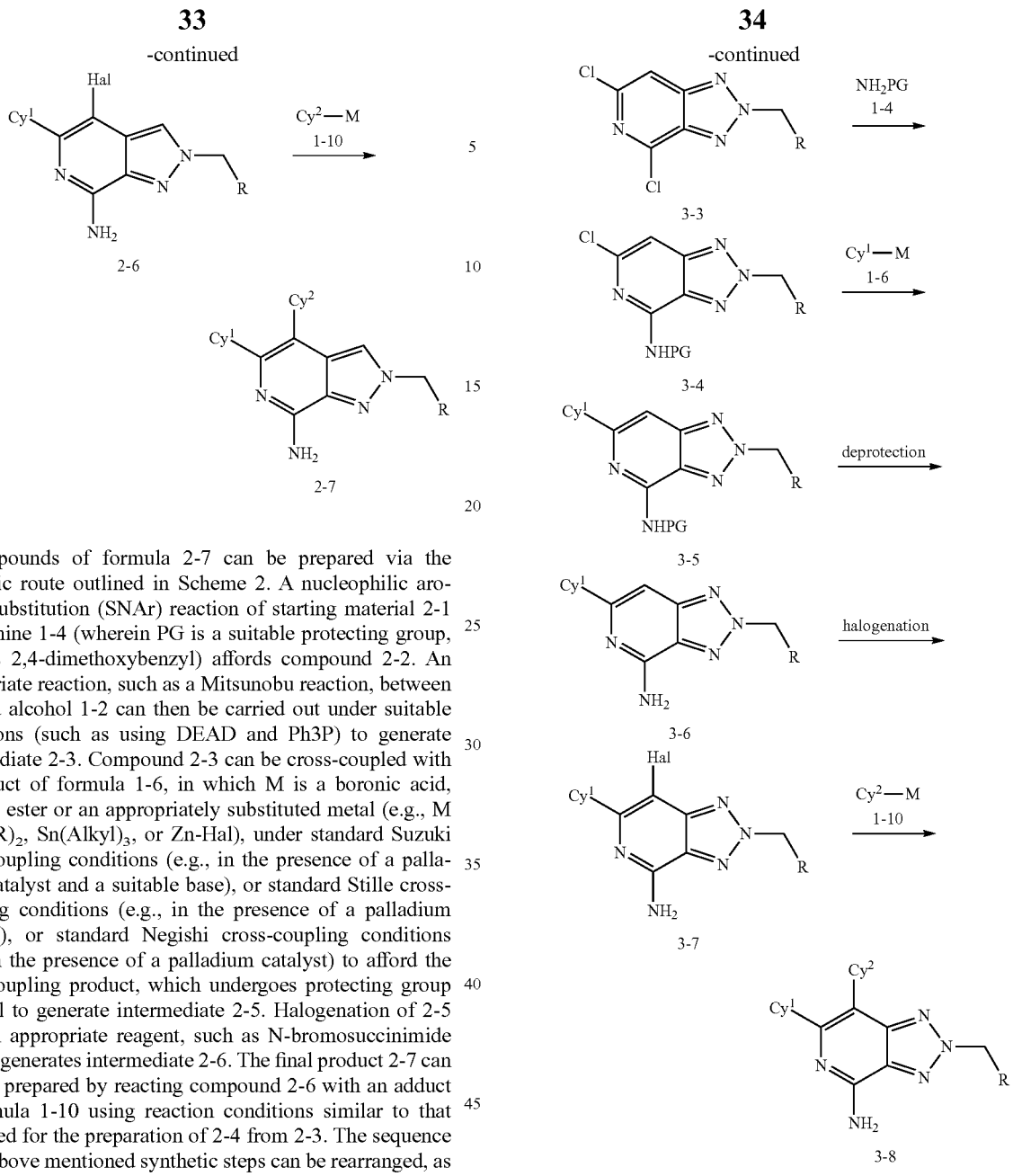

Compounds of formula 2-7 can be prepared via the synthetic route outlined in Scheme 2. A nucleophilic aromatic substitution (SNAr) reaction of starting material 2-1 with amine 1-4 (wherein PG is a suitable protecting group, such as 2,4-dimethoxybenzyl) affords compound 2-2. An appropriate reaction, such as a Mitsunobu reaction, between 2-2 and alcohol 1-2 can then be carried out under suitable conditions (such as using DEAD and Ph3P) to generate intermediate 2-3. Compound 2-3 can be cross-coupled with an adduct of formula 1-6, in which M is a boronic acid, boronic ester or an appropriately substituted metal (e.g., M is B(OR)$_2$, Sn(Alkyl)$_3$, or Zn-Hal), under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst) to afford the cross-coupling product, which undergoes protecting group removal to generate intermediate 2-5. Halogenation of 2-5 with an appropriate reagent, such as N-bromosuccinimide (NBS), generates intermediate 2-6. The final product 2-7 can then be prepared by reacting compound 2-6 with an adduct of formula 1-10 using reaction conditions similar to that described for the preparation of 2-4 from 2-3. The sequence of the above mentioned synthetic steps can be rearranged, as deemed appropriate, to fit each analogue synthesis.

Scheme 3

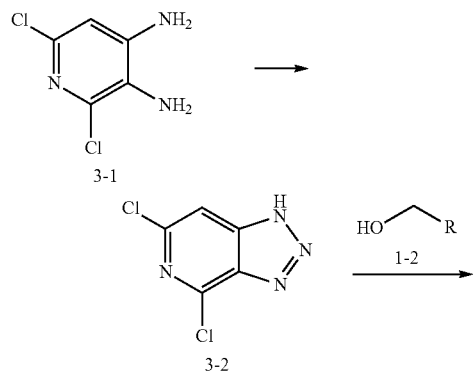

Compounds of formula 3-8 can be prepared via the synthetic route outlined in Scheme 3. A cyclization reaction of starting material 3-1 using appropriate reagents, such as NaNO$_2$ and HCl, affords bicyclic compound 3-2. A coupling reaction, such as a Mitsunobu reaction, between 3-2 and alcohol 1-2 can then be carried out under suitable conditions (such as using DEAD and Ph$_3$P) to generate intermediate 3-3. A nucleophilic aromatic substitution (SNAr) reaction of 3-3 with amine 1-4 (PG is a suitable protecting group, such as 2,4-dimethoxybenzyl) affords compound 3-4. Intermediate 3-4 can then be cross-coupled with an adduct of formula 1-6, in which M is a boronic acid, boronic ester or an appropriately substituted metal [e.g., M is B(OR)$_2$, Sn(Alkyl)$_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst) to afford the cross-coupling product 3-5, which undergoes protecting group removal to generate 3-6. Halogenation of 3-6 with an appropriate reagent, such as N-bromosuccinimide (NBS), generates compound 3-7. The final products 3-8 can then be prepared by reacting compound 3-7 with an adduct of formula 1-10 using reaction conditions similar to that described for the preparation of 3-5 from 3-4. The sequence of the above mentioned synthetic steps can be rearranged, as deemed appropriate, to fit each analogue synthesis.

Methods of Use

The compounds of the present disclosure can modulate the activity of adenosine receptors, such as subtypes A2A and A2B receptors. Accordingly, the compounds, salts or stereoisomers described herein can be used in methods of inhibiting adenosine receptors (e.g., A2A and/or A2B receptors) by contacting the receptor with any one or more of the compounds, salts, or compositions described herein. In some embodiments, the compounds or salts can be used in methods of inhibiting activity of an adenosine receptor in an individual/patient in need of the inhibition by administering an effective amount of a compound or salt of described herein. In some embodiments, modulating is inhibiting. In some embodiments, the contacting is in vivo. In some embodiments, the contacting is ex vivo or in vitro.

The compounds or salts described herein can be selective. By "selective," it is meant that the compound binds to or inhibits an adenosine receptor with greater affinity or potency, respectively, compared to at least one other receptor, kinase, etc. The compounds of the present disclosure can also be dual antagonists (i.e., inhibitors) of adenosine receptors, e.g., A2A and A2B adenosine receptors.

Another aspect of the present disclosure pertains to methods of treating an adenosine receptor associated disease or disorder in an individual (e.g., patient) by administering to the individual in need of such treatment a therapeutically effective amount or dose of one or more compounds of the present disclosure or a pharmaceutical composition thereof. An adenosine receptor associated disease or disorder can include any disease, disorder or condition that is directly or indirectly linked to expression or activity of the adenosine receptor, including overexpression and/or abnormal activity levels.

The compounds of the present disclosure are useful in the treatment of diseases related to the activity of adenosine receptors including, for example, cancer, inflammatory diseases, cardiovascular diseases, neurodegenerative diseases, immunomodulatory disorders, central nerve system diseases, and diabetes.

Based on the compelling roles of adenosine, e.g., A2A, A2B, receptors in multiple immunosuppressive mechanisms, developing inhibitors can boost the immune system to suppress tumor progression. Adenosine receptor inhibitors can be used to treat, alone or in combination with other therapies, bladder cancer, lung cancer (e.g., non-small cell lung cancer (NSCLC), lung metastasis), melanoma (e.g., metastatic melanoma), breast cancer, cervical cancer, ovarian cancer, colorectal cancer, pancreatic cancer, esophageal cancer, prostate cancer, kidney cancer, skin cancer, thyroid cancer, liver cancer, uterine cancer, head and neck cancer, and renal cell carcinoma (Antonioli, L. et al., *Nature Reviews Cancer*, 2013, 13, 842-857). See also, https://globenewswire.com/news-release/2017/04/04/954192/0/en/Corvus-Pharmaceuticals-Announces-Interim-Results-from-Ongoing-Phase-1-1b-Study-Demonstrating-Safety-and-Clinical-Activity-of-Lead-Checkpoint-Inhibitor-CPI-444-in-Patients-with-Adva.html; Cekic C. et al., *J Immunol*, 2012, 188:198-205; Iannone, R. et al., *Am. J. Cancer Res.* 2014, 4:172-181 (study shows that both A2A and CD73 blockade enhance the antitumor activity of anti-CTLA-4 mAb therapy in a Bl6F10 murine melanoma model); Iannone, R. et al., *Neoplasia*, 2013, 15:1400-1410 and Beavis PA., et al., *Proc Natl Acad Sci. USA*, 2013, 110:14711-14716 (study shows that A2A and CD73 blockade decreased metastasis in 4T1 breast tumor model with has high CD73 expression). In some embodiments, the prostate cancer is metastatic castrate-resistant prostate carcinoma (mCRPC). In some embodiments, the colorectal cancer is colorectal carcinoma (CRC).

In some embodiments, the disease or disorder is lung cancer (e.g., non-small cell lung cancer), melanoma, pancreatic cancer, breast cancer, head and neck squamous cell carcinoma, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is mesothelioma or adrenocarcinoma. In some embodiments, the disease or disorder is mesothelioma. In some embodiments, the disease or disorder is adrenocarcinoma.

MDSC (myeloid-derived suppressor cells) are a heterogenous group of immune cells from the myeloid lineage (a family of cells that originate from bone marrow stem cells). MDSCs strongly expand in pathological situations such as chronic infections and cancer, as a result of an altered haematopoiesis. MDSCs are discriminated from other myeloid cell types in which they possess strong immunosuppressive activities rather than immunostimulatory properties. Similar to other myeloid cells, MDSCs interact with other immune cell types including T cells, dendritic cells, macrophages and natural killer cells to regulate their functions. In some embodiments, the compounds, etc. described herein can be used in methods related to cancer tissue (e.g., tumors) with high infiltration of MDSCs, including Solid tumors with high basal level of macrophage and/or MDSC infiltration.

In some embodiments, the compounds of the disclosure can be used in treating pulmonary inflammation, including bleomycin-induced pulmonary fibrosis and injury related to adenosine deaminase deficiency (Baraldi, et al., *Chem. Rev.*, 2008, 108, 238-263).

In some embodiments, the compounds of the disclosure can be used as a treatment for inflammatory disease such as allergic reactions (e.g., A2B adenosine receptor dependent allergic reactions) and other adenosine receptor dependent immune reactions. Further inflammatory diseases that can be treated by compounds of the disclosure include respiratory disorders, sepsis, reperfusion injury, and thrombosis.

In some embodiments, the compounds of the disclosure can be used as a treatment for cardiovascular disease such as coronary artery disease (myocardial infarction, angina pectoris, heart failure), cerebrovascular disease (stroke, transient ischemic attack), peripheral artery disease, and aortic atherosclerosis and aneurysm. Atherosclerosis is an underlying etiologic factor in many types of cardiovascular disease. Atherosclerosis begins in adolescence with fatty streaks, which progress to plaques in adulthood and finally results in thrombotic events that cause occlusion of vessels leading to clinically significant morbidity and mortality. Antagonists to the A2B adenosine receptor and A2A adenosine receptor may be beneficial in preventing atherosclerotic plaque formation (Eisenstein, A. et al., *J. Cell Physiol.*, 2015, 230(12), 2891-2897).

In some embodiments, the compounds of the disclosure can be used as a treatment for disorders in motor activity; deficiency caused by degeneration of the striatonigral dopamine system; and Parkinson's disease; some of the motivational symptoms of depression (Collins, L. E. et al. *Pharmacol. Biochem. Behav.*, 2012, 100, 498-505.).

In some embodiments, the compounds of the disclosure can be used as a treatment for diabetes and related disorders, such as insulin resistance. Diabetes affects the production of adenosine and the expression of A2B adenosine receptors (A2BRs) that stimulate IL-6 and CRP production, insulin resistance, and the association between A2BR gene single-nucleotide polymorphisms (ADORA2B SNPs) and inflammatory markers. The increased A2BR signaling in diabetes may increase insulin resistance in part by elevating pro-inflammatory mediators. Selective A2BR blockers may be useful to treat insulin resistance (Figler, R. A. et al. *Diabetes*, 2011, 60 (2), 669-679).

It is believed that compounds provided herein, e.g., compounds of Formula (I), or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient", used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies
I. Immune-Checkpoint Therapies

In some embodiments, A2A and A2B dual inhibitors provided herein can be used in combination with one or more immune checkpoint inhibitors for the treatment of cancer as described herein. In one embodiment, the combination with one or more immune checkpoint inhibitors as described herein can be used for the treatment of melanoma. Compounds of the present disclosure can be used in combination with one or more immune checkpoint inhibitors. Exemplary immune checkpoint inhibitors include inhibitors against immune checkpoint molecules such as CD20, CD28, CD40, CD122, CD96, CD73, CD47, GITR, CSF1R, JAK, PI3K delta, PI3K gamma, TAM, arginase, HPK1, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the A2A and A2B dual inhibitors provided herein can be used in combination with one or more agonists of immune checkpoint molecules, e.g., OX40, CD27, OX40, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX4OL fusion protein. In some embodiments, the anti-OX40 antibody is MEDI0562, MOXR-0916, PF-04518600, GSK3174998, or BMS-986178. In some embodiments, the OX4OL fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3, tumor specific antigens (e.g., CD70) or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer. Examples of diseases and indications treatable with combination therapies include those as described herein.

The compounds of the present disclosure can be used in combination with one or more additional pharmaceutical agents such as, for example, chemotherapeutics, immune-oncology agents, metabolic enzyme inhibitors, chemokine receptor inhibitors, and phosphatase inhibitors, as well as targeted therapies such as Bcr-Abl, EGFR, HER2, JAK, c-MET, VEGFR, PDGFR, c-Kit, IGF-1R, RAF and FAK kinase inhibitors. The one or more additional pharmaceutical agents can be administered to a patient simultaneously or sequentially.

For example, the compounds as disclosed herein can be combined with one or more inhibitors of the following kinases for the treatment of cancer and other diseases or disorders described herein: Akt1, Akt2, Akt3, TGF-β, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Non-limiting examples of inhibitors that can be combined with the compounds of the present disclosure for treatment of cancer and other diseases and disorders described herein include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a Pim inhibitor, a CSF1R inhibitor, a TAM receptor tyrosine kinases (Tyro-3, Ax1, and Mer), a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml 1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumortargeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, streptozocin, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib, and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a PI3K inhibitor of the present disclosure with an additional agent.

In some embodiments, the compounds of the disclosure can be used in combination with an inhibitor of JAK or PI3K8.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fc alpha or Fc gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, Leishmania, Staphylococcus aureus, Pseudomonas Aeruginosa.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, Candida (albicans, krusei, glabrata, tropicalis, etc.), *Cryptococcus neoformans*, *Aspergillus* (*fumigatus, niger*, etc.), Genus *Mucorales* (*mucor, absidia, rhizophus*), *Sporothrix schenkii*, *Blastomyces dermatitidis, Paracoccidioides brasiliensis*, *Coccidioides immitis* and *Histoplasma capsulatum*. Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating A2A and/or A2B receptors in tissue samples, including human, and for identifying A2A and/or A2B antagonists by inhibition binding of a labeled compound. Substitution of one or more of the atoms of the compounds of the present disclosure can also be useful in generating differentiated ADME (Adsorption, Distribution, Metabolism and Excretion.) Accordingly, the present disclosure includes adenosine receptor (e.g., A2A and/or A2B) assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium) $^{11}$C, $^{13}$C, $^{14}$C, $^{13}$N, $^{15}$N, $^{15}$O, $^{17}$P, $^{18}$P, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups in any of the disclosed Formulas, e.g., Formula (I), can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of any "alkyl", "alkenyl", "alkynyl", "aryl", "phenyl", "cycloalkyl", "heterocycloalkyl", or "heteroaryl" substituents or "—$C_{1-6}$ alkyl-", "alkylene", "alkenylene" and "alkynylene" linking groups, as described herein, are each optionally replaced by a deuterium atom.

Synthetic methods for including isotopes into organic compounds are known in the art (Deuterium Labeling in Organic Chemistry by Alan F Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radiolabeled compounds will depend on the specific application of that radio-labeled compound. For example, for in vitro adenosine receptor labeling and competition assays, compounds that incorporate $^3$H, $^{14}$C, $^{82}$Br, $^{125}$I, $^{131}$I, or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind an adenosine receptor by monitoring its concentration variation when contacting with the adenosine receptor, through tracking of the labeling. For example, a test compound (labeled) can be evaluated for its ability to reduce binding of another compound which is known to bind to a an adenosine receptor (i.e., standard compound). Accordingly, the ability of a test compound to compete with the standard compound for binding to the adenosine receptor directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of adenosine receptor-associated diseases or disorders (such as, e.g., cancer, an inflammatory disease, a cardiovascular disease, or a neurodegenerative disease) which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of an adenosine receptor (e.g., A2A and/or A2B) according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Hague, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 µm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows: pH=2 purifications: Waters Sunfire™ $C_{18}$ 5 µm, 30×100 mm or Waters XBridge™ $C_{18}$ 5 µm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, J. Comb. Chem., 6, 874-883 (2004)).

pH=10 purifications: Waters XBridge™ $C_{18}$ 5 µm, 30×100 mm column, eluting with mobile phase A: 0.1% $NH_4OH$ in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, J. Comb. Chem., 6, 874-883 (2004)).

Example 1

3-(4-amino-2-(pyridin-2-ylmethyl)-7-(pyrimidin-4-yl)-2H-pyrazolo[4,3-c]pyridin-6-yl)benzonitrile

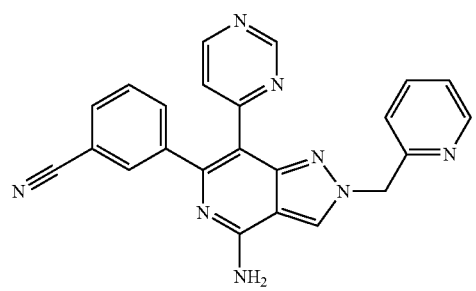

51

Step A. 4,6-dichloro-2-(pyridin-2-ylmethyl)-2H-pyrazolo[4,3-c]pyridine

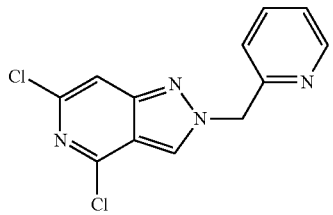 [SMILES: Clc1cc2nn(Cc3ccccn3)cc2c(Cl)n1]

To a mixture of 4,6-dichloro-1H-pyrazolo[4,3-c]pyridine (1000 mg, 5.32 mmol), pyridin-2-ylmethanol (0.77 mL, 7.98 mmol) and triphenylphosphine (2790 mg, 10.64 mmol) in DCM (10 mL) was added diisopropyl azodicarboxylate (1.57 mL, 7.98 mmol) at 0° C. The reaction mixture was stirred at 0° C. overnight. Direct chromatography on silica gel column afforded the desired product (571 mg, 39%). LC-MS calculated for $C_2H_9Cl_2N_4$: 279.0 $(M+H)^+$; found: 279.3 $(M+H)^+$.

Step B. 6-chloro-N-(2,4-dimethoxybenzyl)-2-(pyridin-2-ylmethyl)-2H-pyrazolo[4,3-c]pyridin-4-amine

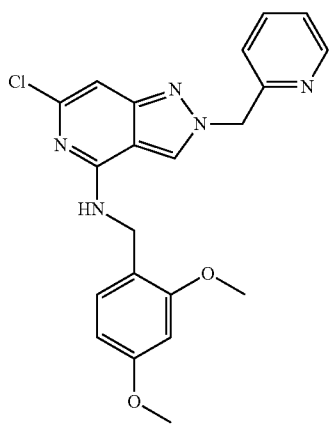 [SMILES: COc1ccc(CNc2nc(Cl)cc3nn(Cc4ccccn4)cc23)c(OC)c1]

To the mixture of 4,6-dichloro-2-(pyridin-2-ylmethyl)-2H-pyrazolo[4,3-c]pyridine (500 mg, 1.791 mmol), (2,4-dimethoxyphenyl)methanamine (0.30 mL, 1.97 mmol) in 1,4-dioxane (10 mL) was added triethylamine (0.30 mL, 2.15 mmol). The reaction mixture was stirred at 110° C. overnight. Direct chromatography on silica gel column afforded the desired product (609 mg, 83%). LC-MS calculated for $C_{21}H_{21}ClN_5O_2$: 410.1 $(M+H)^+$; found: 410.3 $(M+H)^+$.

52

Step C. 3-(4-((2,4-dimethoxybenzyl)amino)-2-(pyridin-2-ylmethyl)-2H-pyrazolo[4,3-c]pyridin-6-yl)benzonitrile

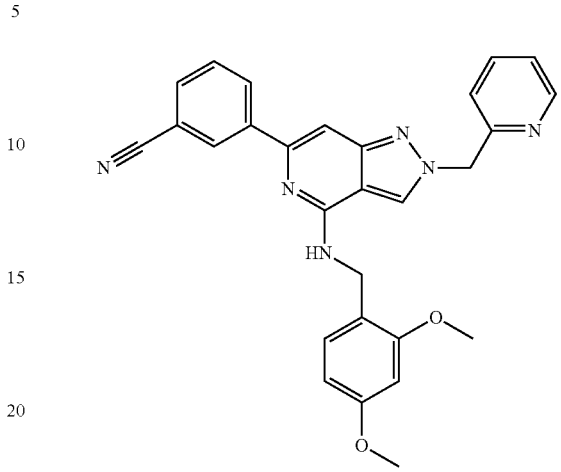

To the mixture of 6-chloro-N-(2,4-dimethoxybenzyl)-2-(pyridin-2-ylmethyl)-2H-pyrazolo[4,3-c]pyridin-4-amine (609 mg, 1.486 mmol), (3-cyanophenyl)boronic acid (327 mg, 2.229 mmol) in 1,4-dioxane (10 mL) and water (1 mL) was added cesium carbonate (968 mg, 2.97 mmol). The reaction mixture was de-gassed under $N_2$ and then chloro(2-dicyclohexylphosphino-2',4',6'-triisopropyl-1,1'-biphenyl)[2-(2'-amino-1,1'-biphenyl)]palladium(II) (117 mg, 0.149 mmol) was added. The mixture was stirred at 120° C. under microwave for 90 minutes. The reaction was quenched with 20 mL of ethyl acetate and 20 mL of water. The organic phase was separated and the aqueous solution was extracted with ethyl acetate twice. The combined extracts were dried over $Na_2SO_4$, filtered and evaporated under reduced pressure. The residue was purified on silica gel column to afford the desired product. LC-MS calculated for $C_{28}H_{25}N_6O_2$: 477.2 $(M+H)^+$; found: 477.3 $(M+H)^+$.

Step D. 3-(4-amino-2-(pyridin-2-ylmethyl)-2H-pyrazolo[4,3-c]pyridin-6-yl)benzonitrile

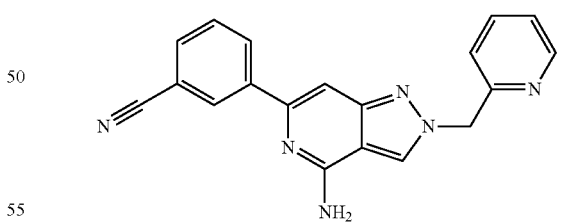

The solution of 3-(4-((2,4-dimethoxybenzyl)amino)-2-(pyridin-2-ylmethyl)-2H-pyrazolo[4,3-c]pyridin-6-yl)benzonitrile (500 mg, 1.049 mmol) in TFA (5.00 mL) was stirred at 100° C. for 30 minutes. TFA was evaporated under reduced pressure and then 20 mL of saturated $NaHCO_3$ aqueous solution and 20 mL of ethyl acetate were added. The organic phase was separated and the aqueous solution was extracted with ethyl acetate twice. The combined extracts were dried over $Na_2SO_4$, filtered and evaporated under reduced pressure. The residue was purified on silica gel column to afford the desired product (273 mg, 80%). LC-MS calculated for $C_{19}H_{15}N_6$: 327.1 (M+H)$^+$; found: 327.3 (M+H)$^+$.

Step E. 3-(4-amino-7-bromo-2-(pyridin-2-ylmethyl)-2H-pyrazolo[4,3-c]pyridin-6-yl)benzonitrile

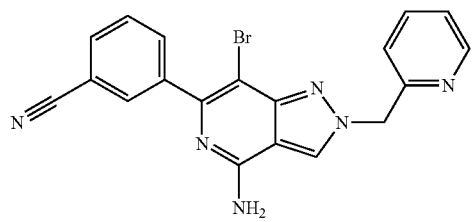 [SMILES: N#Cc1cccc(-c2nc(N)c3cn(Cc4ccccn4)nc3c2Br)c1]

The reaction mixture of 3-(4-amino-2-(pyridin-2-ylmethyl)-2H-pyrazolo[4,3-c]pyridin-6-yl)benzonitrile (273 mg, 0.836 mmol) and 1-bromopyrrolidine-2,5-dione (156 mg, 0.878 mmol) in THF (10 mL) was stirred at 0° C. for 30 minutes and quenched with saturated NaHCO$_3$ aqueous solution. The organic phase was separated, dried over Na$_2$SO$_4$, filtered and evaporated under reduced pressure. The resulting residue was purified on silica gel column to afford the desired product (251 mg, 74.0%). LC-MS calculated for $C_{19}H_{14}BrN_6$: 405.0 (M+H)$^+$ and 407.0 (M+H)$^+$; found: 405.2 (M+H)$^+$ and 407.3 (M+H)$^+$.

Step F. 3-(4-amino-2-(pyridin-2-ylmethyl)-7-(pyrimidin-4-yl)-2H-pyrazolo[4,3-c]pyridin-6-yl)benzonitrile

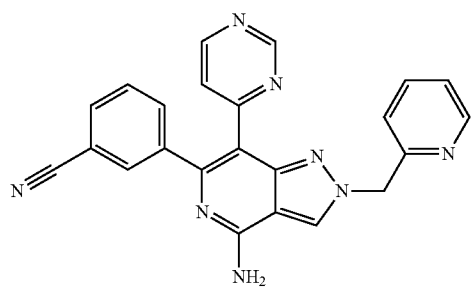

A mixture of 3-(4-amino-7-bromo-2-(pyridin-2-ylmethyl)-2H-pyrazolo[4,3-c]pyridin-6-yl)benzonitrile (25 mg, 0.062 mmol), 4-(tributylstannyl)pyrimidine (34.2 mg, 0.093 mmol), and copper(I) chloride (7.33 mg, 0.074 mmol), lithium chloride (3.14 mg, 0.074 mmol) and tetrakis(triphenylphosphine)palladium(0) (7.13 mg, 6.17 μmol in THF (1 ml) was first purged with N$_2$, and then heated and stirred at 90° C. for 2 h. The reaction was diluted with methanol and purified with prep-LCMS (pH=2) to give the desired product. LC-MS calculated for $C_{23}F_{17}N_8$: 405.2 (M+H)$^+$; found: 405.3 (M+H)$^+$.

Example 2

3-(4-amino-7-(1-ethyl-1H-pyrazol-5-yl)-2-(pyridin-2-ylmethyl)-2H-pyrazolo[4,3-c]pyridin-6-yl)benzonitrile

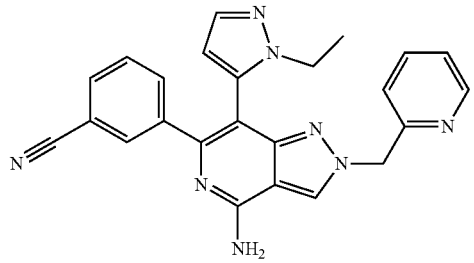

To the mixture of 3-(4-amino-7-bromo-2-(pyridin-2-ylmethyl)-2H-pyrazolo[4,3-c]pyridin-6-yl)benzonitrile (20 mg, 0.049 mmol) and 1-ethyl-5-(4,4,5,5-tetramethyl-1,3,2-dioxaborolan-2-yl)-1H-pyrazole (21.92 mg, 0.099 mmol) in 1,4-dioxane (2 mL) and water (0.2 mL) was added cesium carbonate (16.08 mg, 0.049 mmol). The resulting mixture was sparged with N$_2$ for 2 min and then chloro(2-dicyclohexylphosphino-2',4',6'-triisopropyl-1,1'-biphenyl)[2-(2'-amino-1,1'-biphenyl)]palladium(II) (3.88 mg, 4.94 μmol was added. The reaction mixture was stirred at 120° C. for 1.5 h and then was diluted with methanol. Direct purification on prep. HPLC afforded the desired product. LC-MS calculated for $C_{24}H_{21}N_8$: 421.2 (M+H)$^+$; found: 421.3 (M+H)$^+$.

Example 3

3-(4-amino-2-((3-fluoropyridin-2-yl)methyl)-7-(pyrimidin-4-yl)-2H-pyrazolo[4,3-c]pyridin-6-yl)benzonitrile

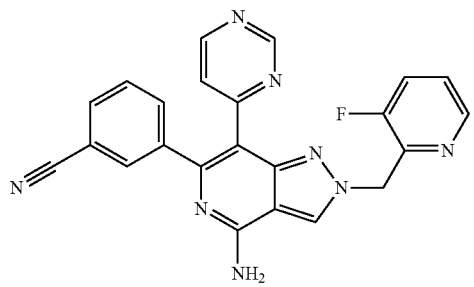

The above title compound was synthesized according to the procedures described in Example 1, except by using (3-fluoropyridin-2-yl)methanol instead of using (pyridin-2-yl)methanol. LC-MS calculated for $C_{23}H_{16}FN_8$: 423.1 (M+H)$^+$; found: 423.3 (M+H)$^+$.

Example 4

3-(4-amino-2-((1-methyl-1H-pyrazol-3-yl)methyl)-7-(pyrimidin-4-yl)-2H-pyrazolo[4,3-c]pyridin-6-yl)benzonitrile

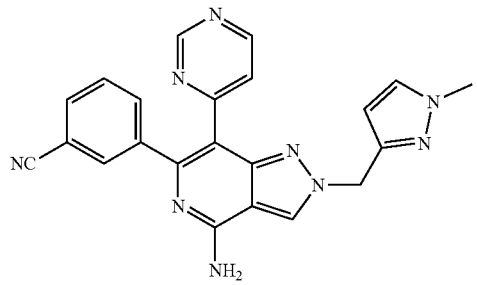 [SMILES: Cn1ccc(Cn2cc3c(N)nc(-c4cccc(C#N)c4)c(-c4ccncn4)c3n2)n1]

The above title compound was synthesized according to the procedures described in Example 1, except by using (1-methyl-1H-pyrazol-3-yl)methanol instead of using (pyridin-2-yl)methanol. LC-MS calculated for $C_{22}H_{18}N_9$: 408.2 (M+H)$^+$; found: 408.3 (M+H)$^+$.

Example 5

3-(4-amino-2-((6-methylpyridin-2-yl)methyl)-7-(pyrimidin-4-yl)-2H-pyrazolo[4,3-c]pyridin-6-yl)benzonitrile

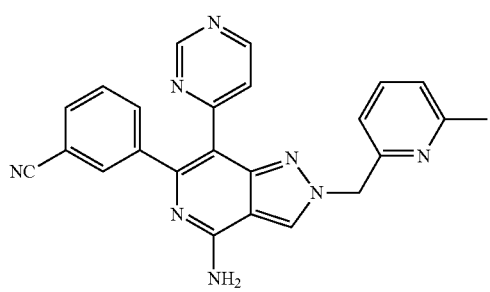 [SMILES: Cc1cccc(Cn2cc3c(N)nc(-c4cccc(C#N)c4)c(-c4ccncn4)c3n2)n1]

The above title compound was synthesized according to the procedures described in Example 1, except by using (6-methylpyridin-2-yl)methanol instead of using (pyridin-2-yl)methanol. LC-MS calculated for $C_{24}H_{19}N_8$: 419.2 (M+H)$^+$; found: 419.3 (M+H)$^+$.

Example 6

3-(4-amino-2-(pyridin-2-ylmethyl)-7-(pyridin-4-yl)-2H-pyrazolo[4,3-c]pyridin-6-yl)benzonitrile

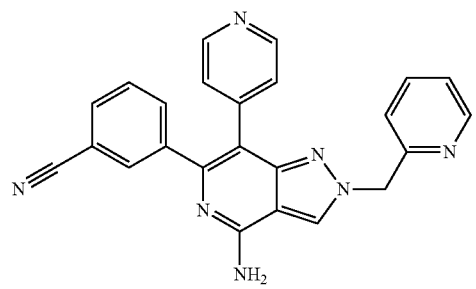 [SMILES: N#Cc1cccc(-c2nc(N)c3cn(Cc4ccccn4)nc3c2-c2ccncc2)c1]

The above title compound was synthesized according to the procedures described in Example 2, except by using pyridin-4-ylboronic acid instead of using 1-ethyl-5-(4,4,5,5-tetramethyl-1,3,2-dioxaborolan-2-yl)-1H-pyrazole. LC-MS calculated for $C_{24}H_{18}N_7$: 404.2 (M+H)$^+$; found: 404.3 (M+H)$^+$.

Example 7

3-(4-amino-2-(2-fluorobenzyl)-7-(pyrimidin-4-yl)-2H-pyrazolo[4,3-c]pyridin-6-yl)benzonitrile

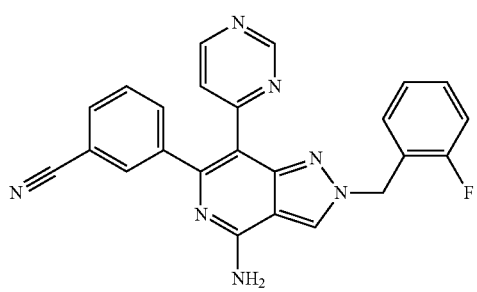 [SMILES: N#Cc1cccc(-c2nc(N)c3cn(Cc4ccccc4F)nc3c2-c2ccncn2)c1]

The above title compound was synthesized according to the procedures described in Example 1, except by using (2-fluorophenyl)methanol instead of using (pyridin-2-yl)methanol. LC-MS calculated for $C_{24}H_{17}FN_7$: 422.2 (M+H)$^+$; found: 422.3 (M+H)$^+$.

Example 8

3-(7-amino-2-(pyridin-2-ylmethyl)-4-(pyrimidin-4-yl)-2H-pyrazolo[3,4-c]pyridin-5-yl)benzonitrile

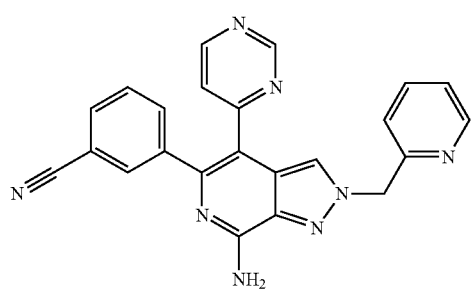 [SMILES: N#Cc1cccc(-c2nc(N)c3nn(Cc4ccccn4)cc3c2-c2ccncn2)c1]

Step A. 5-chloro-N-(2,4-dimethoxybenzyl)-1H-pyrazolo[3,4-c]pyridin-7-amine

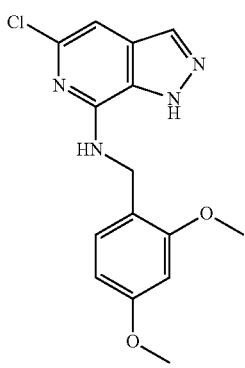 [SMILES: COc1ccc(CNc2nc(Cl)cc3cn[nH]c23)c(OC)c1]

The reaction mixture of 5,7-dichloro-1H-pyrazolo[3,4-c]pyridine (1000 mg, 5.32 mmol), (2,4-dimethoxyphenyl)methanamine (0.879 mL, 5.85 mmol) and triethylamine (0.890 mL, 6.38 mmol) in 1,4-dioxane (10 mL) was stirred at 110° C. for 3 days. Direct purification on silica gel column afforded the desired product (1.35 g, 80%). LC-MS calculated for $C_{15}H_{16}ClN_4O_2$: 319.1 (M+H)$^+$; found: 319.3 (M+H)$^+$.

Step B. 5-chloro-N-(2,4-dimethoxybenzyl)-2-(pyridin-2-ylmethyl)-2H-pyrazolo[3,4-c]pyridin-7-amine

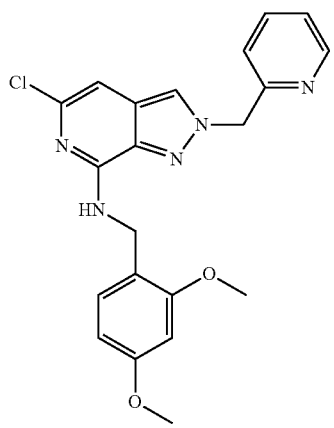 [SMILES: COc1ccc(CNc2nc(Cl)cc3cn(Cc4ccccn4)nc23)c(OC)c1]

The reaction mixture of 5-chloro-N-(2,4-dimethoxybenzyl)-1H-pyrazolo[3,4-c]pyridin-7-amine (1350 mg, 4.24 mmol), pyridin-2-ylmethanol (555 mg, 5.08 mmol) and triphenylphosphine (2222 mg, 8.47 mmol) in DCM (20 mL) was added diisopropyl azodicarboxylate (1.0 mL, 5.08 mmol) at 0° C. The reaction was stirred at 0° C. overnight. Direct purification on silica gel column afforded the desired product (535 mg, 31%). LC-MS calculated for $C_{21}H_{21}ClN_5O_2$: 410.1 (M+H)$^+$; found: 410.2 (M+H)$^+$.

Step C. 3-(7-((2,4-dimethoxybenzyl)amino)-2-(pyridin-2-ylmethyl)-2H-pyrazolo[3,4-c]pyridin-5-yl)benzonitrile

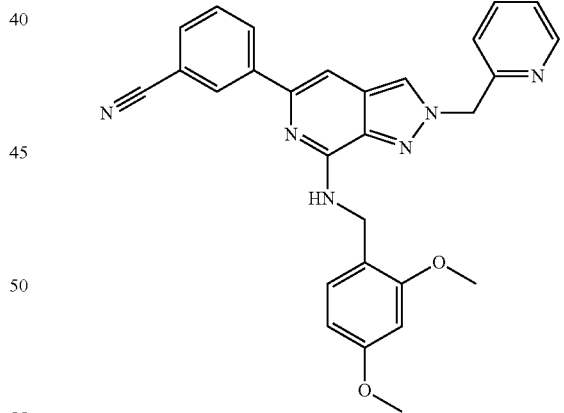

To the mixture of 5-chloro-N-(2,4-dimethoxybenzyl)-2-(pyridin-2-ylmethyl)-2H-pyrazolo[3,4-c]pyridin-7-amine (535 mg, 1.305 mmol) and (3-cyanophenyl)boronic acid (384 mg, 2.61 mmol) in 1,4-dioxane (10 mL) and water (1 mL) was added cesium carbonate (851 mg, 2.61 mmol). The mixture was purged with $N_2$ and chloro(2-dicyclohexylphosphino-2',4',6'-triisopropyl-1,1'-biphenyl)[2-(2'-amino-1,1'-biphenyl)]palladium(II) (103 mg, 0.131 mmol) was added. The reaction mixture was stirred at 120° C. under microwave irradiation for 90 minutes. The reaction was quenched with 20 mL of ethyl acetate and 20 mL of water.

The organic phase was separated and the aqueous solution was extracted with ethyl acetate twice. The combined extracts were dried over Na₂SO₄, filtered and evaporated under reduced pressure. The residue was purified on silica gel column to afford the desired product (420 mg, 68%). LC-MS calculated for $C_{28}H_{25}N_6O_2$: 477.2 (M+H)⁺; found: 477.3 (M+H)⁺.

Step D. 3-(7-amino-2-(pyridin-2-ylmethyl)-2H-pyrazolo[3,4-c]pyridin-5-yl)benzonitrile

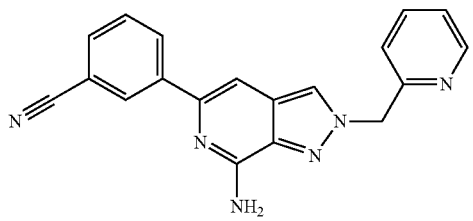 [SMILES: N#Cc1cccc(-c2cc3cn(Cc4ccccn4)nc3c(N)n2)c1]

The solution of 3-(7-((2,4-dimethoxybenzyl)amino)-2-(pyridin-2-ylmethyl)-2H-pyrazolo[3,4-c]pyridin-5-yl)benzonitrile (420.3 mg, 0.882 mmol) in TFA (5 mL) was stirred at 100° C. for 30 minutes. TFA was evaporated under reduced pressure and then 20 mL of saturated NaHCO₃ aqueous solution and 20 mL of ethyl acetate were added. The organic phase was separated and the aqueous solution was extracted with ethyl acetate twice. The combined extracts were dried over Na₂SO₄, filtered and evaporated under reduced pressure. The residue was purified on silica gel column to afford the desired product (244 mg, 85%). LC-MS calculated for $C_{19}H_{15}N_6$: 327.1 (M+H)⁺; found: 327.2 (M+H)⁺.

Step E. 3-(7-amino-4-bromo-2-(pyridin-2-ylmethyl)-2H-pyrazolo[3,4-e]pyridin-5-yl)benzonitrile

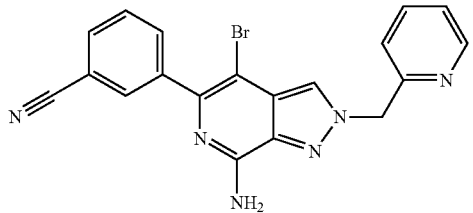 [SMILES: N#Cc1cccc(-c2nc(N)c3nn(Cc4ccccn4)cc3c2Br)c1]

The mixture of 3-(7-amino-2-(pyridin-2-ylmethyl)-2H-pyrazolo[3,4-c]pyridin-5-yl)benzonitrile (357 mg, 1.094 mmol) and 1-bromopyrrolidine-2,5-dione (204 mg, 1.149 mmol) in THF (10 mL) was stirred at 0° C. for 1 h and then quenched with saturated NaHCO₃ aqueous solution. The organic phase was separated, dried over Na₂SO₄, filtered and evaporated under reduced pressure. The resulting residue was purified on silica gel column to afford the desired product (314 mg, 71%). LC-MS calculated for $C_{19}H_{14}BrN_6$: 405.0 (M+H)⁺ and 407.0 (M+H)⁺; found: 405.1 (M+H)⁺ and 407.2 (M+H)⁺.

Step F. 3-(7-amino-2-(pyridin-2-ylmethyl)-4-(pyrimidin-4-yl)-2H-pyrazolo[3,4-c]pyridin-5-yl)benzonitrile

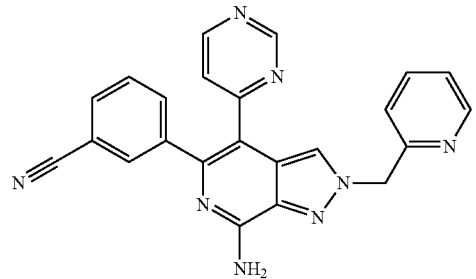

A mixture of 3-(7-amino-4-bromo-2-(pyridin-2-ylmethyl)-2H-pyrazolo[3,4-c]pyridin-5-yl)benzonitrile (40 mg, 0.099 mmol), 4-(tributylstannyl)pyrimidine (109 mg, 0.296 mmol), and copper(I) chloride (11.73 mg, 0.118 mmol), lithium chloride (5.02 mg, 0.118 mmol) and tetrakis(triphenylphosphine)palladium(0) (11.41 mg, 9.87 μmol in THF (1 ml) was first purged with N₂, and then heated and stirred at 90° C. for 2 h. The reaction was diluted with methanol and purified with prep-LCMS (pH 2) to give the desired product. LC-MS calculated for $C_{23}H_{17}N_8$: 405.2 (M+H)⁺; found: 405.3 (M+H)⁺.

Example 9

3-(7-amino-4-(1-ethyl-1H-pyrazol-5-yl)-2-(pyridin-2-ylmethyl)-2H-pyrazolo[3,4-c]pyridin-5-yl)benzonitrile

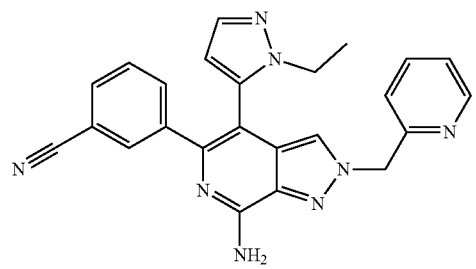

To the mixture of 3-(7-amino-4-bromo-2-(pyridin-2-ylmethyl)-2H-pyrazolo[3,4-c]pyridin-5-yl)benzonitrile (162 mg, 0.400 mmol) and (1-ethyl-1H-pyrazol-5-yl)boronic acid (55.9 mg, 0.400 mmol) 1,4-dioxane (2.0 mL) and water (0.2 mL) was added cesium carbonate (260 mg, 0.799 mmol). The resulting mixture was sparged with N₂ for 2 min and chloro(2-dicyclohexylphosphino-2',4',6'-triisopropyl-1,1'-biphenyl)[2-(2'-amino-1,1'-biphenyl)]palladium(II) (0.040 mmol) was added. The reaction mixture was stirred at 120° C. under microwave irradiation for 90 min. The reaction mixture was diluted with methanol. Direct purification on prep. HPLC afforded the desired product. LC-MS calculated for $C_{24}H_{21}N_8$: 421.2 (M+H)⁺; found: 421.3 (M+H)⁺.

Example 10

3-(7-amino-2-((6-methylpyridin-2-yl)methyl)-4-(pyrimidin-4-yl)-2H-pyrazolo[3,4-c]pyridin-5-yl)benzonitrile

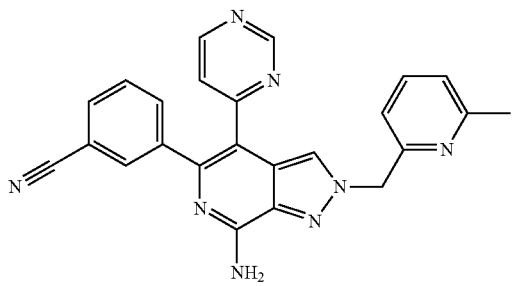

The above title compound was synthesized according to the procedures described in Example 8, except by using (6-methylpyridin-2-yl)methanol instead of using (pyridin-2-yl)methanol. LC-MS calculated for $C_{24}H_{19}N_8$: 419.2 (M+H)$^+$; found: 419.3 (M+H)$^+$.

Example 11

3-(7-amino-4-(1-ethyl-1H-pyrazol-5-yl)-2-((6-methylpyridin-2-yl)methyl)-2H-pyrazolo[3,4-c]pyridin-5-yl)benzonitrile

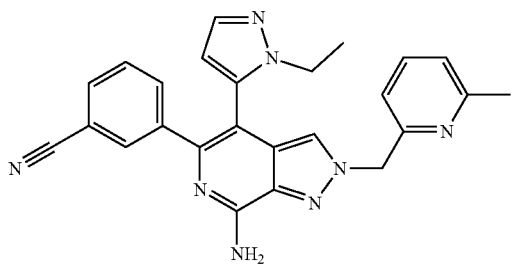

To the mixture of 3-(7-amino-4-bromo-2-((6-methylpyridin-2-yl)methyl)-2H-pyrazolo[3,4-c]pyridin-5-yl)benzonitrile (60 mg, 0.143 mmol) and (1-ethyl-1H-pyrazol-5-yl)boronic acid (20.03 mg, 0.143 mmol) in 1,4-dioxane (2.0 mL) and water (0.2 mL) was added cesium carbonate (93 mg, 0.286 mmol). The resulting mixture was sparged with $N_2$ for 1 min and chloro(2-dicyclohexylphosphino-2',4',6'-triisopropyl-1,1'-biphenyl)[2-(2'-amino-1,1'-biphenyl)]palladium(II)(0.014 mmol) was added. The reaction mixture was stirred at 120° C. under microwave irradiation for 90 min. The reaction mixture was diluted with methanol. Direct purification on prep. HPLC (pH=2) afforded the desired product. LC-MS calculated for $C_{25}H_{23}N_8$: 435.2 (M+H)$^+$; found: 435.3 (M+H)$^+$.

Example 12

3-(7-amino-4-(4-methyloxazol-5-yl)-2-(pyridin-2-ylmethyl)-2H-pyrazolo[3,4-c]pyridin-5-yl)benzonitrile

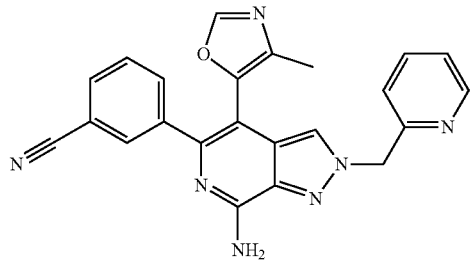

Step A. 4-methyl-5-(4,4,5,5-tetramethyl-1,3,2-dioxaborolan-2-yl)oxazole

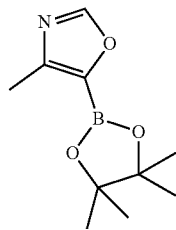

Under $N_2$ atmosphere, a flask was charged with [Ir(OMe)(1,5-cod)]$_2$ (33 mg, 0.050 mmol), 4,4,5,5-tetramethyl-1,3,2-dioxaborolane (0.22 mL, 1.50 mmol), and pentane (2.0 mL). The resulting mixture was stirred at room temperature for 10 to 15 min. 4,4'-Di-tert-butyl-2,2'-dipyridyl (dtbpy) (26.8 mg, 0.10 mmol) was added and the reaction mixture was stirred for an additional 20 minutes. 4-methyloxazole (83.1 mg, 1.0 mmol) in diethyl ether (2.0 mL) was then added and the resulting mixture was stirred at room temperature until completion. The solvent was removed under reduced pressure, and the crude material was washed with pentane to furnish the desired product. LC-MS calculated for $C_{10}H_{17}BNO_3$: 210.1 (M+H)+; found: 210.1 (M+H)+.

Step B. 3-(7-amino-4-(4-methyloxazol-5-yl)-2-(pyridin-2-ylmethyl)-2H-pyrazolo[3,4-c]pyridin-5-yl)benzonitrile

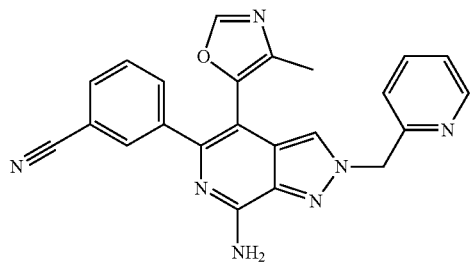

Cesium carbonate (80 mg, 0.247 mmol) was added to the mixture of 3-(7-amino-4-bromo-2-(pyridin-2-ylmethyl)-2H-pyrazolo[3,4-c]pyridin-5-yl)benzonitrile (50 mg, 0.123 mmol) and 4-methyl-5-(4,4,5,5-tetramethyl-1,3,2-dioxaborolan-2-yl)oxazole (25.8 mg, 0.123 mmol) in 1,4-dioxane (2.0 mL) and water (0.2 mL). The resulting mixture was sparged with $N_2$ for 2 min and chloro(2-dicyclohexylphosphino-2',4',6'-triisopropyl-1,1'-biphenyl)[2-(2'-amino-1,1'-biphenyl)]palladium(II)(9.71 mg, 0.012 mmol) was added. The reaction mixture was stirred at 120° C. under microwave irradiation for 90 min. The reaction mixture was diluted with methanol. Direct purification on prep. HPLC afforded the desired product. LC-MS calculated for $C_{23}H_{18}N_7O$: 408.2 $(M+H)^+$; found: 408.2 $(M+H)^+$.

Example 13

3-(7-amino-4-(4-methyloxazol-5-yl)-24(6-methylpyridin-2-yl)methyl)-2H-pyrazolo[3,4-c]pyridin-5-yl)benzonitrile

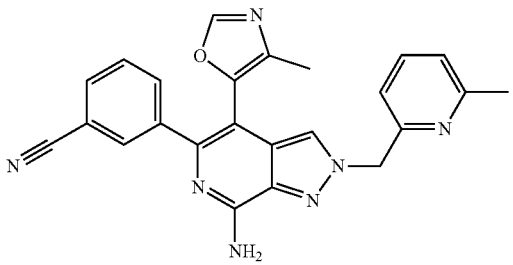

Cesium carbonate (78 mg, 0.239 mmol) was added to the mixture of 3-(7-amino-4-bromo-2-((6-methylpyridin-2-yl)methyl)-2H-pyrazolo[3,4-c]pyridin-5-yl)benzonitrile (50 mg, 0.119 mmol), 4-methyl-5-(4,4,5,5-tetramethyl-1,3,2-dioxaborolan-2-yl)oxazole (24.93 mg, 0.119 mmol) in 1,4-dioxane (2.0 ml) and water (0.2 ml) and then the reaction was sparged with $N_2$ for 2 min. After chloro(2-dicyclohexylphosphino-2',4',6'-triisopropyl-1,1'-biphenyl)[2-(2'-amino-1,1'-biphenyl)]palladium(II) (0.012 mmol) was added, the reaction was stirred at 120° C. for 1.5 h under microwave irradiation. The reaction mixture was diluted with methanol. Direct purification on prep. HPLC afforded the desired product. LC-MS calculated for $C_{24}H_{20}N_7O$: 422.2 $(M+H)^+$; found: 422.2 $(M+H)^+$.

Example 14

3-(7-amino-4-(1-ethyl-1H-pyrazol-5-yl)-2-((3-fluoropyridin-2-yl)methyl)-2H-pyrazolo[3,4-c]pyridin-5-yl)benzonitrile

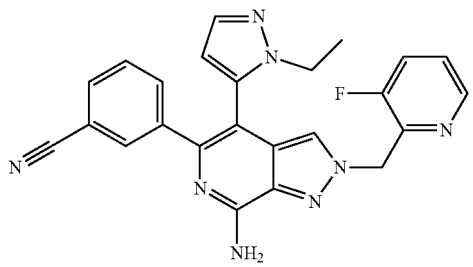

Step A. 5-chloro-N-(2,4-dimethoxybenzyl)-24(3-fluoropyridin-2-yl)methyl)-2H-pyrazolo[3,4-c]pyridin-7-amine

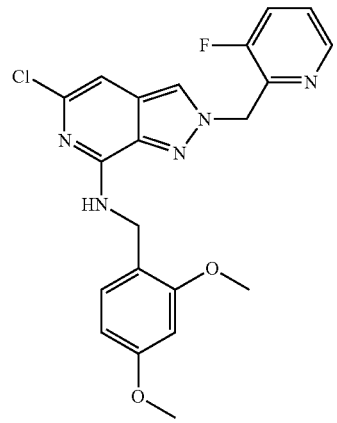 [SMILES: COc1ccc(CNc2nc(Cl)cc3cn(Cc4ncccc4F)nc23)c(OC)c1]

To the mixture of 5-chloro-N-(2,4-dimethoxybenzyl)-1H-pyrazolo[3,4-c]pyridin-7-amine (1000 mg, 3.14 mmol), (3-fluoropyridin-2-yl)methanol (0.379 mL, 3.76 mmol), and triphenylphosphine (1646 mg, 6.27 mmol) in DCM (15 mL) was added diisopropyl azodicarboxylate (0.741 mL, 3.76 mmol) at 0° C. The reaction mixture was stirred at 0° C. overnight. Direct purification on silica gel column afforded the desired product (477 mg, 36%). LC-MS calculated for $C_{21}H_{20}ClFN_5O_2$: 428.1 $(M+H)^+$; found: 428.2 $(M+H)^+$.

Step B. 3-(7-((2,4-dimethoxybenzyl)amino)-2-((3-fluoropyridin-2-yl)methyl)-2H-pyrazolo[3,4-c]pyridin-5-yl)benzonitrile

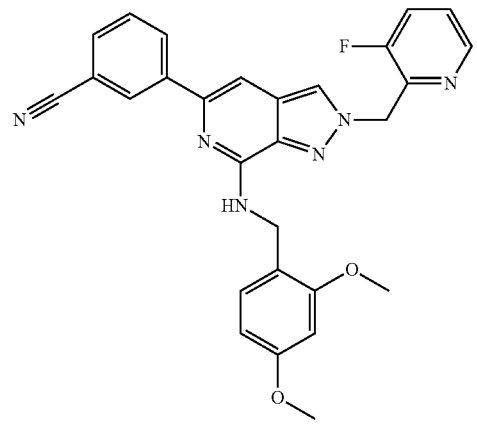

To the mixture of 5-chloro-N-(2,4-dimethoxybenzyl)-2-((3-fluoropyridin-2-yl)methyl)-2H-pyrazolo[3,4-c]pyridin-7-amine (1150 mg, 2.69 mmol) and (3-cyanophenyl)boronic acid (790 mg, 5.38 mmol) in 1,4-dioxane (10.0 mL) and water (1.00 mL) was added cesium carbonate (1751 mg, 5.38 mmol). The resulting mixture was sparged with $N_2$ for 2 min and chloro(2-dicyclohexylphosphino-2',4',6'-triisopropyl-1,1'-biphenyl)[2-(2'-amino-1,1'-biphenyl)]palladium (II)(211 mg, 0.269 mmol) was added. The reaction mixture was stirred at 120° C. under microwave irradiation for 90 minutes. The reaction was quenched with 20 mL of ethyl acetate and 20 mL of water. The organic phase was separated and the aqueous solution was extracted with ethyl acetate twice. The combined extracts were dried over $Na_2SO_4$, filtered and evaporated under reduced pressure. The residue was purified on silica gel column to afford the desired product, (647 mg, 49%). LC-MS calculated for $C_{28}H_{24}FN_6O_2$: 495.2 $(M+H)^+$; found: 495.2 $(M+H)^+$.

Step C. 3-(7-amino-2-((3-fluoropyridin-2-)methyl)-2H-pyrazolo[3,4-e]pyridin-5-yl)benzonitrile

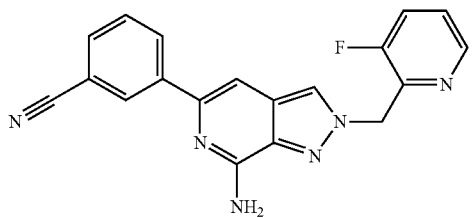

The solution of 3-(7-((2,4-dimethoxybenzypamino)-2-((3-fluoropyridin-2-yl)methyl)-2H-pyrazolo[3,4-c]pyridin-5-yl)benzonitrile (647.3 mg, 1.309 mmol, 48.7% yield) in TFA (5 mL) was stirred at 100° C. for 30 min. TFA was evaporated under reduced pressure and then 20 mL of saturated $NaHCO_3$ aqueous solution and 20 mL of ethyl acetate were added. The organic phase was separated and the aqueous solution was extracted with ethyl acetate twice. The combined extracts were dried over $Na_2SO_4$, filtered and evaporated under reduced pressure. The residue was purified on silica gel column to afford the desired product (374 mg, 83%). LC-MS calculated for $C_{19}H_{14}FN_6$: 345.1 $(M+H)^+$; found: 345.3 $(M+H)^+$.

Step D. 3-(7-amino-4-bromo-2-((3-fluoropyridin-2-)methyl)-2H-pyrazolo[3,4-c]pyridin-5-yl)benzonitrile

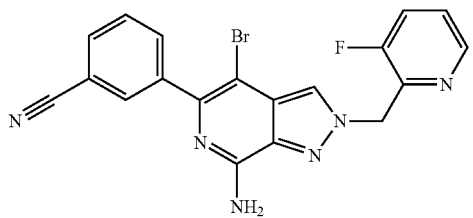 [SMILES: N#Cc1cccc(-c2nc(N)c3nn(Cc4ncccc4F)cc3c2Br)c1]

The mixture of 3-(7-amino-2-((3-fluoropyridin-2-yl)methyl)-2H-pyrazolo[3,4-c]pyridin-5-yl)benzonitrile (2000 mg, 5.81 mmol) and 1-bromopyrrolidine-2,5-dione (2067 mg, 11.62 mmol) in THF (10 mL) was stirred at 0° C. for 1 h. Direct purification on silica gel column afforded the desired product. LC-MS calculated for $C_{19}H_{13}BrFN_6$: 423.0 $(M+H)^+$ and 425.0 $(M+H)^+$; found: 423.0 $(M+H)^+$ and 425.0 $(M+H)^+$.

Step E. 3-(7-amino-4-(1-ethyl-1H-pyrazol-5-yl)-2-((3-fluoropyridin-2-)methyl)-2H-pyrazolo[3,4-e]pyridin-5-yl)benzonitrile

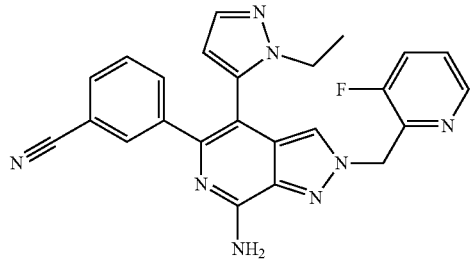 [SMILES: CCn1nccc1-c1c(-c2cccc(C#N)c2)nc(N)c2nn(Cc3ncccc3F)cc12]

Cesium carbonate (30.8 mg, 0.095 mmol) was added to the mixture of 3-(7-amino-4-bromo-2-((3-fluoropyridin-2-yl)methyl)-2H-pyrazolo[3,4-c]pyridin-5-yl)benzonitrile (20 mg, 0.047 mmol) and 1-ethyl-5-(4,4,5,5-tetramethyl-1,3,2-dioxaborolan-2-yl)-1H-pyrazole (10.49 mg, 0.047 mmol) in 1,4-dioxane (2.0 mL) and water (2 mL). The reaction was sparged with $N_2$ for 2 min and then chloro(2-dicyclohexylphosphino-2',4',6'-triisopropyl-1,1'-biphenyl)[2-(2'-amino-1,1'-biphenyl)]palladium(II) (4.73 µmol) was added. The resulting reaction mixture was stirred at 120° C. under microwave irradiation for 1.5 h. The reaction mixture was diluted with methanol. Direct purification on prep. HPLC afforded the desired product. LC-MS calculated for $C_{24}H_{20}FN_8$: 439.2 $(M+H)^+$; found: 439.3 $(M+H)^+$.

Example 15

3-(7-amino-2-((3-fluoropyridin-2-yl)methyl)-4-(pyrimidin-4-yl)-2H-pyrazolo[3,4-c]pyridin-5-yl)benzonitrile

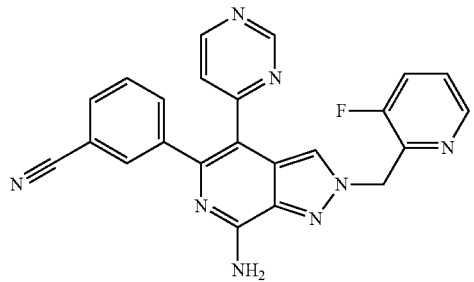

The mixture of 3-(7-amino-4-bromo-2-((3-fluoropyridin-2-yl)methyl)-2H-pyrazolo[3,4-c]pyridin-5-yl)benzonitrile (20 mg, 0.047 mmol), 4-(tributylstannyl)pyrimidine (52.3 mg, 0.142 mmol), copper(I) chloride (5.61 mg, 0.057 mmol), lithium chloride (2.404 mg, 0.057 mmol) and tetrakis(triphenylphosphine)palladium(0) (5.46 mg, 4.73 µmol) in THF (1 ml) was first purged with $N_2$, and then heated and stirred at 90° C. for 2 h. The reaction was diluted with methanol and purified with prep-LCMS (pH=2) to give the final desired product. LC-MS calculated for $C_{23}H_{16}FN_8$: 423.1 $(M+H)^+$; found: 423.3 $(M+H)^+$.

Example 16

3-(4-amino-2-(pyridin-2-ylmethyl)-7-(pyrimidin-4-yl)-2H-[1,2,3]triazolo[4,5-c]pyridin-6-yl)benzonitrile

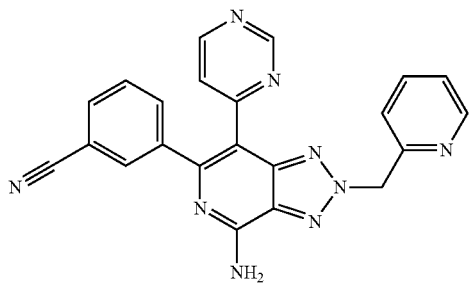

Step A. 4,6-dichloro-3H-[1,2,3]triazolo[4,5-c]pyridine

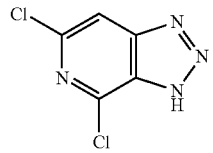 [SMILES: Clc1cc2nn[nH]c2c(Cl)n1]

A solution of NaNO$_2$ (3.88 g, 56.2 mmol) in water (3 mL) was added to a solution of 2,6-dichloropyridine-3,4-diamine (10 g, 56 mmol) in hydrochloric Acid, 37% (5 mL) at 0° C. The solution was stirred for 30 min. Water (20 mL) was added and the white precipitate was filtered, washed with water, and dried to give the desired product. LC-MS calculated for C$_5$H$_3$Cl$_2$N$_4$: 189.0 (M+H)$^+$; found: 189.0 (M+H)$^+$.

Step B. 6-chloro-N-(2,4-dimethoxybenzyl)-3H-[1,2,3]triazolo[4,5-c]pyridin-4-amine

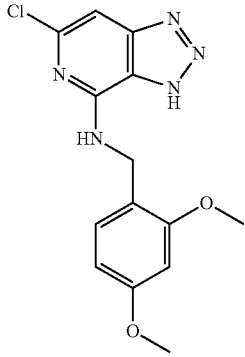 [SMILES: COc1ccc(CNc2nc(Cl)cc3nn[nH]c23)c(OC)c1]

The mixture of 4,6-dichloro-3H-[1,2,3]triazolo[4,5-c]pyridine (600 mg, 3.17 mmol), (2,4-dimethoxyphenyl)methanamine (0.53 mL1, 3.49 mmol) and triethylamine (0.53 mL, 3.81 mmol) in 1,4-dioxane (10 mL) was stirred at 110° C. for 3 days. Direct purification on silica gel column afforded the desired product (875 mg, 86%). LC-MS calculated for C$_{14}$H$_{15}$ClN$_5$O$_2$: 320.1 (M+H)$^+$; found: 320.3 (M+H)$^+$.

Step C. 6-chloro-N-(2,4-dimethoxybenzyl)-2-(pyridin-2-ylmethyl)-2H-[1,2,3]triazolo[4,5-c]pyridin-4-amine

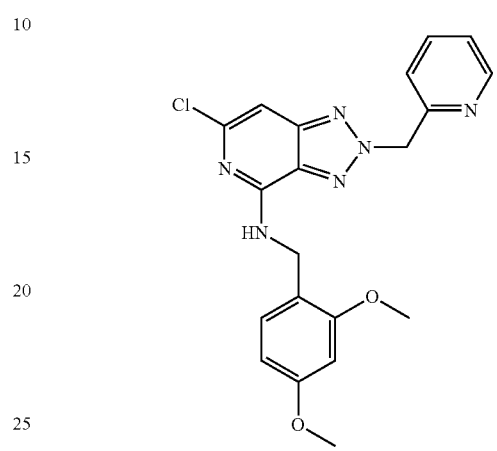

The mixture of 6-chloro-N-(2,4-dimethoxybenzyl)-3H-[1,2,3]triazolo[4,5-c]pyridin-4-amine (875 mg, 2.74 mmol), pyridin-2-ylmethanol (0.317 mL, 3.28 mmol) and triphenylphosphine (1436 mg, 5.47 mmol) in DCM (20 mL) was added diisopropyl azodicarboxylate (0.647 mL, 3.28 mmol) at 0° C. The resulting mixture was stirred at 0° C. for 1 h. Direct purification on silica gel column afforded the desired product (375 mg, 33.4% yield). LC-MS calculated for C$_{20}$H$_{20}$ClN$_6$O$_2$: 411.1 (M+H)$^+$; found: 411.2 (M+H)$^+$.

Step D. 3-(4-((2,4-dimethoxybenzyl)amino)-2-(pyridin-2-ylmethyl)-2H-[1,2,3]triazolo[4,5-c]pyridin-6-yl)benzonitrile

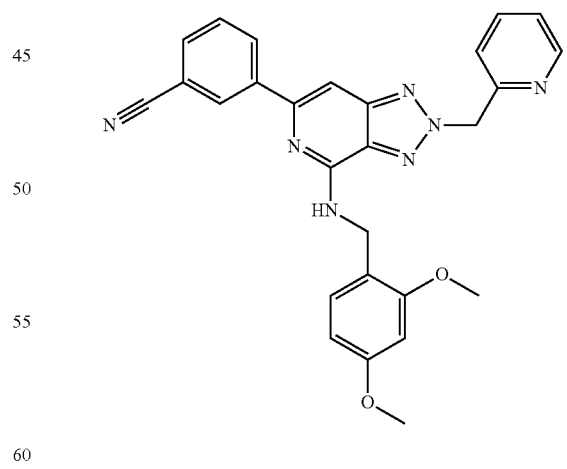

To the mixture of 6-chloro-N-(2,4-dimethoxybenzyl)-2-(pyridin-2-ylmethyl)-2H-[1,2,3]triazolo[4,5-c]pyridin-4-amine (375 mg, 0.913 mmol) and (3-cyanophenyl)boronic acid (268 mg, 1.825 mmol) in 1,4-dioxane (10 mL) and water (1.00 mL) was added cesium carbonate (595 mg, 1.825 mmol). The resulting mixture was purged with N$_2$ and then chloro(2-dicyclohexylphosphino-2',4',6'-tri is opropyl- 1,1'-biphenyl)[2-(2'-amino-1,1'-biphenyl)]palladium(II) (71.8 mg, 0.091 mmol) was added. The reaction mixture was stirred at 120° C. under microwave irradiation for 90 min. The reaction was quenched with 20 mL of ethyl acetate and 20 mL of water. The organic phase was separated and the aqueous solution was extracted with ethyl acetate twice. The combined extracts were dried over Na$_2$SO$_4$, filtered and evaporated under reduced pressure. The residue was purified on silica gel column to afford the desired product (300 mg, 68.9%). LC-MS calculated for C$_{27}$H$_{24}$N$_7$O$_2$: 478.2 (M+H)$^+$; found: 478.3 (M+H)$^+$.

Step E. 3-(4-amino-2-(pyridin-2-ylmethyl)-2H-[1,2,3]triazolo[4,5-c]pyridin-6-yl)benzonitrile

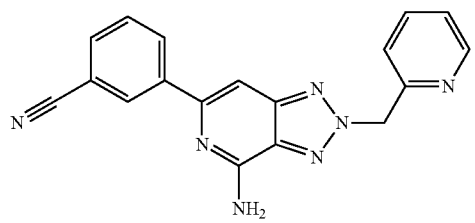

The solution of 3-(4-((2,4-dimethoxybenzyl)amino)-2-(pyridin-2-ylmethyl)-2H-[1,2,3]triazolo[4,5-c]pyridin-6-yl)benzonitrile (300.3 mg, 0.629 mmol) in TFA (5 mL) was stirred at 100° C. for 30 min. TFA was evaporated under reduced pressure and then 20 mL of saturated NaHCO$_3$ aqueous solution and 20 mL of ethyl acetate were added. The organic phase was separated and the aqueous solution was extracted with ethyl acetate twice. The combined extracts were dried over Na$_2$SO$_4$, filtered and evaporated under reduced pressure. The residue was purified on silica gel column to afford the desired product (175 mg, 85%). LC-MS calculated for C$_{18}$H$_{14}$N$_7$: 328.1 (M+H)$^+$; found: 328.2 (M+H)$^+$.

Step F. 3-(4-amino-7-bromo-2-(pyridin-2-ylmethyl)-2H-[1,2,3]triazolo[4,5-c]pyridin-6-yl)benzonitrile

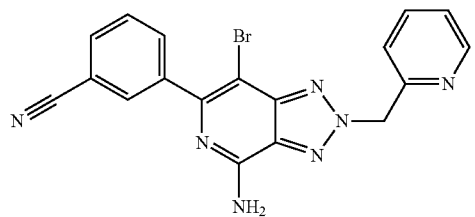

The mixture of 3-(4-amino-2-(pyridin-2-ylmethyl)-2H-[1,2,3]triazolo[4,5-c]pyridin-6-yl)benzonitrile (175 mg, 0.535 mmol) and 1-bromopyrrolidine-2,5-dione (100 mg, 0.561 mmol) in THF (10 mL) was stirred at 0° C. for 30 min and then quenched with saturated NaHCO$_3$ aqueous solution. The organic phase was separated, dried over Na$_2$SO$_4$, filtered and evaporated under reduced pressure. The resulting residue was purified on silica gel column to afforded the desired product (135 mg, 62.2%). LC-MS calculated for C$_{18}$H$_{13}$BrN$_7$: 406.0 (M+H)$^+$ and 408.0 (M+H)$^+$; found: 406.1 (M+H)$^+$ and 408.2 (M+H)$^+$.

Step G. 3-(4-amino-2-(pyridin-2-ylmethyl)-7-(pyrimidin-4-yl)-2H-[1,2,3]triazolo[4,5-c]pyridin-6-yl)benzonitrile

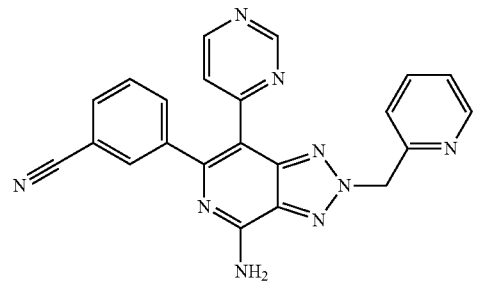

A mixture of 3-(4-amino-7-bromo-2-(pyridin-2-ylmethyl)-2H-[1,2,3]triazolo[4,5-c]pyridin-6-yl)benzonitrile (182 mg, 0.448 mmol), 4-(tributylstannyl)pyrimidine (496 mg, 1.344 mmol), and copper(I) chloride (53.2 mg, 0.538 mmol), lithium chloride (22.79 mg, 0.538 mmol) and tetrakis(triphenylphosphine)palladium(0) (51.8 mg, 0.045 mmol) in THF (1 ml) was first purged with N$_2$, and then heated and stirred at 90° C. for 2 h. The reaction was diluted with methanol and purified with prep-LCMS (pH=2) to give the desired product. LC-MS calculated for C$_{22}$H$_{16}$N$_9$: 406.2 (M+H)$^+$; found: 406.2 (M+H)$^+$.

Example 17

3-(4-amino-7-(4-methyloxazol-5-yl)-2-(pyridin-2-ylmethyl)-2H-[1,2,3]triazolo[4,5-c]pyridin-6-yl)benzonitrile

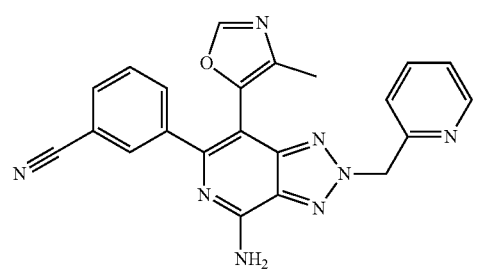

Cesium carbonate (30.8 mg, 0.095 mmol) was added to the mixture of 3-(4-amino-7-bromo-2-(pyridin-2-ylmethyl)-2H-[1,2,3]triazolo[4,5-c]pyridin-6-yl)benzonitrile (20 mg, 0.047 mmol) and 4-methyl-5-(4,4,5,5-tetramethyl-1,3,2-dioxaborolan-2-yl)oxazole (9.88 mg, 0.047 mmol) in 1,4-dioxane (2 mL) and water (0.2 mL). The reaction was sparged with N$_2$ for 2 min and chloro(2-dicyclohexylphosphino-2',4',6'-triisopropyl-1,1'-biphenyl)[2-(2'-amino-1,1'-biphenyl)]palladium(II) (3.5 mg, 4.73 µmol) was added. The reaction was stirred at 120° C. under microwave irradiation for 1.5 h. The mixture was diluted with methanol. Direct purification on prep. HPLC (pH=2) afforded the desired product. LC-MS calculated for C$_{22}$H$_{17}$N$_8$O: 409.2 (M+H)$^+$; found: 409.2 (M+H)$^+$.

Example 18

3-(4-amino-7-(1-ethyl-1H-pyrazol-5-yl)-2-(pyridin-2-ylmethyl)-2H-[1,2,3]triazolo[4,5-c]pyridin-6-yl)benzonitrile

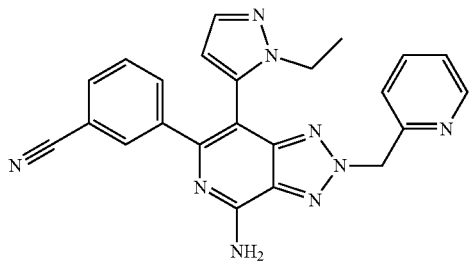 [SMILES: CCn1nccc1-c1c(-c2cccc(C#N)c2)nc(N)c2nn(Cc3ccccn3)nc12]

Cesium carbonate (292 mg, 0.896 mmol) was added to the mixture of 3-(4-amino-7-bromo-2-(pyridin-2-ylmethyl)-2H-[1,2,3]triazolo[4,5-c]pyridin-6-yl)benzonitrile (182 mg, 0.448 mmol) and (1-ethyl-1H-pyrazol-5-yl)boronic acid (62.7 mg, 0.448 mmol) in 1,4-dioxane (2 ml) and water (2 ml). The resulting reaction mixture was sparged with $N_2$ for 2 min and then chloro(2-dicyclohexylphosphino-2',4',6'-triisopropyl-1,1'-biphenyl)[2-(2'-amino-1,1'-biphenyl)]palladium(II) (0.045 mmol) was added. The reaction mixture was stirred at 120° C. for 1.5 h. The reaction mixture was diluted with methanol. Direct purification on prep. HPLC afforded the desired product. LC-MS calculated for $C_{23}H_{20}N_9$: 422.2 $(M+H)^+$; found: 422.3 $(M+H)^+$.

Example 19

3-(4-amino-7-(3-methylpyridin-4-yl)-2-(pyridin-2-ylmethyl)-2H-[1,2,3]triazolo[4,5-c]pyridin-6-yl)benzonitrile

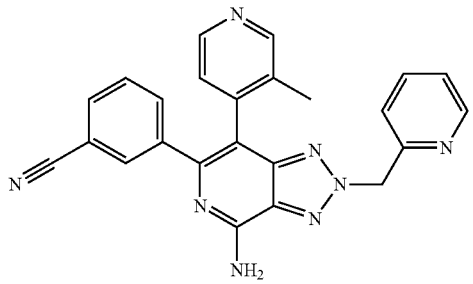 [SMILES: Cc1cnccc1-c1c(-c2cccc(C#N)c2)nc(N)c2nn(Cc3ccccn3)nc12]

The above title compound was synthesized according to the procedure described in Example 18, except by using (3-methylpyridin-4-yl)boronic acid instead of using (1-ethyl-1H-pyrazol-5-yl)boronic acid. LC-MS calculated for $C_{24}H_{19}N_8$: 419.2 $(M+H)^+$; found: 419.3 $(M+H)^+$.

Example 20

3-(4-amino-7-(4-(hydroxymethyl)-2-methyloxazol-5-yl)-2-(pyridin-2-ylmethyl)-2H-[1,2,3]triazolo[4,5-c]pyridin-6-yl)benzonitrile

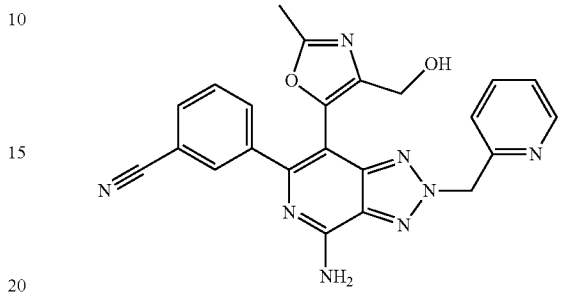

Cesium carbonate (80 mg, 0.246 mmol) was added to a mixture of 3-(4-amino-7-bromo-2-(pyridin-2-ylmethyl)-2H-[1,2,3]triazolo[4,5-c]pyridin-6-yl)benzonitrile (50 mg, 0.123 mmol) and (4-(((tert-butyldimethylsilyl)oxy)methyl)-2-methyloxazol-5-yl)boronic acid (66.8 mg, 0.246 mmol) in 1,4-dioxane (2.0 mL) and water (0.2 ml). The reaction was sparged with $N_2$ for 1 min and chloro(2-dicyclohexylphosphino-2',4',6'-triisopropyl-1,1'-biphenyl)[2-(2'-amino-1,1'-biphenyl)]palladium(II)(0.012 mmol) was added. The reaction was stirred at 120° C. for 1.5 h. TFA (1.0 ml, 12.98 mmol) was added and the reaction mixture was stirred at 100° C. for 60 min. The mixture was diluted with methanol. Direct purification on prep. HPLC afforded the desired product. LC-MS calculated for $C_{23}H_{19}N_8O_2$: 439.2 $(M+H)^+$; found: 439.3 $(M+H)^+$.

Example 21

3-(4-amino-7-(oxazol-5-yl)-2-(pyridin-2-ylmethyl)-2H-[1,2,3]triazolo[4,5-c]pyridin-6-yl)benzonitrile

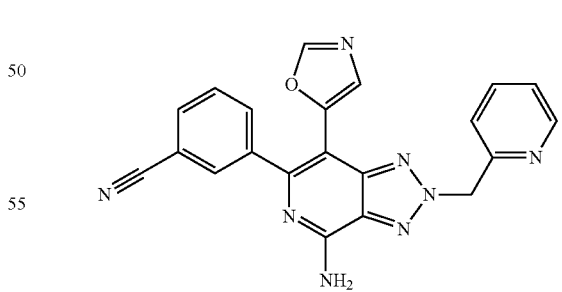

The above title compound was synthesized according to the procedure described in Example 18, except by using oxazol-5-ylboronic acid instead of using (1-ethyl-1H-pyrazol-5-yl)boronic acid. LC-MS calculated for $C_{21}H_{15}N_8O$: 395.1 $(M+H)^+$; found: 395.3 $(M+H)^+$.

Example 22

3-(4-amino-2-(pyridin-2-ylmethyl)-7-(quinolin-6-yl)-2H-[1,2,3]triazolo[4,5-c]pyridin-6-yl)benzonitrile

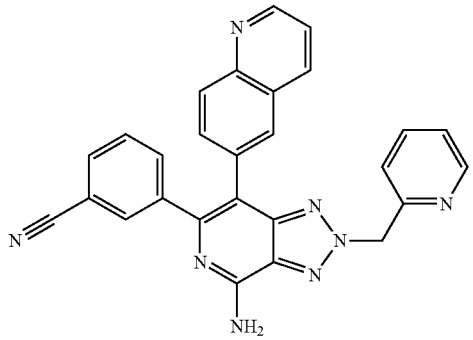

The above title compound was synthesized according to the procedure described in Example 18, except by using quinolin-6-ylboronic acid instead of using (1-ethyl-1H-pyrazol-5-yl)boronic acid. LC-MS calculated for $C_{27}H_{19}N_8$: 455.2 (M+H)$^+$; found: 455.3 (M+H)$^+$.

Example 23

3-(4-amino-2-(pyridin-2-ylmethyl)-7-(quinoxalin-6-yl)-2H-[1,2,3]triazolo[4,5-c]pyridin-6-yl)benzonitrile

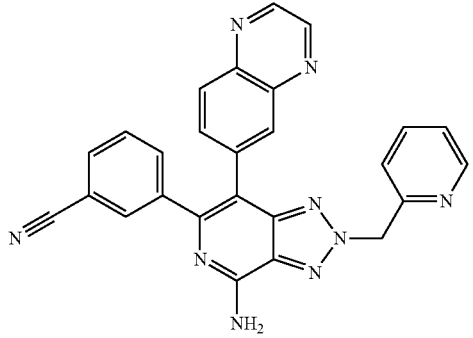

The above title compound was synthesized according to the procedure described in Example 18, except by using quinoxalin-6-ylboronic acid instead of using (1-ethyl-1H-pyrazol-5-yl)boronic acid. LC-MS calculated for $C_{26}H_{18}N_9$: 456.2 (M+H)$^+$; found: 456.3 (M+H)$^+$.

Example 24

3-(4-amino-2-((6-methylpyridin-2-yl)methyl)-7-(pyrimidin-4-yl)-2H-[1,2,3]triazolo[4,5-c]pyridin-6-yl)benzonitrile

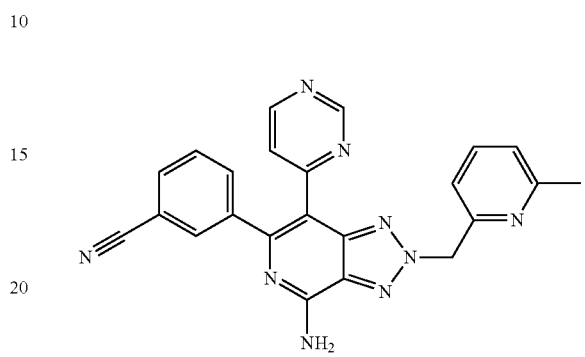

Step A. 6-chloro-N-(2,4-dimethoxybenzyl)-N-(4-methoxybenzyl)-3H-[1,2,3]triazolo[4,5-c]pyridin-4-amine

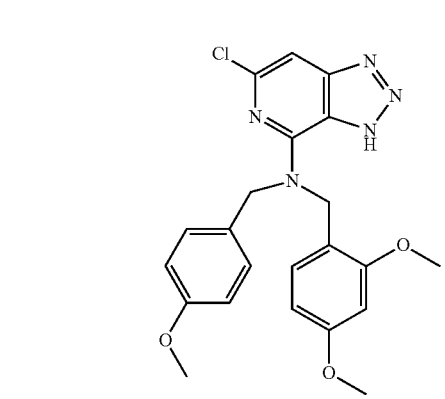 [SMILES: COc1ccc(CN(Cc2ccc(OC)cc2OC)c2nc(Cl)cc3nn[nH]c23)cc1]

The mixture of 4,6-dichloro-3H-[1,2,3]triazolo[4,5-c]pyridine (600 mg, 3.17 mmol), bis(4-methoxybenzyl)amine (899 mg, 3.49 mmol) and triethylamine (531 μl 3.81 mmol) in 1,4-dioxane (1.7 mL) was stirred at 110° C. for 3 days. Direct purification on silica gel column afforded the desired product (875 mg, 63%). LC-MS calculated for $C_{22}H_{23}ClN_5O_3$: 440.1 (M+H)$^+$; found: 440.3 (M+H)$^+$.

Step B. 6-chloro-N,N-bis(4-methoxybenzyl)-2-((6-methylpyridin-2-)methyl)-2H-[1,2,3]triazolo[4,5-e]pyridin-4-amine

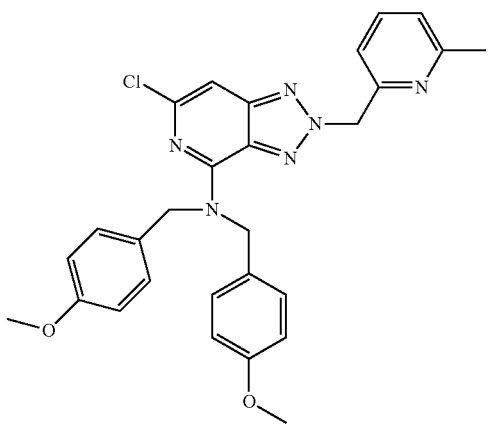

To the mixture of 6-chloro-N,N-bis(4-methoxybenzyl)-3H-[1,2,3]triazolo[4,5-c]pyridin-4-amine (875 mg, 2.135 mmol), (6-methylpyridin-2-yl)methanol (315 mg, 2.56 mmol) and triphenylphosphine (1120 mg, 4.27 mmol) in DCM (20 mL) was added diisopropyl azodicarboxylate (0.504 mL, 2.56 mmol) at 0° C. The reaction mixture was stirred at 0° C. overnight. Direct purification on silica gel afforded the desired product (353 mg, 32%). LC-MS calculated for $C_{28}H_{28}ClN_6O_2$: 515.2 $(M+H)^+$; found: 515.2 $(M+H)^+$.

Step C. 3-(4-(bis(4-methoxybenzyl)amino)-2-((6-methylpyridin-2-yl)methyl)-2H-[1,2,3]triazolo[4,5-e]pyridin-6-yl)benzonitrile

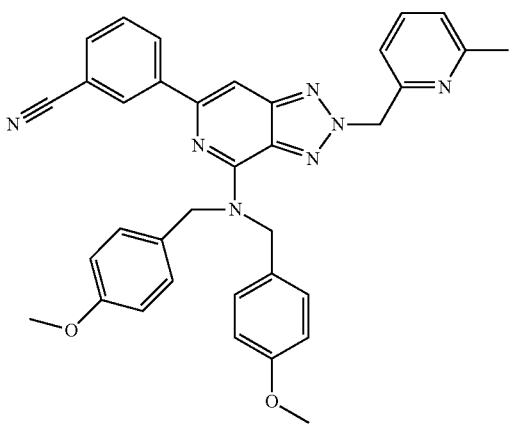 [SMILES: COc1ccc(CN(Cc2ccc(OC)cc2)c2nc(-c3cccc(C#N)c3)cc3nn(Cc4cccc(C)n4)nc23)cc1]

Cesium carbonate (447 mg, 1.371 mmol) was added to the mixture of 6-chloro-N,N-bis(4-methoxybenzyl)-2-((6-methylpyridin-2-yl)methyl)-2H-[1,2,3]triazolo[4,5-c]pyridin-4-amine (353 mg, 0.685 mmol) and (3-cyanophenyl)boronic acid (201 mg, 1.371 mmol) in 1,4-dioxane (10 mL) and water (1.00 mL). The resulting reaction mixture was sparged with $N_2$ for 2 min. Chloro(2-dicyclohexylphosphino-2',4',6'-triisopropyl-1,1'-biphenyl)[2-(2'-amino-1,1'-biphenyl)]palladium(II) (53.9 mg, 0.069 mmol) was added. The reaction was stirred at 120° C. under microwave irradiation for 1.5 h. The reaction was quenched with 20 mL of ethyl acetate and 20 mL of water. The organic phase was separated and the aqueous solution was extracted with ethyl acetate twice. The combined extracts were dried over $Na_2SO_4$, filtered and evaporated under reduced pressure. The residue was purified on silica gel column to afford the desired product (280 mg, 70.3%). LC-MS calculated for $C_{35}H_{32}N_7O_2$: 582.3 $(M+H)^+$; found: 582.3 $(M+H)^+$.

Step D. 3-(4-amino-2-((6-methylpyridin-2-yl)methyl)-2H-[1,2,3]triazolo[4,5-c]pyridin-6-yl)benzonitrile

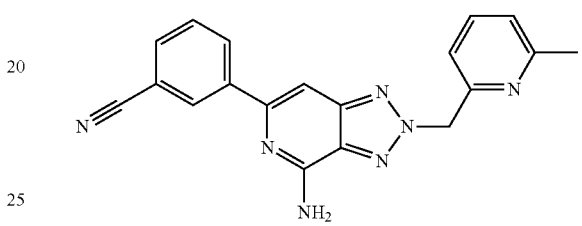

The solution of 3-(4-(bis(4-methoxybenzyl)amino)-2-((6-methylpyridin-2-yl)methyl)-2H-[1,2,3]triazolo[4,5-c]pyridin-6-yl)benzonitrile (280.3 mg, 0.482 mmol,) in TFA (5 mL) was stirred at 100° C. for 1 h. TFA was evaporated under reduced pressure and then 20 mL of saturated $NaHCO_3$ aqueous solution and 20 mL of ethyl acetate were added. The organic phase was separated and the aqueous solution was extracted with ethyl acetate twice. The combined extracts were dried over $Na_2SO_4$, filtered and evaporated under reduced pressure. The residue was purified on silica gel column to afford the desired product (136 mg, 58%). LC-MS calculated for $C_{19}H_{16}N_7$: 342.1 $(M+H)^+$; found: 342.3 $(M+H)^+$.

Step E. 3-(4-amino-7-bromo-2-((6-methylpyridin-2-yl)methyl)-2H-[1,2,3]triazolo[4,5-c]pyridin-6-yl)benzonitrile

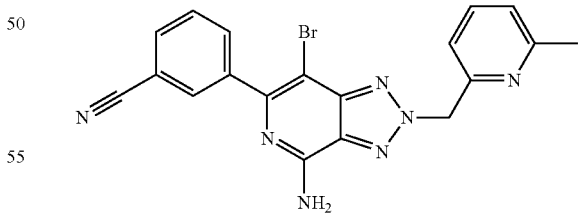

The mixture of 3-(4-amino-2-((6-methylpyridin-2-yl)methyl)-2H-[1,2,3]triazolo[4,5-c]pyridin-6-yl)benzonitrile (136 mg, 0.398 mmol) and 1-bromopyrrolidine-2,5-dione (142 mg, 0.797 mmol) in THF (10 mL) was stirred at 0° C. for 1 h. Direct purification on silica gel afforded the desired product (133 mg, 79%). LC-MS calculated for $C_{19}H_{15}BrN_7$: 420.1 $(M+H)^+$ and 422.1 $(M+H)^+$; found: 420.1 $(M+H)^+$ and 422.2 $(M+H)^+$.

Step F. 3-(4-amino-24(6-methylpyridin-2-yl) methyl)-7-(pyrimidin-4-yl)-2H-[1,2,3]triazolo[4,5-c] pyridin-6-yl)benzonitrile

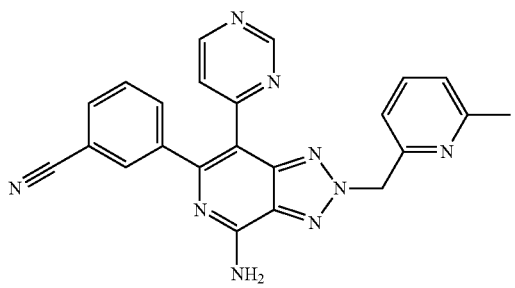 [SMILES: Cc1cccc(Cn2nc3c(N)nc(-c4cccc(C#N)c4)c(-c4ccncn4)c3n2)n1]

The mixture of 3-(4-amino-7-bromo-2-((6-methylpyridin-2-yl)methyl)-2H-[1,2,3]triazolo[4,5-c]pyridin-6-yl)benzonitrile (182 mg, 0.433 mmol), 4-(tributylstannyl)pyrimidine (480 mg, 1.299 mmol), and copper(I) chloride (51.4 mg, 0.520 mmol), lithium chloride (22.03 mg, 0.520 mmol) and tetrakis(triphenylphosphine)palladium(0) (50.0 mg, 0.043 mmol) in THF (1 ml) was first purged with $N_2$, and then heated and stirred at 90° C. for 2 h. The reaction was diluted with methanol and purified with prep-LCMS (pH=2) to give the desired product. LC-MS calculated for $C_{23}H_{18}N_9$: 420.2 $(M+H)^+$; found: 420.3 $(M+H)^+$.

Example 25

3-(4-amino-2-((6-methylpyridin-2-yl)methyl)-7-(pyridin-4-yl)-2H-[1,2,3]triazolo[4,5-c]pyridin-6-yl)benzonitrile

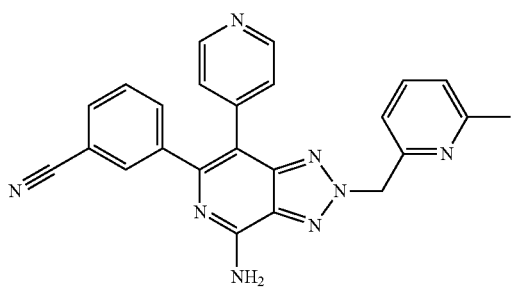

Cesium carbonate (78 mg, 0.238 mmol) was added to the mixture of 3-(4-amino-7-bromo-2-((6-methylpyridin-2-yl)methyl)-2H-[1,2,3]triazolo[4,5-c]pyridin-6-yl)benzonitrile (50 mg, 0.119 mmol) and pyridin-4-ylboronic acid (14.62 mg, 0.119 mmol) in 1,4-dioxane (2.0 mL) and water (0.2 mL). The resulting mixture was sparged with $N_2$ for 25 min and chloro(2-dicyclohexylphosphino-2',4',6'-triisopropyl-1,1'-biphenyl)[2-(2'-amino-1,1'-biphenyl)]palladium(II) (9.36 mg, 0.012 mmol) was added. The reaction was stirred at 120° C. for 1.5 h under microwave irradiation. The reaction mixture was diluted with methanol. Direct purification on prep. HPLC afforded the desired product. LC-MS calculated for $C_{24}H_{19}N_8$: 419.2 $(M+H)^+$; found: 419.3 $(M+H)^+$.

Example 26

3-(4-amino-2-((6-methylpyridin-2-yl)methyl)-7-(3-methylpyridin-4-yl)-2H-[1,2,3]triazolo[4,5-c]pyridin-6-yl)benzonitrile

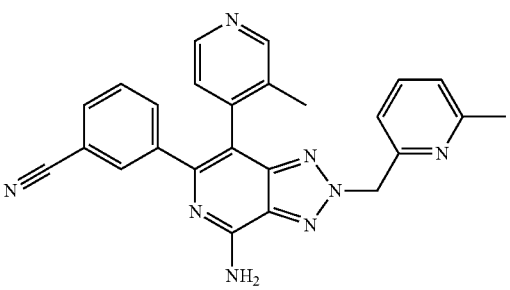 [SMILES: Cc1cccc(Cn2nc3c(N)nc(-c4cccc(C#N)c4)c(-c4ccncc4C)c3n2)n1]

The above title compound was synthesized according to the procedure described in Example 25, except by using (3-methylpyridin-4-yl)boronic acid instead of using pyridin-4-ylboronic acid. LC-MS calculated for $C_{25}H_{21}N_8$: 433.2 $(M+H)^+$; found: 433.3 $(M+H)^+$.

Example 27

3-(4-amino-7-(1-methyl-6-oxo-1,6-dihydropyridin-3-yl)-2-((6-methylpyridin-2-yl)methyl)-2H-[1,2,3]triazolo[4,5-c]pyridin-6-yl)benzonitrile

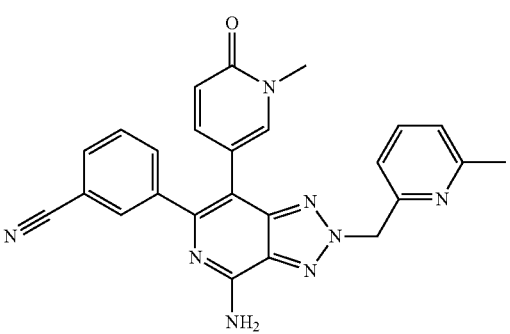 [SMILES: Cc1cccc(Cn2nc3c(N)nc(-c4cccc(C#N)c4)c(-c4ccc(=O)n(C)c4)c3n2)n1]

The above title compound was synthesized according to the procedure described in Example 25, except by using (1-methyl-6-oxo-1,6-dihydropyridin-3-yl)boronic acid instead of using pyridin-4-ylboronic acid. LC-MS calculated for $C_{25}H_{21}N_8O$: 449.2 $(M+H)^+$; found: 449.3 $(M+H)^+$.

Example 28

3-(4-amino-7-(1-ethyl-1H-pyrazol-5-yl)-2-((6-methylpyridin-2-yl)methyl)-2H-[1,2,3]triazolo[4,5-c]pyridin-6-yl)benzonitrile

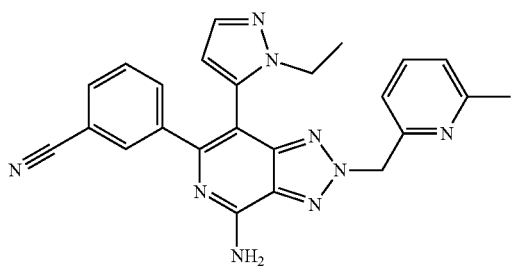 [SMILES: CCn1nccc1-c1c(-c2cccc(C#N)c2)nc(N)c2nn(Cc3cccc(C)n3)nc12]

The above title compound was synthesized according to the procedure described in Example 25, except by using (1-ethyl-1H-pyrazol-5-yl)boronic acid instead of using pyridin-4-ylboronic acid. LC-MS calculated for $C_{24}H_{22}N_9$: 436.2 $(M+H)^+$; found: 436.3 $(M+H)^+$.

Example 29

3-(4-amino-7-(4-methyloxazol-5-yl)-2-((6-methylpyridin-2-yl)methyl)-2H-[1,2,3]triazolo[4,5-c]pyridin-6-yl)benzonitrile

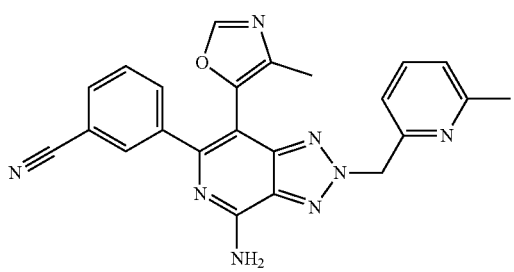 [SMILES: Cc1cccc(Cn2nc3c(N)nc(-c4cccc(C#N)c4)c(-c4ocnc4C)c3n2)n1]

The above title compound was synthesized according to the procedure described in Example 25, except by using 4-methyl-5-(4,4,5,5-tetramethyl-1,3,2-dioxaborolan-2-yl) oxazole instead of using pyridin-4-ylboronic acid. LC-MS calculated for $C_{23}H_{19}N_8O$: 423.2 $(M+H)^+$; found: 423.3 $(M+H)^+$.

Example 30

3-(4-amino-2-((3-fluoropyridin-2-yl)methyl)-7-(pyrimidin-4-yl)-2H-[1,2,3]triazolo[4,5-c]pyridin-6-yl)benzonitrile

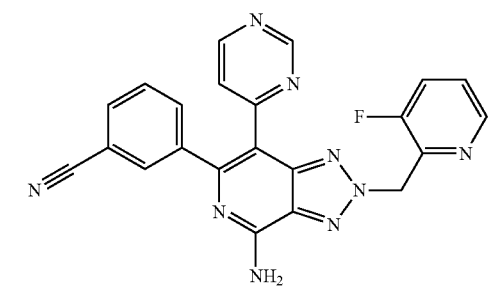

Step A. 6-chloro-N-(2,4-dimethoxybenzyl)-2-((3-fluoropyridin-2-yl)methyl)-2H-[1,2,3]triazolo[4,5-c]pyridin-4-amine

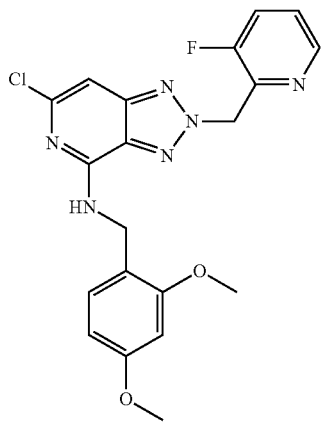 [SMILES: COc1ccc(CNc2nc(Cl)cc3nn(Cc4ncccc4F)nc23)c(OC)c1]

To the mixture of 6-chloro-N-(2,4-dimethoxybenzyl)-3H-[1,2,3]triazolo[4,5-c]pyridin-4-amine (1000 mg, 3.13 mmol), (3-fluoropyridin-2-yl)methanol (477 mg, 3.75 mmol) and triphenylphosphine (1641 mg, 6.25 mmol) in DCM (1.7 mL) was added diisopropyl azodicarboxylate (739 µl, 3.75 mmol) at 0° C. The reaction mixture was stirred at 0° C. for 1 h. Direct purification on silica gel column afforded the desired product (433 mg, 32%). LC-MS calculated for $C_{20}H_{19}ClFN_6O_2$: 429.1 $(M+H)^+$; found: 429.3 $(M+H)^+$.

Step B. 3-(4-((2,4-dimethoxybenzyl)amino)-2-((3-fluoropyridin-2-yl)methyl)-2H-[1,2,3]triazolo[4,5-c]pyridin-6-yl)benzonitrile

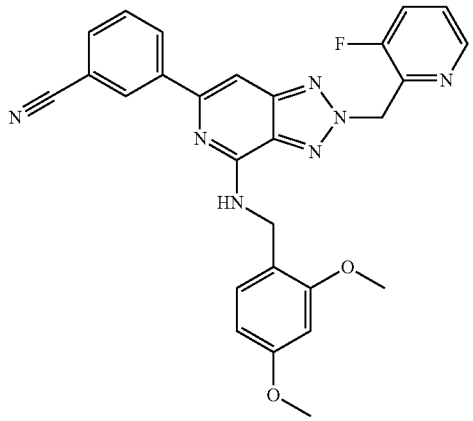

Cesium carbonate (658 mg, 2.019 mmol) was added to the mixture of 6-chloro-N-(2,4-dimethoxybenzyl)-2-((3-fluoropyridin-2-yl)methyl)-2H-[1,2,3]triazolo[4,5-c]pyridin-4-amine (433 mg, 1.010 mmol) and (3-cyanophenyl)boronic acid (297 mg, 2.019 mmol) in 1,4-dioxane (10.0 mL) and water (1.0 mL). The resulting mixture was sparged with $N_2$ for 2 min and (SP-4-4)-[2'-Amino[1,1'-biphenyl]-2-yl]chloro[dicyclohexyl[2',4',6'-tris(1-methylethyl)[1,1'-biphenyl]-2-yl]phosphine]palladium (79 mg, 0.101 mmol) was added. The reaction mixture was stirred at 120° C. for 1.5 h under microwave irradiation. The reaction was quenched with 20 mL of ethyl acetate and 20 mL of water. The organic phase was separated and the aqueous solution was extracted with ethyl acetate twice. The combined extracts were dried over $Na_2SO_4$, filtered and evaporated under reduced pressure. The residue was purified on silica gel column to afford the desired product (357 mg, 71%). LC-MS calculated for $C_{27}H_{23}FN_7O_2$: 496.2 $(M+H)^+$; found: 496.3 $(M+H)^+$.

Step C. 3-(4-amino-2-((3-fluoropyridin-2-yl)methyl)-2H-[1,2,3]triazolo[4,5-c]pyridin-6-yl)benzonitrile

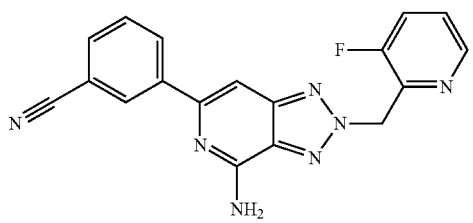 [SMILES: N#Cc1cccc(-c2cc3nn(Cc4ncccc4F)nc3c(N)n2)c1]

The solution of 3-(4-((2,4-dimethoxybenzyl)amino)-2-((3-fluoropyridin-2-yl)methyl)-2H-[1,2,3]triazolo[4,5-c]pyridin-6-yl)benzonitrile (357.3 mg, 0.721 mmol) in TFA (5 mL) was stirred at 100° C. for 1 h. TFA was evaporated under reduced pressure and then 20 mL of saturated $NaHCO_3$ aqueous solution and 20 mL of ethyl acetate were added. The organic phase was separated and the aqueous solution was extracted with ethyl acetate twice. The combined extracts were dried over $Na_2SO_4$, filtered and evaporated under reduced pressure. The residue was purified on silica gel column to afford the desired product (213 mg, 61%). LC-MS m/z calculated for $C_{18}H_{13}FN_7$: 346.1 $(M+H)^+$; found: 346.3 $(M+H)^+$.

Step D. 3-(4-amino-7-bromo-2-((3-fluoropyridin-2-)methyl)-2H-[1,2,3]triazolo[4,5-c]pyridin-6-yl)benzonitrile

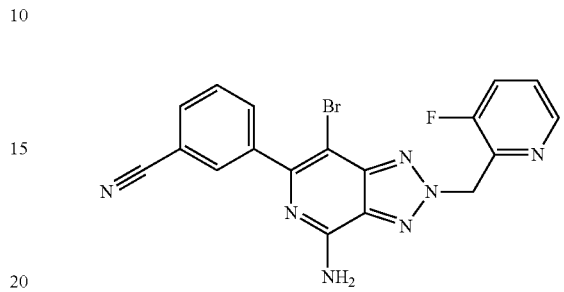

The mixture of 3-(4-amino-2-((3-fluoropyridin-2-yl)methyl)-2H-[1,2,3]triazolo[4,5-c]pyridin-6-yl)benzonitrile (213 mg, 0.617 mmol) and 1-bromopyrrolidine-2,5-dione (220 mg, 1.234 mmol) in THF (5 mL) was stirred at 0° C. for 1 h. Direct purification on silica gel afforded the desired product (175 mg, 67%). LC-MS calculated for $C_{18}H_{12}BrFN_7$: 424.0 $(M+H)^+$ and 426.0 $(M+H)^+$; found: 424.3 $(M+H)^+$ and 426.3 $(M+H)^+$.

Step E. 3-(4-amino-2-((3-fluoropyridin-2-yl)methyl)-7-(pyrimidin-4-yl)-2H-[1,2,3]triazolo[4,5-c]pyridin-6-yl)benzonitrile

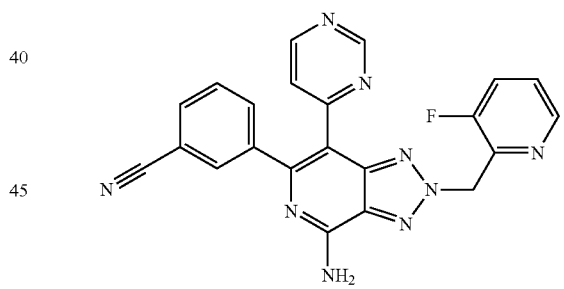

The mixture of 3-(4-amino-7-bromo-2-((3-fluoropyridin-2-yl)methyl)-2H-[1,2,3]triazolo[4,5-c]pyridin-6-yl)benzonitrile (220 mg, 0.519 mmol), 4-(tributylstannyl)pyrimidine (383 mg, 1.037 mmol), and copper(I) chloride (61.6 mg, 0.622 mmol), lithium chloride (26.4 mg, 0.622 mmol) and tetrakis(triphenylphosphine)palladium(0) (59.9 mg, 0.052 mmol) in THF (1 mL) was first purged with $N_2$, and then heated and stirred at 90° C. for 2 h. The reaction was diluted with methanol and purified with prep-LCMS (pH=2) to give the desired product. $^1H$ NMR (500 MHz, DMSO-$d_6$) ppm 8.98 (s, 1H), 8.77 (d, J=5.02 Hz, 1H), 8.38 (dd, $J_1$=4.60 Hz, $J_2$=1.32 Hz, 1H), 7.90-8.30 (bs, 2H), 7.76-7.89 (m, 3H), 7.66 (dd, $J_1$=5.25 Hz, $J_2$=1.25 Hz, 1H), 7.45-7.58 (m, 3H), 6.25 (s, 2H). LC-MS calculated for $C_{22}H_{15}FN_9$: 424.1 $(M+H)^+$; found: 424.3 $(M+H)^+$.

Example 31

3-(4-amino-2-((3-fluoropyridin-2-yl)methyl)-7-(pyridin-4-yl)-2H-[1,2,3]triazolo[4,5-c]pyridin-6-yl)benzonitrile

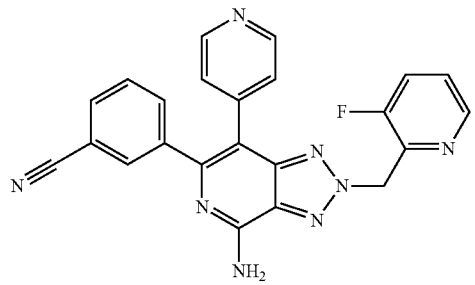 [SMILES: N#Cc1cccc(-c2nc(N)c3nn(Cc4ncccc4F)nc3c2-c2ccncc2)c1]

Cesium carbonate (46.1 mg, 0.141 mmol) was added to the mixture of 3-(4-amino-7-bromo-2-((3-fluoropyridin-2-yl)methyl)-2H-[1,2,3]triazolo[4,5-c]pyridin-6-yl)benzonitrile (30 mg, 0.071 mmol) and pyridin-4-ylboronic acid (17.38 mg, 0.141 mmol) in 1,4-dioxane (2 mL) and water (0.2 mL). The resulting mixture was sparged with $N_2$ for 2 min and chloro(2-dicyclohexylphosphino-2',4',6'-triisopropyl-1,1'-biphenyl)[2-(2'-amino-1,1'-biphenyl)]palladium(II) (5.56 mg, 7.07 μmol) was added. The reaction mixture was stirred at 120° C. for 1.5 h under microwave irradiation. The reaction mixture was diluted with methanol. Direct purification on pre. HPLC afforded the desired product. LC-MS calculated for $C_{23}H_{16}FN_8$: 423.1 $(M+H)^+$; found: 423.3 $(M+H)^+$.

Example 32

3-(4-amino-2-((3-fluoropyridin-2-yl)methyl)-7-(1-methyl-6-oxo-1,6-dihydropyridin-3-yl)-2H-[1,2,3]triazolo[4,5-c]pyridin-6-yl)benzonitrile

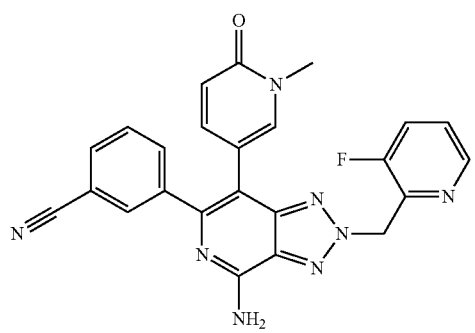 [SMILES: Cn1cc(-c2c(-c3cccc(C#N)c3)nc(N)c3nn(Cc4ncccc4F)nc23)ccc1=O]

The above title compound was synthesized according to the procedure described in Example 31, except by using (1-methyl-6-oxo-1,6-dihydropyridin-3-yl)boronic acid instead of using pyridin-4-ylboronic acid. LC-MS calculated for $C_{24}H_{18}FN_8O$: 453.2 $(M+H)^+$; found: 453.3 $(M+H)^+$.

Example 33

3-(4-amino-7-(1-ethyl-1H-pyrazol-5-yl)-2-((3-fluoropyridin-2-yl)methyl)-2H-[1,2,3]triazolo[4,5-c]pyridin-6-yl)benzonitrile

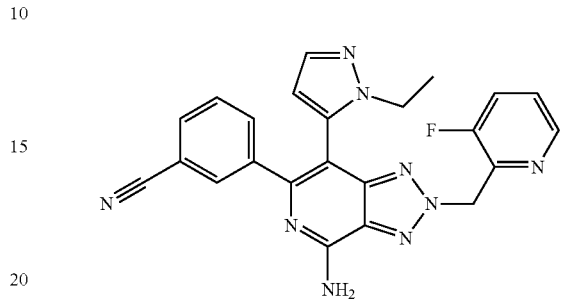

The above title compound was synthesized according to the procedure described in Example 31, except by using (1-ethyl-1H-pyrazol-5-yl)boronic acid instead of using pyridin-4-ylboronic acid. LC-MS calculated for $C_{23}H_{19}FN_9$: 440.2 $(M+H)^+$; found: 440.3 $(M+H)^+$.

Example 34

3-(4-amino-2-((3-fluoropyridin-2-yl)methyl)-7-(1-isopropyl-1H-pyrazol-5-yl)-2H-[1,2,3]triazolo[4,5-c]pyridin-6-yl)benzonitrile

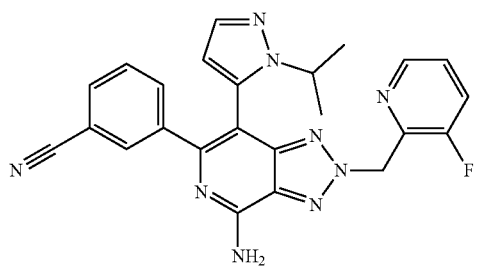 [SMILES: CC(C)n1nccc1-c1c(-c2cccc(C#N)c2)nc(N)c2nn(Cc3ncccc3F)nc12]

The above title compound was synthesized according to the procedure described in Example 31, except by using (1-isopropyl-1H-pyrazol-5-yl)boronic acid instead of using pyridin-4-ylboronic acid. LC-MS calculated for $C_{24}H_{21}FN_9$: 454.2 $(M+H)^+$; found: 454.3 $(M+H)^+$.

Example 35

3-(4-amino-2-((3-fluoropyridin-2-yl)methyl)-7-(1-methyl-1H-pyrazol-5-yl)-2H-[1,2,3]triazolo[4,5-c]pyridin-6-yl)benzonitrile

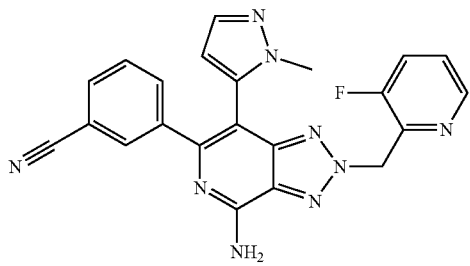 [SMILES: Cn1nccc1-c1c(-c2cccc(C#N)c2)nc(N)c2nn(Cc3ncccc3F)nc12]

The above title compound was synthesized according to the procedure described in Example 31, except by using (1-methyl-1H-pyrazol-5-yl)boronic acid instead of using pyridin-4-ylboronic acid. LC-MS calculated for $C_{22}H_{17}FN_9$: 426.2 $(M+H)^+$; found: 426.3 $(M+H)^+$.

Example 36

3-(4-amino-2-((3-fluoropyridin-2-yl)methyl)-7-(4-methyloxazol-5-yl)-2H-[1,2,3]triazolo[4,5-c]pyridin-6-yl)benzonitrile

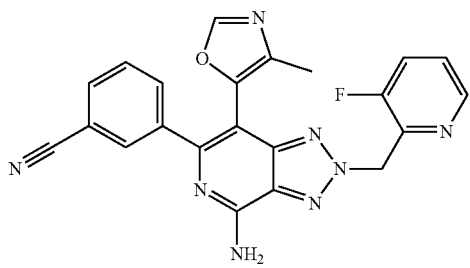 [SMILES: Cc1ncoc1-c1c(-c2cccc(C#N)c2)nc(N)c2nn(Cc3ncccc3F)nc12]

The above title compound was synthesized according to the procedure described in Example 31, except by using 4-methyl-5-(4,4,5,5-tetramethyl-1,3,2-dioxaborolan-2-yl)oxazole instead of using pyridin-4-ylboronic acid. LC-MS calculated for $C_{22}H_{16}FN_8O$: 427.1 $(M+H)^+$; found: 427.3 $(M+H)^+$.

Example 37

3-(4-amino-2-((3-fluoropyridin-2-yl)methyl)-7-(quinoxalin-6-yl)-2H-[1,2,3]triazolo[4,5-c]pyridin-6-yl)benzonitrile

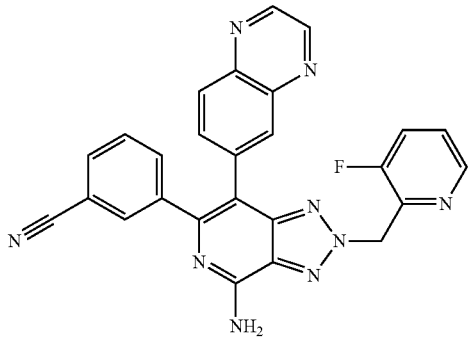 [SMILES: N#Cc1cccc(-c2nc(N)c3nn(Cc4ncccc4F)nc3c2-c2ccc3nccnc3c2)c1]

The above title compound was synthesized according to the procedure described in Example 31, except by using quinoxalin-6-ylboronic acid instead of using pyridin-4-ylboronic acid. LC-MS calculated for $C_{26}H_{17}FN_9$: 474.2 $(M+H)^+$; found: 474.3 $(M+H)^+$.

Example 38

3-(4-amino-7-(1-ethyl-1H-pyrazol-5-yl)-2-(pyridin-2-ylmethyl)-2H-[1,2,3]triazolo[4,5-c]pyridin-6-yl)-2-fluorobenzonitrile

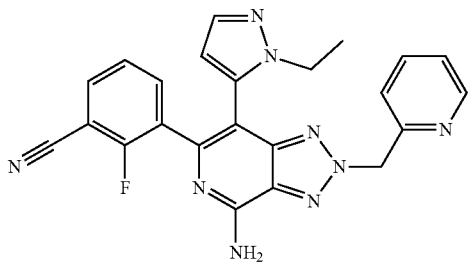 [SMILES: CCn1nccc1-c1c(-c2cccc(C#N)c2F)nc(N)c2nn(Cc3ccccn3)nc12]

Step A. 3-(4-amino-2-(pyridin-2-ylmethyl)-2H-[1,2,3]triazolo[4,5-c]pyridin-6-yl)-2-fluorobenzonitrile

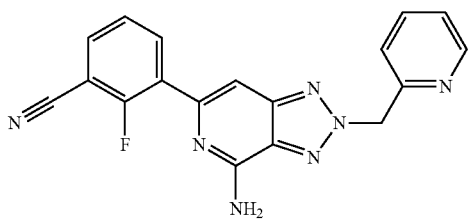 [SMILES: N#Cc1cccc(-c2cc3nn(Cc4ccccn4)nc3c(N)n2)c1F]

To the mixture of 6-chloro-N-(2,4-dimethoxybenzyl)-2-(pyridin-2-ylmethyl)-2H-[1,2,3]triazolo[4,5-c]pyridin-4-amine (300 mg, 0.730 mmol) and (3-cyano-2-fluorophenyl)boronic acid (241 mg, 1.460 mmol) was added cesium carbonate (476 mg, 1.460 mmol). The reaction was sparged with $N_2$ for 2 min. The reaction was stirred at 120° C. for 1.5 h. The reaction was quenched with 20 mL of ethyl acetate and 20 mL of water. The organic phase was separated and the aqueous solution was extracted with ethyl acetate twice. The combined extracts were dried over $Na_2SO_4$, filtered and evaporated under reduced pressure. The residue was purified on silica gel column to afford the desired product (260 mg, 72%).

The intermediate obtained from the previous step (260 mg, 0.525 mmol) in TFA (5.0 mL), and the reaction was stirred at 100° C. for 1 h. TFA was evaporated under reduced pressure and then 20 mL of saturated $NaHCO_3$ aqueous solution and 20 mL of ethyl acetate were added. The organic phase was separated and the aqueous solution was extracted with ethyl acetate twice. The combined extracts were dried over $Na_2SO_4$, filtered and evaporated under reduced pressure. The residue was purified on silica gel column to afford the desired product (151 mg, 83%). LC-MS calculated for $C_{18}H_{13}FN_7$: 346.1 $(M+H)^+$; found: 346.3 $(M+H)^+$.

Step B. 3-(4-amino-7-bromo-2-(pyridin-2-ylmethyl)-2H-[1,2,3]triazolo[4,5-c]pyridin-6-yl)-2-fluorobenzonitrile

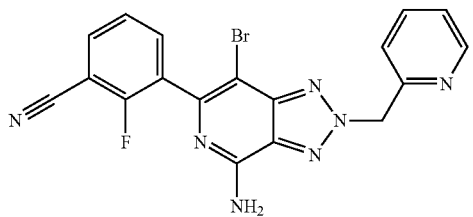 [SMILES: N#Cc1cccc(-c2nc(N)c3nn(Cc4ccccn4)nc3c2Br)c1F]

The mixture of 3-(4-amino-2-(pyridin-2-ylmethyl)-2H-[1,2,3]triazolo[4,5-c]pyridin-6-yl)-2-fluorobenzonitrile (151 mg, 0.437 mmol) and 1-bromopyrrolidine-2,5-dione (86 mg, 0.481 mmol) in THF (10 mL) was stirred at 0° C. for 1 h. Direct purification on silica gel afforded the desired product (144 mg, 78%). LC-MS calculated for $C_{18}H_{12}BrFN_7$: 424.0 $(M+H)^+$ and 426.0 $(M+H)^+$; found: 424.3 $(M+H)^+$ and 426.3 $(M+H)^+$.

Step C. 3-(4-amino-7-(1-ethyl-1H-pyrazol-5-yl)-2-(pyridin-2-ylmethyl)-2H-[1,2,3]triazolo[4,5-c]pyridin-6-yl)-2-fluorobenzonitrile

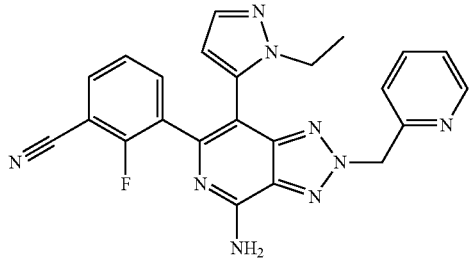 [SMILES: CCn1nccc1-c1c(-c2cccc(C#N)c2F)nc(N)c2nn(Cc3ccccn3)nc12]

Cesium carbonate (23.04 mg, 0.071 mmol) was added to the mixture of 3-(4-amino-7-bromo-2-(pyridin-2-ylmethyl)-2H-[1,2,3]triazolo[4,5-c]pyridin-6-yl)-2-fluorobenzonitrile (30 mg, 0.071 mmol) and (1-ethyl-1H-pyrazol-5-yl)boronic acid (19.79 mg, 0.141 mmol) in 1,4-dioxane (2.0 ml) and water (0.2 ml). The reaction was sparged with $N_2$ for 2 min and chloro(2-dicyclohexylphosphino-2',4',6'-triisopropyl-1,1'-biphenyl)[2-(2'-amino-1,1'-biphenyl)]palladium(II)(7.07 μmol) was added. The reaction was stirred at 120° C. for 1.5 h. Direct purification on prep. HPLC afforded the desired product. LC-MS calculated for $C_{23}H_{19}FN_9$: 440.2 $(M+H)^+$; found: 440.3 $(M+H)^+$.

Example 39

3-(4-amino-7-(1-methyl-1H-pyrazol-5-yl)-2-(pyridin-2-ylmethyl)-2H-[1,2,3]triazolo[4,5-c]pyridin-6-yl)-2-fluorobenzonitrile

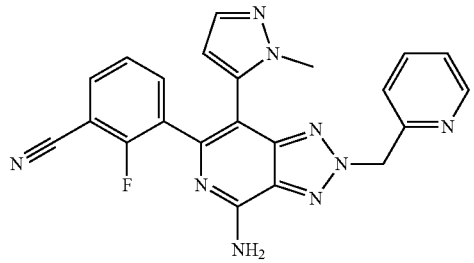 [SMILES: Cn1nccc1-c1c(-c2cccc(C#N)c2F)nc(N)c2nn(Cc3ccccn3)nc12]

The above title compound was synthesized according to the procedure described in Example 38, except by using (1-methyl-1H-pyrazol-5-yl)boronic acid instead of using (1-ethyl-1H-pyrazol-5-yl)boronic acid. LC-MS calculated for $C_{22}H_{17}FN_9$: 426.2 $(M+H)^+$; found: 426.3 $(M+H)^+$.

Example 40

3-(4-amino-7-(1-isopropyl-1H-pyrazol-5-yl)-2-(pyridin-2-ylmethyl)-2H-[1,2,3]triazolo[4,5-c]pyridin-6-yl)-2-fluorobenzonitrile

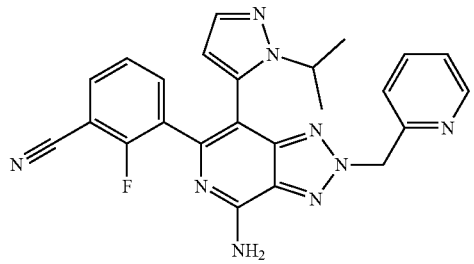 [SMILES: CC(C)n1nccc1-c1c(-c2cccc(C#N)c2F)nc(N)c2nn(Cc3ccccn3)nc12]

The above title compound was synthesized according to the procedure described in Example 38, except by using (1-isopropyl-1H-pyrazol-5-yl)boronic acid instead of using (1-ethyl-1H-pyrazol-5-yl)boronic acid. LC-MS calculated for $C_{24}H_{21}FN_9$: 454.2 $(M+H)^+$; found: 454.3 $(M+H)^+$.

Example 41

3-(4-amino-7-(4-methyloxazol-5-yl)-2-(pyridin-2-ylmethyl)-2H-[1,2,3]triazolo[4,5-c]pyridin-6-yl)-2-fluorobenzonitrile

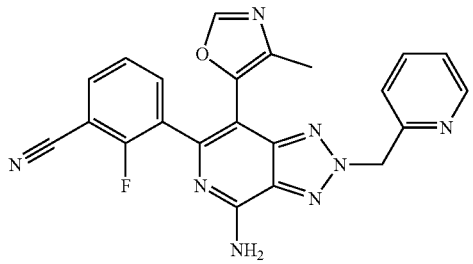 [SMILES: Cc1ncoc1-c1c(-c2cccc(C#N)c2F)nc(N)c2nn(Cc3ccccn3)nc12]

The above title compound was synthesized according to the procedure described in Example 38, except by using (4-methyloxazol-5-yl)boronic acid instead of using (1-ethyl-1H-pyrazol-5-yl)boronic acid. LC-MS calculated for $C_{22}H_{16}FN_8O$: 427.1 (M+H)+; found: 427.3 (M+H)+.

Example 42

3-(4-amino-7-(4-(hydroxymethyl)-2-methyloxazol-5-yl)-2-(pyridin-2-ylmethyl)-2H-[1,2,3]triazolo[4,5-c]pyridin-6-yl)-2-fluorobenzonitrile

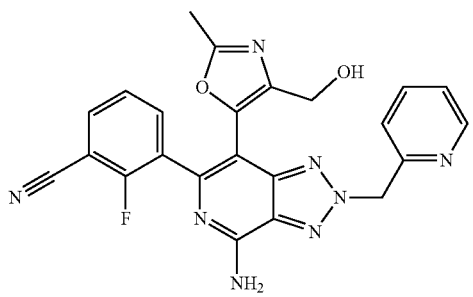 [SMILES: Cc1nc(CO)c(-c2c(-c3cccc(C#N)c3F)nc(N)c3nn(Cc4ccccn4)nc23)o1]

Step A. 4-(((tert-butyldimethylsilyl)oxy)methyl)-2-methyloxazole

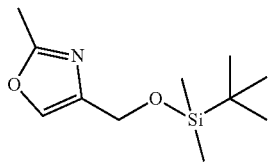

In a round-bottomed flask under $N_2$, a solution of 2-methyloxazol-4-yl)methanol (5.40 g, 26.8 mmol) in $CH_2Cl_2$ (56.0 mL) was treated at rt with tert-butylchlorodimethylsilane (8.52 g, 53.7 mmol) followed by imidazole (3.69 g, 53.67 mmol) and the resulting suspension was stirred for 1 h at rt. Water was then added, and the mixture extracted with $CH_2Cl_2$. The organic layers were dried over $Na_2SO_4$, filtered, concentrated, and purified via column chromatography (heptane/ethyl acetate) to give the desired product. LC-MS calculated for $C_{11}H_{22}NO_2Si$: 228.1 (M+H)+; found: 228.3 (M+H)+.

Step B. 4-(((tert-butyldimethylsilyl)oxy)methyl)-2-methyl-5-(4,4,5,5-tetramethyl-1,3,2-dioxaborolan-2-yl)oxazole

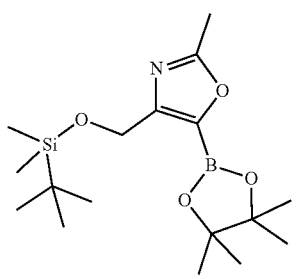

Under $N_2$ atmosphere, a flask was charged with [Ir(OMe)(1,5-cod)]$_2$ (13 mg, 0.019 mmol), 4,4,5,5-tetramethyl-1,3,2-dioxaborolane (0.085 mL, 0.58 mmol), and pentane (2.0 mL). The resulting mixture was stirred at room temperature for 10 to 15 min. 4,4'-Di-tert-butyl-2,2'-dipyridyl (dtbpy) (10.5 mg, 0.039 mmol) was added, and the reaction mixture was stirred for additional 20 min. 4-(((tert-butyldimethylsilyl)oxy)methyl)-2-methyloxazole (83 mg, 0.39 mmol) in diethyl ether (2.0 mL) was then added, and the resulting mixture was stirred at room temperature until completion. Solvent was removed under reduced pressure, and the crude material was washed with pentane to furnish the desired product. LC-MS calculated for $C_{17}H_{33}BNO_4Si$: 354.2 (M+H)+; found: 354.2 (M+H)+.

Step C. 3-(4-amino-7-(4-(hydroxymethyl)-2-methyloxazol-5-yl)-2-(pyridin-2-ylmethyl)-2H-[1,2,3]triazolo[4,5-c]pyridin-6-yl)-2-fluorobenzonitrile

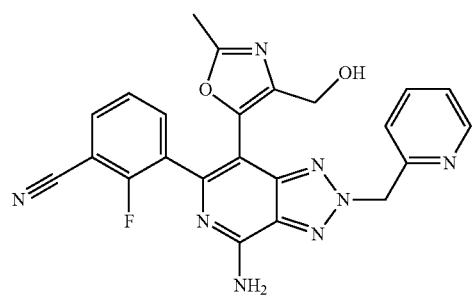 [SMILES: Cc1nc(CO)c(-c2c(-c3cccc(C#N)c3F)nc(N)c3nn(Cc4ccccn4)nc23)o1]

Cesium carbonate (77 mg, 0.236 mmol) was added to the mixture of 3-(4-amino-7-bromo-2-(pyridin-2-ylmethyl)-2H-[1,2,3]triazolo[4,5-c]pyridin-6-yl)-2-fluorobenzonitrile (50 mg, 0.118 mmol) and 4-(((tert-butyldimethylsilyl)oxy)methyl)-2-methyl-5-(4,4,5,5-tetramethyl-1,3,2-dioxaborolan-2-yl)oxazole (83 mg, 0.236 mmol) in 1,4-dioxane (2.0 mL) and Water (0.20 mL). The reaction was sparged with $N_2$ for 2 min and chloro(2-dicyclohexylphosphino-2',4',6'-triisopropyl-1,1'-biphenyl)[2-(2'-amino-1,1'-biphenyl)]palladium(II)(9.20 mg, 0.012 mmol) was added. The reaction was stirred at 120° C. for 1.5 h.

To the reaction mixture was added TFA (1.0 mL, 12.98 mmol). The reaction mixture was stirred at 100° C. for 1 h. The reaction mixture was diluted with methanol. Direct purification on prep. HPLC afforded the desired product. LC-MS calculated for $C_{23}H_{18}FN_8O_2$: 457.2 $(M+H)^+$; found: 457.3 $(M+H)^+$.

Example 43

3-(4-amino-2-(pyridin-2-ylmethyl)-7-(quinoxalin-6-yl)-2H-[1,2,3]triazolo[4,5-c]pyridin-6-yl)-2-fluorobenzonitrile

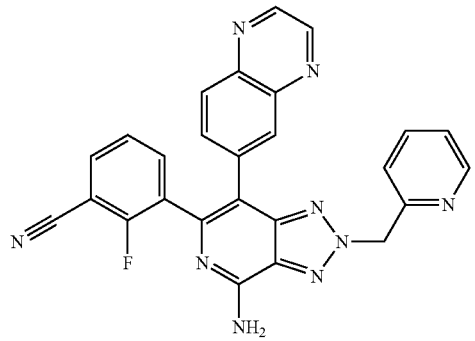 [SMILES: N#Cc1cccc(-c2nc(N)c3nn(Cc4ccccn4)nc3c2-c2ccc3nccnc3c2)c1F]

The title compound was synthesized according to the procedure described in Example 38, except by using quinoxalin-6-ylboronic acid instead of using (1-ethyl-1H-pyrazol-5-yl)boronic acid. LC-MS calculated for $C_{26}H_{17}FN_9$: 474.2 $(M+H)^+$; found: 474.3 $(M+H)^+$.

Example 44

3-(4-amino-2-((1-methyl-1H-pyrazol-3-yl)methyl)-7-(pyrimidin-4-yl)-2H-[1,2,3]triazolo[4,5-c]pyridin-6-yl)benzonitrile

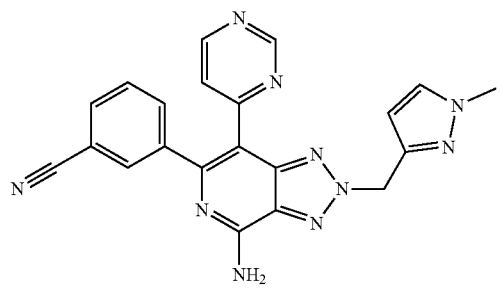

Step A. 6-chloro-N-(2,4-dimethoxybenzyl)-2-((1-methyl-1H-pyrazol-3-yl)methyl)-2H-[1,2,3]triazolo[4,5-c]pyridin-4-amine

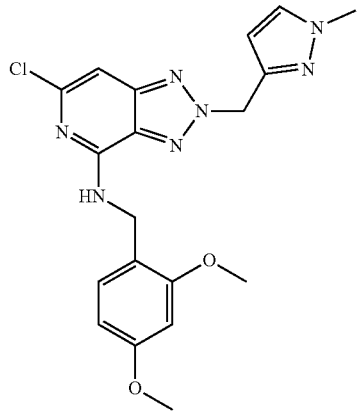 [SMILES: COc1ccc(CNc2nc(Cl)cc3nn(Cc4ccn(C)n4)nc23)c(OC)c1]

To the mixture of 6-chloro-N-(2,4-dimethoxybenzyl)-3H-[1,2,3]triazolo[4,5-c]pyridin-4-amine (1000 mg, 3.13 mmol), (1-methyl-1H-pyrazol-3-yl)methanol (421 mg, 3.75 mmol) and triphenylphosphine (1641 mg, 6.25 mmol) in DCM (10 mL) was added diisopropyl azodicarboxylate (0.739 mL, 3.75 mmol) at 0° C. The reaction mixture was stirred at 0° C. for 1 h. Direct purification on silica gel column afforded the desired product (345 mg, 27%). LC-MS calculated for $C_{19}H_{21}ClN_7O_2$: 414.1 $(M+H)^+$; found: 414.2 $(M+H)^+$.

Step B. 3-(4-((2,4-dimethoxybenzyl)amino)-2-((1-methyl-1H-pyrazol-3-yl)methyl)-2H-[1,2,3]triazolo[4,5-e]pyridin-6-yl)benzonitrile

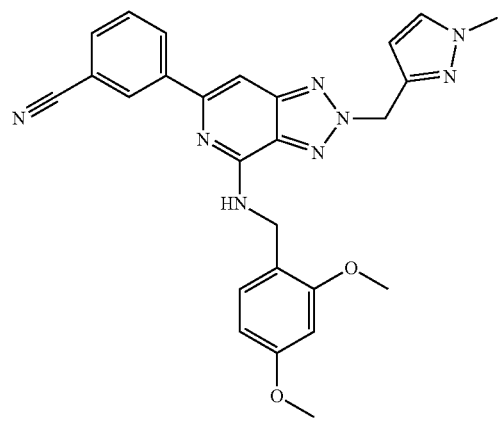 [SMILES: COc1ccc(CNc2nc(-c3cccc(C#N)c3)cc3nn(Cc4ccn(C)n4)nc23)c(OC)c1]

Cesium carbonate (543 mg, 1.667 mmol) was added to the mixture of 6-chloro-N-(2,4-dimethoxybenzyl)-2-((1-methyl-1H-pyrazol-3-yl)methyl)-2H-[1,2,3]triazolo[4,5-c]pyridin-4-amine (345 mg, 0.834 mmol), (3-cyanophenyl)boronic acid (245 mg, 1.667 mmol) in 1,4-dioxane (10 ml) and water (1.00 ml). The reaction was sparged with $N_2$ for 2 min and chloro(2-dicyclohexylphosphino-2',4',6'-triisopropyl-1,1'-biphenyl)[2-(2'-amino-1,1'-biphenyl)]palladium (II) (65.6 mg, 0.083 mmol) was added. The reaction was stirred at 120° C. for 1.5 h. The reaction was quenched with 20 mL of ethyl acetate and 20 mL of water. The organic phase was separated and the aqueous solution was extracted with ethyl acetate twice. The combined extracts were dried over Na$_2$SO$_4$, filtered and evaporated under reduced pressure. The residue was purified on silica gel column to afford the desired product (305 mg, 76%). LC-MS calculated for C$_{26}$H$_{25}$N$_8$O$_2$: 481.2 (M+H)$^+$; found: 481.3 (M+H)$^+$.

Step C. 3-(4-amino-2-((1-methyl-1H-pyrazol-3-yl)methyl)-2H-[1,2,3]triazolo[4,5-c]pyridin-6-yl)benzonitrile

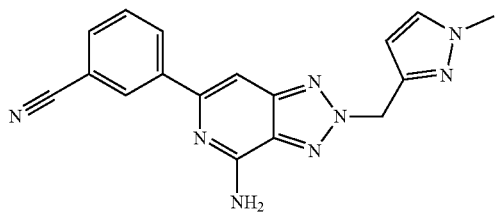 [SMILES: Cn1ccc(Cn2nc3cc(-c4cccc(C#N)c4)nc(N)c3n2)n1]

The solution of 3-(4-((2,4-dimethoxybenzyl)amino)-2-((1-methyl-1H-pyrazol-3-yl)methyl)-2H-[1,2,3]triazolo[4,5-c]pyridin-6-yl)benzonitrile (305.3 mg, 0.635 mmol) in TFA (5 mL) was stirred at 100° C. for 1 h. TFA was evaporated under reduced pressure and then 20 mL of saturated NaHCO$_3$ aqueous solution and 20 mL of ethyl acetate were added. The organic phase was separated and the aqueous solution was extracted with ethyl acetate twice. The combined extracts were dried over Na$_2$SO$_4$, filtered and evaporated under reduced pressure. The residue was purified on silica gel column to afford the desired product (159 mg, 76%). LC-MS calculated for C$_{17}$H$_{15}$N$_8$: 331.1 (M+H)$^+$; found: 331.3 (M+H)$^+$.

Step D. 3-(4-amino-7-bromo-2-((1-methyl-1H-pyrazol-3-yl)methyl)-2H-[1,2,3]triazolo[4,5-c]pyridin-6-yl)benzonitrile

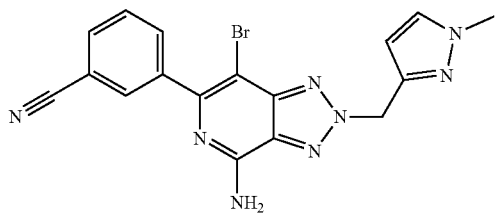 [SMILES: Cn1ccc(Cn2nc3c(N)nc(-c4cccc(C#N)c4)c(Br)c3n2)n1]

The mixture of 3-(4-amino-2-((1-methyl-1H-pyrazol-3-yl)methyl)-2H-[1,2,3]triazolo[4,5-c]pyridin-6-yl)benzonitrile (159 mg, 0.481 mmol) and 1-bromopyrrolidine-2,5-dione (90 mg, 0.505 mmol) in THF (10 mL) was stirred at 0° C. for 1 h. Direct purification on silica gel column afforded the desired product (149 mg, 76%). LC-MS calculated for C$_{17}$H$_{14}$BrN$_8$: 409.1 (M+H)$^+$ and 411.1 (M+H)$^+$; found: 409.3 (M+H)$^+$ and 411.3 (M+H)$^+$.

Step E. 3-(4-amino-2-((1-methyl-1H-pyrazol-3-yl)methyl)-7-(pyrimidin-4-yl)-2H-[1,2,3]triazolo[4,5-c]pyridin-6-yl)benzonitrile

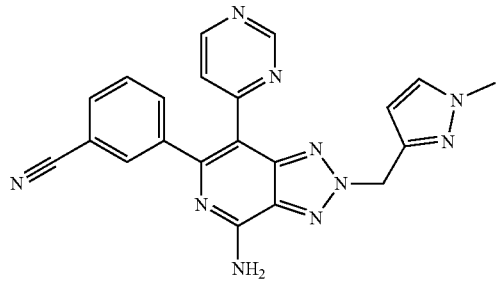 [SMILES: Cn1ccc(Cn2nc3c(N)nc(-c4cccc(C#N)c4)c(-c4ccncn4)c3n2)n1]

The mixture of 3-(4-amino-7-bromo-2-((1-methyl-1H-pyrazol-3-yl)methyl)-2H-[1,2,3]triazolo[4,5-c]pyridin-6-yl)benzonitrile (220 mg, 0.538 mmol), 4-(tributylstannyl)pyrimidine (50 mg, 0.135 mmol), and copper(I) chloride (63.9 mg, 0.645 mmol), lithium chloride (27.3 mg, 0.645 mmol) and tetrakis(triphenylphosphine)palladium(0) (62.1 mg, 0.054 mmol) in THF (1 ml) was first purged with N$_2$, and then heated and stirred at 90° C. for 2 h. The reaction was diluted with methanol and purified with prep-LCMS (pH 2) to give the desired compound. LC-MS calculated for C$_{21}$H$_{17}$N$_{10}$: 409.2 (M+H)$^+$; found: 409.3 (M+H)$^+$.

Example 45

3-(4-amino-2-((1-methyl-1H-pyrazol-3-yl)methyl)-7-(4-methyloxazol-5-yl)-2H-[1,2,3]triazolo[4,5-c]pyridin-6-yl)benzonitrile

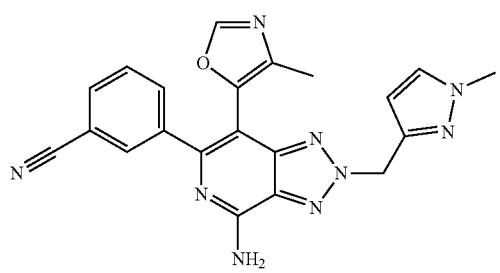 [SMILES: Cc1ncoc1-c1c(-c2cccc(C#N)c2)nc(N)c2nn(Cc3ccn(C)n3)nc12]

Cesium carbonate (159 mg, 0.489 mmol) was added to the mixture of 3-(4-amino-7-bromo-2-((1-methyl-1H-pyrazol-3-yl)methyl)-2H-[1,2,3]triazolo[4,5-c]pyridin-6-yl)benzonitrile (100 mg, 0.244 mmol) and 4-methyl-5-(4,4,5,5-tetramethyl-1,3,2-dioxaborolan-2-yl)oxazole (102 mg, 0.489 mmol) in 1,4-dioxane (2.0 mL) and water (0.2 mL). The reaction was sparged with N$_2$ for 2 min and chloro(2-dicyclohexylphosphino-2',4',6'-triisopropyl-1,1'-biphenyl)[2-(2'-amino-1,1'-biphenyl)]palladium(II) (17 mg, 0.024 mmol) was added. The reaction was stirred at 120° C. for 1.5 h. The reaction mixture was diluted with methanol. Direct purification on prep. HPLC afforded the desired product. LC-MS calculated for C$_{21}$H$_{18}$N$_9$O: 412.2 (M+H)$^+$; found: 412.3 (M+H)$^+$.

Example 46

3-(4-amino-7-(4-methyloxazol-5-yl)-2-(1-(pyridin-2-yl)ethyl)-2H-[1,2,3]triazolo[4,5-c]pyridin-6-yl)benzonitrile

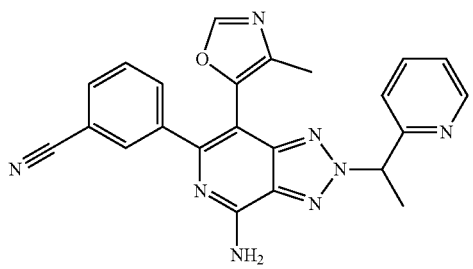 [SMILES: Cc1ncoc1-c1c(-c2cccc(C#N)c2)nc(N)c2nn(C(C)c3ccccn3)nc12]

Step A. 6-chloro-N-(2,4-dimethoxybenzyl)-2-(1-(pyridin-2-yl)ethyl)-2H-[1,2,3]triazolo[4,5-c]pyridin-4-amine

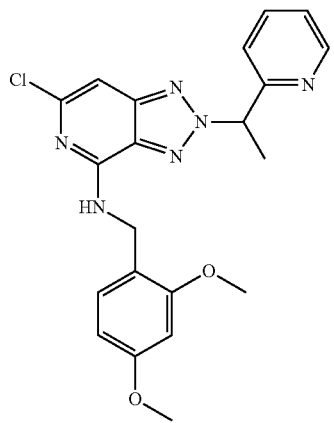 [SMILES: COc1ccc(CNc2nc(Cl)cc3nn(C(C)c4ccccn4)nc23)c(OC)c1]

The mixture of 6-chloro-N-(2,4-dimethoxybenzyl)-3H-[1,2,3]triazolo[4,5-c]pyridin-4-amine (1000 mg, 3.13 mmol), 1-(pyridin-2-yl)ethan-1-ol (462 mg, 3.75 mmol), triphenylphosphine (1641 mg, 6.25 mmol) and diisopropyl azodicarboxylate (0.739 mL, 3.75 mmol) was stirred at 0° C. for 1 h. Direct purification on silica gel column afforded the desired product (359 mg, 27%). LC-MS calculated for $C_{21}H_{22}ClN_6O_2$: 425.1 (M+H)$^+$; found: 425.3 (M+H)$^+$.

Step B. 3-(4-((2,4-dimethoxybenzyl)amino)-2-(1-(pyridin-2-yl)ethyl)-2H-[1,2,3]triazolo[4,5-c]pyridin-6-yl)benzonitrile

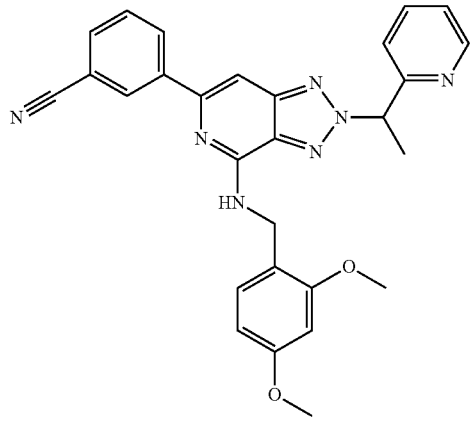 [SMILES: COc1ccc(CNc2nc(-c3cccc(C#N)c3)cc3nn(C(C)c4ccccn4)nc23)c(OC)c1]

Cesium carbonate (551 mg, 1.690 mmol) was added to the mixture of 6-chloro-N-(2,4-dimethoxybenzyl)-2-(1-(pyridin-2-yl)ethyl)-2H-[1,2,3]triazolo[4,5-c]pyridin-4-amine (359 mg, 0.845 mmol) and (3-cyanophenyl)boronic acid (248 mg, 1.690 mmol) in 1,4-dioxane (10 mL) and Water (1.00 mL). The resulting reaction mixture was sparged with $N_2$ for 2 min and chloro(2-dicyclohexylphosphino-2',4',6'-triisopropyl-1,1'-biphenyl)[2-(2'-amino-1,1'-biphenyl)]palladium(II) (66.5 mg, 0.084 mmol) was added. The reaction was stirred at 120° C. for 1.5 h. The reaction was quenched with 20 mL of ethyl acetate and 20 mL of water. The organic phase was separated and the aqueous solution was extracted with ethyl acetate twice. The combined extracts were dried over $Na_2SO_4$, filtered and evaporated under reduced pressure. The residue was purified on silica gel column to afford the desired product (347 mg, 84%). LC-MS calculated for $C_{28}H_{26}N_7O_2$: 492.2 (M+H)$^+$; found: 492.3 (M+H)$^+$.

Step C. 3-(4-amino-2-(1-(pyridin-2-yl)ethyl)-2H-[1,2,3]triazolo[4,5-e]pyridin-6-yl)benzonitrile

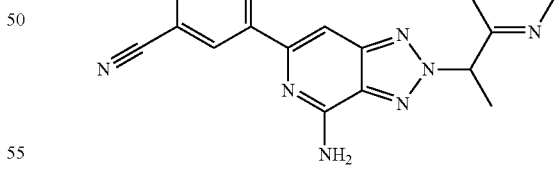

The solution of 3-(4-((2,4-dimethoxybenzyl)amino)-2-(1-(pyridin-2-yl)ethyl)-2H-[1,2,3]triazolo[4,5-c]pyridin-6-yl)benzonitrile (347 mg, 0.707 mmol) in TFA (5.00 mL) was stirred at 100° C. for 1 h. TFA was evaporated under reduced pressure and then 20 mL of saturated $NaHCO_3$ aqueous solution and 20 mL of ethyl acetate were added. The organic phase was separated and the aqueous solution was extracted with ethyl acetate twice. The combined extracts were dried over $Na_2SO_4$, filtered and evaporated under reduced pressure. The residue was purified on silica gel column to afford the desired product (200 mg, 83%). LC-MS calculated for $C_{19}H_{16}N_7$: 342.1 (M+H)$^+$; found: 342.3 (M+H)$^+$.

Step D. 3-(4-amino-7-bromo-2-(1-(pyridin-2-yl)ethyl)-2H-[1,2,3]triazolo[4,5-c]pyridin-6-yl)benzonitrile

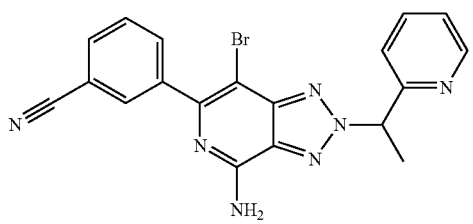 [SMILES: CC(c1ccccn1)n1nc2c(N)nc(-c3cccc(C#N)c3)c(Br)c2n1]

The mixture of 3-(4-amino-2-(1-(pyridin-2-yl)ethyl)-2H-[1,2,3]triazolo[4,5-c]pyridin-6-yl)benzonitrile (200 mg, 0.586 mmol) and 1-bromopyrrolidine-2,5-dione (115 mg, 0.644 mmol) in THF (10 ml) was stirred at 0° C. for 1 h. Direct purification on silica gel column afforded the desired product (197 mg, 80%). LC-MS calculated for $C_{19}H_{15}BrN_7$: 420.1 (M+H)$^+$ and 422.1(M+H)$^+$; found: 420.3 (M+H)$^+$ and 422.3 (M+H)$^+$.

Step E. 3-(4-amino-7-(4-methyloxazol-5-yl)-2-(1-(pyridin-2-yl)ethyl)-2H-[1,2,3]triazolo[4,5-c]pyridin-6-yl)benzonitrile

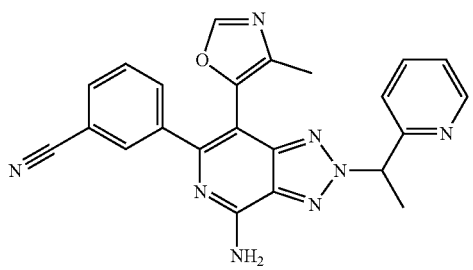

Cesium carbonate (132 mg, 0.404 mmol) was added to the mixture of 3-(4-amino-7-bromo-2-(1-(pyridin-2-yl)ethyl)-2H-[1,2,3]triazolo[4,5-c]pyridin-6-yl)benzonitrile (85 mg, 0.202 mmol) and 4-methyl-5-(4,4,5,5-tetramethyl-1,3,2-dioxaborolan-2-yl)oxazole (85 mg, 0.404 mmol) in 1,4-dioxane (2.0 mL) and water (0.2 mL). The resulting mixture was sparged with $N_2$ for 2 min and chloro(2-dicyclohexylphosphino-2',4',6'-triisopropyl-1,1'-biphenyl)[2-(2'-amino-1,1'-biphenyl)]palladium(II) (0.020 mmol) was added. The reaction was stirred at 120° C. for 1.5 h. The reaction mixture was diluted with methanol. Direct purification on prep. HPLC afforded the desired product. LC-MS calculated for $C_{23}H_{19}N_8O$: 423.2 (M+H)$^+$; found: 423.3 (M+H)$^+$.

Example 47

3-(4-amino-2-(1-(pyridin-2-yl)ethyl)-7-(pyrimidin-4-yl)-2H-[1,2,3]triazolo[4,5-c]pyridin-6-yl)benzonitrile

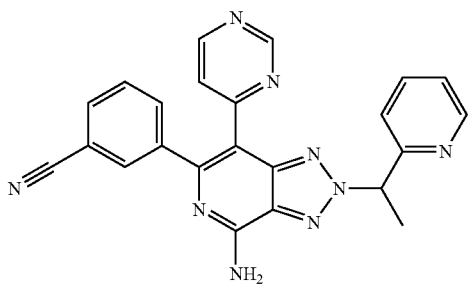

A mixture of 3-(4-amino-7-bromo-2-(1-(pyridin-2-yl)ethyl)-2H-[1,2,3]triazolo[4,5-c]pyridin-6-yl)benzonitrile (85 mg, 0.202 mmol), 4-(tributylstannyl)pyrimidine (50 mg, 0.135 mmol), and copper(I) chloride (24.03 mg, 0.243 mmol), lithium chloride (10.29 mg, 0.243 mmol) and tetrakis(triphenylphosphine)palladium(0) (23.37 mg, 0.020 mmol) in THF (1 ml) was first purged with $N_2$, and then heated and stirred at 90 C for 2 h. The reaction was diluted with methanol and purified with prep-LCMS (pH=2) to give the desired product. LC-MS calculated for $C_{23}H_{18}N_9$: 420.2 (M+H)$^+$; found: 420.3 (M+H)$^+$.

Example 48

3-(4-amino-7-(4-methyloxazol-5-yl)-2-(2-(pyridin-2-yl)ethyl)-2H-[1,2,3]triazolo[4,5-c]pyridin-6-yl)benzonitrile

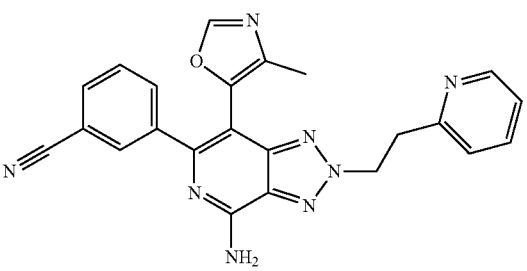 [SMILES: Cc1ncoc1-c1c(-c2cccc(C#N)c2)nc(N)c2nn(CCc3ccccn3)nc12]

The above title compound was synthesized according to the procedure described in Example 46, except by using 2-(pyridin-2-yl)ethan-1-ol instead of using 1-(pyridin-2-yl)ethan-1-ol in step A. LC-MS calculated for $C_{23}H_{19}N_8O$: 423.2 (M+H)$^+$; found: 423.3 (M+H)$^+$.

Example 49

3-(4-amino-7-(4-methyloxazol-5-yl)-2-(2-(pyridin-2-yl)ethyl)-2H-[1,2,3]triazolo[4,5-c]pyridin-6-yl)-2-fluorobenzonitrile

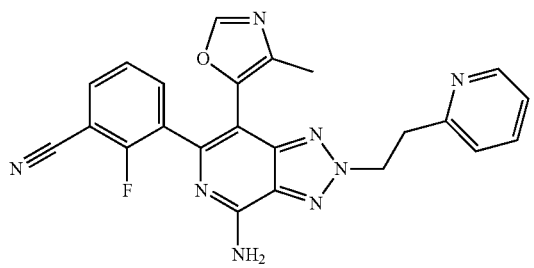 [SMILES: Cc1ncoc1-c1c(-c2cccc(C#N)c2F)nc(N)c2nn(CCc3ccccn3)nc12]

The above title compound was synthesized according to the procedure described in Example 48, except by using (2-fluoro-3-cyanophenyl)boronic acid instead of using (3-cyanophenyl)boronic acid. LC-MS calculated for $C_{23}H_{18}FN_8O$: 441.2 $(M+H)^+$; found: 441.3 $(M+H)^+$.

Example A

Adenosine A2A Receptor Cyclic AMP GS Assay

Stably transfected HEK-293 cells expressing the human adenosine A2A receptor (Perkin Elmer) are maintained in MEM culture medium with 10% FBS and 400 μg/mL Geneticin (Life Technologies). 18 to 24 hours prior to assay, geneticin is removed from culture. The cisbio cAMP-GS Dynamic kit utilizing the FRET (Fluorescence Resonance Energy Transfer) technology is used to measure cAMP accumulation in the cells. Compounds of the present disclosure at an appropriate concentration are mixed with 10000 cells/well in white 96 well half area plates (Perkin Elmer) for 30 min at RT gently shaking. Agonist, CGS21680 (R&D Technologies) at 4 nM is added to each well for 60 min at room temperature gently shaking. Detection reagents, d2-labeled cAMP (acceptor) and anti-cAMP cryptate (donor) are added to each well for 60 min at room temperature gently shaking. Plates are read on Pherastar (BMG Labtech), fluorescence ratio 665/620 is calculated and $EC_{50}$ determination is performed by fitting the curve of percent of control versus the log of the compound concentration using GraphPad Prism.

Example B

Adenosine A2B Receptor Cyclic AMP GS Assay

Stably transfected HEK-293 cells expressing the human adenosine A2B receptor (Perkin Elmer) were maintained in MEM culture medium with 10% FBS and 100 μg/mL Geneticin (Life Technologies). 18 to 24 hours prior to assay, geneticin was removed from culture. The cisbio cAMP-GS Dynamic kit utilizing the FRET (Fluorescence Resonance Energy Transfer) technology was used to measure cAMP accumulation in the cells. Compounds of the present disclosure at an appropriate concentration were mixed with 10000 cells/well in white 96 well half area plates (Perkin Elmer) for 30 min at room temperature gently shaking. Agonist, NECA (R&D Technologies) at 12 nM was added to each well for 60 min at room temperature gently shaking. Detection reagents, d2-labeled cAMP (acceptor) and anti-cAMP cryptate (donor) were added to each well for 60 min at RT gently shaking. Plates were read on Pherastar (BMG Labtech), fluorescence ratio 665/620 was calculated and $EC_{50}$ determination was performed by fitting the curve of percent of control versus the log of the compound concentration using GraphPad Prism. The $EC_{50}$ data for the Examples obtained via this method are shown in Table 1.

TABLE 1

The $A_{2A}\_Ki$ data and $A_{2B}\_cAMP\_EC_{50}$ data are provided below. The symbol "†" indicates $A_{2A}\_Ki$ or $A_{2B}\_cAMP\_EC_{50} \leq$ 10 nM, "††" indicates $A_{2A}\_Ki$ or $A_{2B}\_cAMP\_EC_{50} >$ 10 nM but $\leq$100 nM. "†††" indicates $A_{2A}\_Ki$ or $A_{2B}\_cAMP\_EC_{50} >$ 100 nM but $\leq$1 μM; and "††††" indicates $A_{2A}\_Ki$ or $A_{2B}\_cAMP\_EC_{50}$ is greater than 1 μM.

| Ex. No. | $A_{2A}\_Ki$ (nM) | $A_{2B}\_cAMP\_EC_{50}$ (nM) |
|---|---|---|
| 1 | † | †† |
| 2 | † | † |
| 3 | † | †† |
| 4 | † | †† |
| 5 | NA | NA |
| 6 | † | † |
| 7 | † | † |
| 8 | † | † |
| 9 | † | † |
| 10 | † | † |
| 11 | † | †† |
| 12 | † | †† |
| 13 | † | †† |
| 14 | † | † |
| 15 | NA | NA |
| 16 | † | † |
| 17 | † | † |
| 18 | † | † |
| 19 | † | † |
| 20 | † | † |
| 21 | † | † |
| 22 | † | † |
| 23 | † | ††† |
| 24 | † | † |
| 25 | † | † |
| 26 | † | † |
| 27 | † | †† |
| 28 | † | † |
| 29 | † | † |
| 30 | † | † |
| 31 | † | † |
| 32 | † | †† |
| 33 | † | † |
| 34 | † | † |
| 35 | † | † |
| 36 | † | † |
| 37 | † | †† |
| 38 | † | † |
| 39 | † | † |
| 40 | † | † |
| 41 | † | † |
| 42 | † | †† |
| 43 | † | ††† |
| 44 | † | † |
| 45 | † | † |
| 46 | † | † |
| 47 | † | ††† |
| 48 | † | †† |
| 49 | † | †† |

Example C

A2A Tag-lite® HTRF Assay

Assays were conducted in black low volume 384-well polystyrene plates (Greiner 784076-25) in a final volume of 10 μL. Test compounds were first serially diluted in DMSO and 100 nl added to the plate wells before the addition of other reaction components. The final concentration of DMSO was 1%. Tag-lite® Adenosine A2A labeled cells (CisBio C1TT1A2A) were diluted 1:5 into Tag-lite buffer (CisBio LABMED) and spun 1200 g for 5 mins. The pellet was resuspended at a volume 10.4× the initial cell suspension volume in Tag-lite buffer, and Adenosine A2A Receptor Red antagonist fluorescent ligand (CisBio L0058RED) added at 12.5 nM final concentration. 10 ul of the cell and ligand mix was added to the assay wells and incubated at room temperature for 45 minutes before reading on a PHERAstar FS plate reader (BMG Labtech) with HTRF 337/620/665 optical module. Percent binding of the fluorescent ligand was calculated; where 100 nM of A2A antagonist control ZM 241385 (Tocris 1036) displaces the ligand 100% and 1% DMSO has 0% displacement. The % binding data versus the log of the inhibitor concentration was fitted to a one-site competitive binding model (GraphPad Prism version 7.02) where the ligand constant=12.5 nM and the ligand Kd=1.85 nM. The $K_i$ data for the Examples obtained via this method are shown in Table 1 (See Example B).

Example D

A2B Filter Binding Assay

Assays are conducted in deep well polypropylene plates (Greiner 786201) in a final volume of 550 µL. Test compounds are first serially diluted in DMSO and 5.5 ul is then added to the plate wells before the addition of other reaction components. The final concentration of DMSO is 3%. HEK293 cell membranes overexpressing the human adenosine receptor A2B (Perkin Elmer ES-113-M400UA) are diluted to 40 ug/mL in 50 mM HEPES pH 7.0, 5 mM $MgCl_2$, 1 mM EDTA (Assay buffer). [3H] 8-cyclopentyl-1,3-dipropylxanthine (Perkin Elmer NET974001MC) is diluted in assay buffer+22% DMSO to 24.2 nM, and then further diluted to 1 nM by addition to the diluted membranes. 545 µl of the membrane and ligand mix is added to the assay wells and incubated on a shaker at room temperature for 1 hour. The membrane mix is then filtered over a UniFilter GF/C filter plate (Perkin Elmer 6005174) pre-soaked in 50 mM HEPES pH 6.5, 5 mM $MgCl_2$, 1 mM EDTA 0.5% BSA and then washed with 5 mL ice cold 50 mM HEPES pH 6.5, 5 mM $MgCl_2$, 1 mM EDTA 0.2% BSA. 50 µl MicroScint™ cocktail (Perkin Elmer 6013621) is added and plates are read on a Topcount NXT FS (Perkin Elmer). Percent binding of the [3H] ligand is calculated, where 1000 nM of LUF 5834 (Tocris 4603) control displaces the ligand 100% and 3% DMSO has 0% displacement. The % binding data versus the log of the inhibitor concentration is fitted to a one-site competitive binding model (GraphPad Prism version 7.02) where the ligand constant=2 nM and the ligand Kd=13 nM.

Example E

A1 and A3 SPA Binding Assays

Both assays are conducted in white 384-well polystyrene plates (Greiner 781075) in a final volume of 50 µL. Inhibitors are first serially diluted in DMSO and 100 nL is added to the plate wells before the addition of other reaction components. The final concentration of DMSO is 2%.

Wheatgerm agglutinin-coated yttrium silicate SPA beads (Perkin Elmer RPNQ0023) and CHO-K1 cell membranes overexpressing each human adeonsine receptor are incubated in 50 mM HEPES pH 7.0, 5 mM $MgCl_2$, 1 mM EDTA (Assay buffer) on a rotary stirrer for 2 hours at 4° C. The beads are pelleted by centrifugation at 6000 g for one minute, and then the supernatant with unbound membrane is discarded. The beads are re-suspended to the original volume in assay buffer. Each radioligand is diluted in assay buffer+22% DMSO at 12.2× the final concentration, and then added to the SPA bead suspension. 50 µl of the SPA bead reaction mix is added to the assay wells and the plates shaken at 600 rpm for 1 hour at room temperature. The beads are then allowed to settle for 1 hour before reading on a Topcount NXT FS (Perkin Elmer). Percent binding of the radiolabeled ligand is calculated, where a control at >100× Ki displaces the ligand 100% and 2% DMSO has 0% displacement. The % binding data versus the log of the inhibitor concentration is fitted to a one-site competitive binding model (GraphPad Prism version 7.02). Assay conditions are provided in Table A below.

TABLE A

| Assay Component | A1 | A3 |
|---|---|---|
| SPA beads in Hepes buffer | 3 mg/mL | 1.25 mg/mL |
| Membrane | 60 µg/mL Perkin Elmer ES-010 | 20 µg/mL Perkin Elmer ES-012 |
| Radioligand | 1 nM [3H] DP-CPX (Perkin Elmer NET974) $K_D$ = 1 nM | 0.1 nM [125I] MECA (Perkin Elmer NEX312) $K_D$ = 0.8 nM |
| Control | 1 µM DPCPX (Tocris 0439) | 0.1 µM IB-MECA (Tocris 1066) |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula (I):

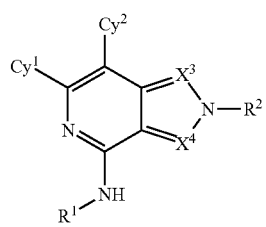

or a pharmaceutically acceptable salt thereof, wherein:
$X^3$ is N or $CR^3$;
$X^4$ is N or $CR^4$;
$Cy^1$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $Cy^1$ are each optionally substituted with 1, 2, 3, 4, 5, or 6 independently selected $R^5$ substituents;
$Cy^2$ is selected from $C_{6-10}$ aryl, $C_{3-10}$ cycloalkyl, 5-10 membered heteroaryl, and 4-10 membered heterocycloalkyl, wherein the $C_{6-10}$ aryl, $C_{3-10}$ cycloalkyl, 5-10 membered heteroaryl, and 4-10 membered heterocycloalkyl of $Cy^2$ are each optionally substituted with 1, 2, 3, 4, 5, or 6 independently selected $R^6$ substituents;

$R^1$ is selected from H, $C_{1-6}$ alkyl, $C_{2-6}$ alkenyl, $C_{2-6}$ alkynyl, $C_{1-6}$ haloalkyl, $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, and $S(O)_2R^{b1}$, and $S(O)_2NR^{c1}R^{d1}$, wherein the $C_{1-6}$ alkyl, $C_{2-6}$ alkenyl, and $C_{2-6}$ alkynyl of $R^1$ are each optionally substituted with 1, 2, 3, or 4 independently selected $R^{1A}$ substituents;

each $R^{a1}$, $R^{b1}$, $R^{c1}$, and $R^{d1}$ is independently selected from H, $C_{1-6}$ alkyl, $C_{2-6}$ alkenyl, $C_{2-6}$ alkynyl, and $C_{1-6}$ haloalkyl, wherein the $C_{1-6}$ alkyl, $C_{2-6}$ alkenyl, and $C_{2-6}$ alkynyl of $R^{a1}$, $R^{b1}$, $R^{c1}$, and $R^{d1}$ are each optionally substituted with 1, 2, 3, or 4 independently selected $R^{1A}$ substituents;

each $R^{e1}$ is independently selected from H, OH, CN, $C_{1-6}$ alkyl, $C_{2-6}$ alkenyl, $C_{2-6}$ alkynyl, $C_{1-6}$ alkoxy, $C_{1-6}$ haloalkyl, and $C_{1-6}$ haloalkoxy;

each $R^{1A}$ is independently selected from OH, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino;

$R^2$ is selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$alkyl-, (5-10 membered heteroaryl)-$C_{1-6}$ alkyl-, (4-10 membered heterocycloalkly)-$C_{1-6}$alkyl-, $C(O)R^{b2}$, $C(O)NR^{c2}R^{d2}$, $C(O)OR^{a2}$, $C(=NR^{e2})R^{b2}$, $C(=NR^{e2})NR^{c2}R^{d2}$, $S(O)_2R^{b2}$, and $S(O)_2NR^{c2}R^{d2}$, wherein the $C_{1-6}$alkyl, $C_{2-6}$alkenyl, $C_{2-6}$ alkynyl, $C_{6-10}$ aryl, $C_{3-10}$cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$alkyl-, and (4-10 membered heterocycloalkyl)-$C_{1-6}$ alkyl- of $R^2$ are each optionally substituted with 1, 2, 3, 4, 5, or 6 independently selected $R^{2A}$ substituents;

each $R^{a2}$, $R^{b2}$, $R^{c2}$, and $R^{d2}$ is independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{b2}$, $R^{c2}$, and $R^{d2}$ are each optionally substituted with 1, 2, 3, 4, 5, or 6 independently selected $R^{2A}$ substituents;

or, any $R^{c2}$ and $R^{d2}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{2A}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NR^{e21})NR^{c21}R^{d21}$, $NR^{c21}C(=NR^{e21})NR^{c21}R^{d21}$, $NR^{c21}C(=NR^{e21})R^{b21}$, $NR^{c21}S(O)NR^{c21}R^{d21}$, $NR^{c21}S(O)R^{b21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}$, $R^{d21}$, $S(O)_2R^{b21}$, $S(O)_2NR^{c21}R^{d21}$, $(S)(O)(=NR^{e21})R^{b21}$, $OS(O)_2R^{b21}$, $SF_5$, $P(O)R^{f21}R^{g21}$, $OP(O)(OR^{h21})(OR^{i21})$, $P(O)(OR^{h21})(OR^{i21})$, and $BR^{j21}R^{k21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, 4, 5, or 6 independently selected $R^{2B}$ substituents;

Each $R^{a21}$, $R^{b21}$, $R^{c21}$ and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$ and $R^{d21}$ are each optionally substituted with 1, 2, 3, 4, 5, or 6 independently selected $R^{2B}$ substituents;

or, any $R^{c21}$ and $R^{d21}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{2B}$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f21}$ and $R^{g21}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h21}$ and $R^{i21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j21}$ and $R^{k21}$ is independently selected from OH, $C_{1-6}$ alkoxy, and $C_{1-6}$ haloalkoxy;

or any $R^{j21}$ and $R^{k21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2B}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $SR^{a22}$, $NHOR^{a22}$, $C(O)R^{b22}$ $C(O)NR^{c22}R_{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}NR^{c22}R^{d22}$, $NR^{c22}C(O)R^{b22}$, $NR^{c22}C(O)OR^{a22}$, $NR^{c22}C(O)NR^{c22}R^{d22}$, $C(=NR^{e22})R^{b22}$, $C(=NR^{e22})NR^{c22}R^{d22}$, $NR^{c22}C(=NR^{e22})NR^{c22}R^{d22}$, $NR^{c22}C(=NR^{e22})R^{b22}$, $NR^{c22}S(O)NR^{c22}R^{d22}$, $NR^{c22}S(O)R^{b22}$, $NR^{c22}S(O)_2R^{b22}$, $NR^{c22}S(O)(=NR^{e22})R^{b22}$, $NR^{c22}S(O)_2NR^{c22}R^{d22}$, $S(O)R^{b22}$, $S(O)NR^{c22}R^{d22}$, $S(O)_2R^{b22}$, $S(O)_2NR^{c22}R^{b22}$, $OS(O)(=NR^{e22})R^{b22}$, $OS(O)_2R^{b22}$, $SF_5$, $P(O)R^{f22}R^{g22}$, $OP(O)(OR^{h22})(OR^{i22})$, $P(O)(OR^{h22})(OR^{i22})$, and $BR^{j22}R^{k22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, or 4 independently selected $R^{2c}$ substituents;

each $R^{a22}$, $R^{b22}$, $R^{c22}$ and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{b22}$, $R^{c22}$ and $R^{d22}$ are each optionally substituted with 1, 2, 3, or 4 independently selected $R^{2c}$ substituents;

or, any $R^{c22}$ and $R^{d22}$, attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{2c}$ substituents;

each $R^{e22}$ is independently selected from H, OH, CN, $C_{1-6}$ alkyl, $C_{1-6}$ alkoxy, $C_{1-6}$ haloalkyl, $C_{1-6}$ haloalkoxy, $C_{2-10}$ alkenyl, and $C_{2-6}$ alkynyl;

each $R^{f22}$ and $R^{g22}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h22}$ and $R^{i22}$ is independently selected from H, $C_{1-6}$ alkyl, $C_{1-6}$ haloalkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j22}$ and $R^{k22}$ is independently selected from OH, $C_{1-6}$ alkoxy, and $C_{1-6}$ haloalkoxy;

or any $R^{j22}$ and $R^{k22}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2c}$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a23}$, $SR^{a23}$, $NHOR^{a23}$, $C(O)OR^{b23}$, $C(O)NR^{c23}R^{d23}$, $C(O)NR^{c23}(OR^{a23})$, $C(O)OR^{a23}$, $OC(O)R^{b23}$, $OC(O)NR^{c23}R^{d23}$, $NR^{c23}R^{d23}$, $NR^{c23}NR^{c23}R^{d23}$, $NR^{c23}C(O)R^{b23}$, $NR^{c23}C(O)OR^{a23}NR^{c23}C(O)NR^{c23}R^{d23}$, $C(=NR^{e23})R^{b23}$, $C(=NR^{e23})NR^{c23}R^{d23}NR^{c23}C(=NR^{e23})NR^{c23}R^{d23}$, $NR^{c23}C(=NR^{e23})R^{b23}$, $NR^{c23}S(O)NR^{c23}R^{d23}$, $NR^{c23}S(O)R^{b23}$, $NR^{c23}S(O)_2R^{b23}$, $NR^{c23}S(O)(=NR^{e23})R^{b23}$, $NR^{c23}S(O)_2NR^{c23}R^{d23}$, $S(O)R^{b23}$, $S(O)NR^{c23}R^{d23}$, $S(O)_2R^{b23}$, $S(O)_2NR^{c23}R^{d23}$, $OS(O)(=NR^{e23})R^{b23}$, $OS(O)_2R^{b23}$, $S_{F5}$, $P(O)R^{f23}R^{g23}$, $OP(O)(OR^{h23})(OR^{i23})$, $P(O)(OR^{h23})(OR^{i23})$, and $BR^{j23}R^{k23}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2c}$ are each optionally substituted with 1, 2, 3, or 4 independently selected $R^{2D}$ substituents;

each $R^{a23}$, $R^{b23}$, $R^{c23}$ and $R_{d23}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a23}R^{b23}$, $R^{c23}$ and $R^{d23}$ are each optionally substituted with 1, 2, 3, or 4 independently selected $R^{2D}$ substituents;

or, any $R^{c23}$ and $R^{d23}$, attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{2D}$ substituents;

each $R^{e23}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f23}$ and $R^{g23}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{b23}$ and $R^{i23}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j23}$ and $R^{k23}$ is independently selected from OH, $C_{1-6}$ alkoxy, and $C_{1-6}$ haloalkoxy;

or any $R^{j23}$ and $R^{k23}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2D}$ is independently selected from D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl, CN, $NO_2$, $OR^{a24}$, $SR^{a24}$, $NHOR^{a24}$, $C(O)R^{b24}$, $C(O)NR^{c24}R^{d24}$, $C(O)NR^{c24}(OR^{a24})$, $C(O)OR^{a24}$, $OC(O)R^{b24}$, $OC(O)NR^{c24}R^{d24}$, $NR^{c24}R^{d24}$, $NR^{c24}NR^{c24}R^{d24}$, $NR^{c24}C(O)R^{b24}$, $NR^{c24}C(O)OR^{a24}$, $NR^{c24}C(O)NR^{c24}R^{d24}$, $C(=NR^{e23})R^{b24}$, $C(=NR^{e24})NR^{c24}R^{d24}$, $NR^{c24}C(=NR^{e24})NR^{c24}R^{d24}$, $NR^{c24}C(=NR^{e24})R^{b24}$, $NR^{c24}S(O)NR^{c24}R^{d24}$, $NR^{c24}S(O)R^{b24}$, $NR^{c24}S(O)_2R^{b24}$, $NR^{c24}S(O)(=NR^{e24})R^{b24}$, $NR^{c24}S(O)_2NR^{c24}R^{d24}$, $S(O)R^{b24}$, $S(O)NR^{c24}R^{d24}$, $S(O)_2R^{b24}$, $S(O)_2NR^{c24}R^{d24}$, $OS(O)(=NR^{e24})R^{b24}$, $OS(O)_2R^{b24}$, $SF_5$, $P(O)R^{f24}R^{g24}$, $OP(O)(OR^{h24})(OR^{i24})$, $P(O)(OR^{h24})(OR^{i24})$, and $BR^{j24}R^{k24}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{2D}$ are each optionally substituted with 1, 2, 3, or 4 independently selected $R^{2E}$ substituents;

each $R^{a24}$, $R^{b24}$, $R^{c24}$ and $R^{d24}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a24}$, $R^{b24}$, $R^{c24}$ and $R^{d24}$ are each optionally substituted with 1, 2, 3, or 4 independently selected $R^{2E}$ substituents;

or, any $R^{c24}$ and $R^{d24}$, attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{2E}$ substituents;

each $R^{e24}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f24}$ and $R^{g24}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h24}$ and $R^{k24}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j24}$ and $R^{k24}$ is independently selected from OH, $C_{1-6}$ alkoxy, and $C_{1-6}$ haloalkoxy;

or any $R^{j24}$ and $R^{k24}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2E}$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO-$C_{1-3}$ alkyl, $C_{1-3}$ alkoxy-$C_{1-3}$ alkyl, C3-5 cycloalkyl, $C_{1-3}$ alkoxy, $C_{1-3}$ haloalkoxy, amino, $C_{1-3}$ alkylamino, alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, amino sulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^3$ is selected from H, D, halo, OH, CN, $NO_2$, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-3}$ alkyl, HO-$C_{1-3}$ alkyl, $C_{1-3}$ alkoxy-$C_{1-3}$ alkyl, $C_{3-5}$ cycloalkyl, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{2-6}$ alkylaminocarbonylamino, and di($C_{1-3}$ alkyl)aminocarbonylamino;

$R^4$ is selected from H, D, halo, OH, CN, $NO_2$, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, cyano-$C_{1-3}$ alkyl, HO-$C_{1-3}$ alkyl, $C_{1-3}$ alkoxy-$C_{1-3}$ alkyl, $C_{3-5}$ cycloalkyl, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each $R^5$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{d5}R^{d5}$, $NR^{c5}C(O)R^{b5}NR^{c5}C(O)$ $NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)NR^{c5}R^{d5}$, $NR^{c5}S(O)R^{b5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, 4, 5, or 6 independently selected $R^{5A}$ substituents;

each $R^{a5}$, $R^{b5}$, $R^{c5}$ and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{b5}$, $R^{c5}$ and $R^{d5}$ are each optionally substituted with 1, 2, 3, 4, 5, or 6 independently selected $R^{5A}$ substituents;

or, any $R^{c5}$ and $R^{d5}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{5A}$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f5}$ and $R^{g5}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5A}$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{3-6}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, C1-6 alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, C1-6 alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^6$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}CO)R^{b6}$, $NR^{c6}C(O)OR^{a6}$, $NR^{c6}C(O)NR^{c6}R^{d6}C(=NR^{e6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)NR^{c6}R^{d6}$, $NR^{c6}S(O)R^{b6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, $OS(O)_2R^{b6}$, $SF_6$, $P(O)R^{f6}R^{g6}$, $OP(O)(OR^{h6})(OR^{i6})$ $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, or 6 independently selected $R^{6A}$ substituents, or, two $R^6$ groups together form an oxo group;

each $R^{a6}$, $R^{b6}$, $R^{c6}$ and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- $R^{a6}$, $R^{b6}$, $R^{c6}$ and $R^{d6}$ are each optionally substituted with 1, 2, 3, 4, 5, or 6 independently selected $R^{6A}$ substituents;

or, any $R^{c6}$ and $R^{d6}$, attached to the same N atom, together with the N atom to which they are attached, form a 4-10 membered heterocycloalkyl group, wherein the 4-10 membered heterocycloalkyl group is optionally substituted with 1, 2, 3, 4, 5, or 6 independently selected $R^{6A}$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^{6A}$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{3-6}$ cycloalkyl, $C_{1-6}$ alkoxy, $C_{1-6}$ haloalkoxy, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The compound of claim 1, or a pharmaceutically acceptable salt thereof, wherein $X^3$ is N and $X^4$ is N.

3. The compound of claim 1, or a pharmaceutically acceptable salt thereof, wherein $X^3$ is $CR^3$ and $X^4$ is N.

4. The compound of claim 1, or a pharmaceutically acceptable salt thereof, wherein $X^3$ is N and $X^4$ is $CR^4$.

5. The compound of claim 1, or a pharmaceutically acceptable salt thereof, wherein $R^3$ is selected from H and $C_{1-6}$ alkyl.

6. The compound of claim 1, or a pharmaceutically acceptable salt thereof, wherein $R^4$ is selected from H and $C_{1-6}$ alkyl.

7. The compound of claim 1, or a pharmaceutically acceptable salt thereof, wherein $Cy^1$ is $C_{1-6}$ aryl or 5-10 membered heteroaryl, wherein the $C_{6-10}$ aryl and 5-10 membered heteroaryl are each optionally substituted with 1, 2, 3, or 4 independently selected $R^5$ substituents.

8. The compound of claim 1, or a pharmaceutically acceptable salt thereof, wherein $Cy^1$ is phenyl optionally substituted with 1, 2, 3, or 4 independently selected $R^5$ substituents; and each $R^5$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$NHOR$^{a5}$, C(O)R$^{b5}$, C(O)NR$^{c5}$R$^{d5}$, C(O)NR$^{c5}$(OR$^{a5}$), C(O)OR$^{a5}$, OC(O)R$^{b5}$, OC(O)NR$^{c5}$R$^{d5}$, NR$^{c5}$R$^{d5}$, NR$^{c5}$NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$C(=NR$^{e5}$)R$^{b5}$, NR$^{c5}$S(O)NR$^{c5}$R$^{d5}$, NR$^{c5}$S(O)R$^{b5}$, NR$^{c5}$S(O)$_2$R$^{b5}$, NR$^{c5}$S(O)(=NR$^{e5}$)R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, S(O)$_2$NR$^{c5}$R$^{d5}$, OS(O)(=NR$^{e5}$)R$^{b5}$, and OS(O)$_2$R$^{b5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents.

9. The compound of claim 1, or a pharmaceutically acceptable salt thereof, wherein $Cy^1$ is phenyl optionally substituted with 1 or 2 independently selected $R^5$ substituents; and each $R^5$ is independently selected from halo, $C_{1-6}$ alkyl, $C_{1-6}$ haloalkyl, CN, and $NO_2$.

10. The compound of claim 1, or a pharmaceutically acceptable salt thereof, wherein $Cy^1$ is cyanophenyl optionally substituted with fluoro.

11. The compound of claim 1, or a pharmaceutically acceptable salt thereof, wherein $Cy^2$ is 5-10 membered heteroaryl or 4-10 membered heterocycloalkyl, wherein the 5-10 membered heteroaryl and 4-10 membered heterocycloalkyl are each optionally substituted with 1, 2, 3, or 4 independently selected $R^6$ substituents.

12. The compound of claim 1, or a pharmaceutically acceptable salt thereof, wherein $Cy^2$ is 5-10 membered heteroaryl or 4-10 membered heterocycloalkyl, wherein the 5-10 membered heteroaryl and 4-10 membered heterocycloalkyl are each optionally substituted with 1, 2, 3, or 4 independently selected $R^6$ substituents; and each $R^6$ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, C(O)R$^{b6}$, C(O)NR$^{c6}$R$^{d6}$, C(O)NR$^{c6}$(OR$^{a6}$), C(O)OR$^{a6}$, OC(O)R$^{b6}$, OC(O)NR$^{c6}$R$^{d6}$, NR$^{c6}$R$^{d6}$, NR$^{c6}$NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, C(=NR$^{e6}$)R$^{b6}$, C(=NR$^{e6}$)NR$^{c6}$R$^{d6}$, NR$^{c6}$C(=NR$^{e6}$)NR$^{c6}$R$^{d6}$, NR$^{c6}$C(=NR$^{e6}$)R$^{b6}$, NR$^{c6}$S(O)NR$^{c6}$R$^{d6}$, NR$^{c6}$S(O)R$^{b6}$, NR$^{c6}$S(O)$_2$R$^{b6}$, NR$^{c6}$S(O)(=NR$^{e6}$)R$^{b6}$, NR$^{c6}$S(O)$_2$NR$^{c6}$R$^{d6}$, S(O)R$^{b6}$, S(O)NR$^{c6}$R$^{d6}$, S(O)$^2$R$^{b6}$, S(O)$_2$NR$^{c6}$R$^{d6}$, OS(O)(=NR$^{e6}$)R$^{b6}$, and OS(O)$_2$R$^{b6}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^6$ are each optionally substituted with 1, 2, 3, or 4 independently selected R$^{6A}$ substituents, or, two R$^6$ groups together form an oxo group.

13. The compound of claim 1, or a pharmaceutically acceptable salt thereof, wherein Cy$^2$ is 5-10 membered heteroaryl or 4-10 membered heterocycloalkyl, wherein the 5-10 membered heteroaryl and 4-10 membered heterocycloalkyl are each optionally substituted with 1, 2, or 3 independently selected R$^6$ substituents; and each R$^6$ is independently selected from halo, C$_{1-6}$ alkyl, and C$_{1-6}$ haloalkyl, wherein the C$_{1-6}$ alkyl is optionally substituted with OH or, two R$^6$ groups together form an oxo group.

14. The compound of claim 1, or a pharmaceutically acceptable salt thereof, wherein Cy$^2$ is selected from pyrimidin-4-yl, 1-ethyl-1H-pyrazol-5-yl, pyridin-4-yl, 1-isopropyl-1H-pyrazol-5-yl, 1-methyl-1H-pyrazol-5-yl, 1-methyl-6-oxo-1,6-dihydropyridin-3-yl, 3-methylpyridin-4-yl, 4-(hydroxymethyl)-2-methyloxazol-5-yl, 4-methyloxazol-5-yl, oxazol-5-yl, quinolin-6-yl, and quinoxalin-6-yl.

15. The compound of claim 1, or a pharmaceutically acceptable salt thereof, wherein R$^1$ is selected from H, C$_{1-6}$ alkyl, C$_{2-6}$ alkenyl, C$_{2-6}$ alkynyl, and C$_{1-6}$ haloalkyl.

16. The compound of claim 1, or a pharmaceutically acceptable salt thereof, wherein R$^1$ is H.

17. The compound of claim 1, or a pharmaceutically acceptable salt thereof, wherein R$^2$ is selected from H, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- are each optionally substituted with 1, 2, 3, or 4 independently selected R$^{2A}$ substituents.

18. The compound of claim 1, or a pharmaceutically acceptable salt thereof, wherein R$^2$ is selected from C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- are each optionally substituted with 1, 2, 3, or 4 independently selected R$^{2A}$ substituents; and each R$^{2A}$ is independently selected from D, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a21}$, SR$^{a21}$, NHOR$^{a21}$, C(O)R$^{b21}$, C(O)NR$^{c21}$R$^{d21}$, C(O)NR$^{c21}$(OR$^{a21}$), C(O)OR$^{a21}$, OC(O)R$^{b21}$, OC(O)NR$^{c21}$R$^{d21}$, NR$^{c21}$R$^{d21}$, S(O)R$^{b21}$, S(O)NR$^{c21}$R$^{d21}$, and S(O)$_2$R$^{b21}$.

19. The compound of claim 1, or a pharmaceutically acceptable salt thereof, wherein R$^2$ is phenyl-C$_{1-3}$ alkyl- or (5-10 membered heteroaryl)-C$_{1-3}$ alkyl-, wherein the phenyl-C$_{1-3}$ alkyl- and (5-10 membered heteroaryl)-C$_{1-3}$ alkyl- are each optionally substituted with 1, 2, 3, or 4 independently selected R$^{2A}$ substituents; and each R$^{2A}$ is independently selected from halo, C$_{1-6}$ alkyl, and C$_{1-6}$ haloalkyl.

20. The compound of claim 1, or a pharmaceutically acceptable salt thereof, wherein R$^2$ is selected from pyridin-2-ylmethyl, (1-methyl-1H-pyrazol-3-yl)methyl, (3-fluoropyridin-2-yl)methyl, (6-methylpyridin-2-yl)methyl, 1-(pyridin-2-yl)ethyl, 2-(pyridin-2-yl)ethyl, and 2-fluorobenzyl.

21. The compound of claim 1, which is a compound of Formula (II):

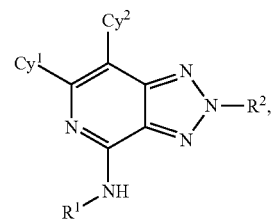

(II)

or a pharmaceutically acceptable salt thereof.

22. The compound of claim 1, which is a compound of Formula (IIa):

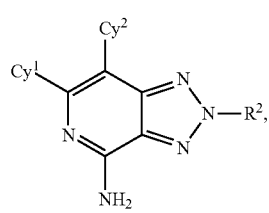

(IIa)

or a pharmaceutically acceptable salt thereof.

23. The compound of claim 1, which is a compound of Formula (IIb):

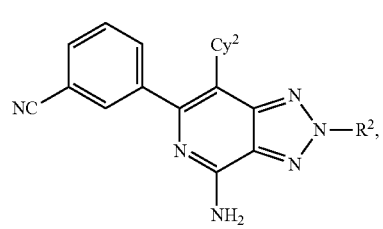

(IIb)

or a pharmaceutically acceptable salt thereof.

24. The compound of claim 1, which is a compound of Formula (III):

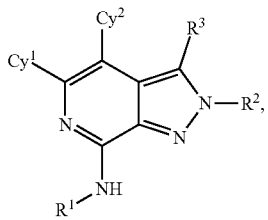

(III)

or a pharmaceutically acceptable salt thereof.

25. The compound of claim 1, which is a compound of Formula (IIIa):

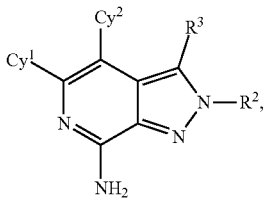

(IIIa)

or a pharmaceutically acceptable salt thereof.

26. The compound of claim 1, which is a compound of Formula (IIIb):

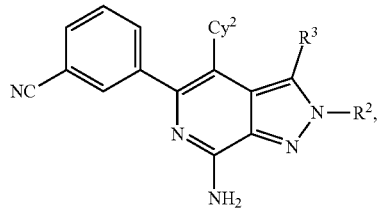

(IIIb)

or a pharmaceutically acceptable salt thereof.

27. The compound of claim 1, which is a compound of Formula (IV):

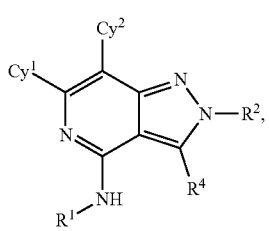

(IV)

or a pharmaceutically acceptable salt thereof.

28. The compound of claim 1, which is a compound of Formula (IVa):

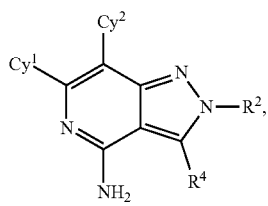

(IVa)

or a pharmaceutically acceptable salt thereof.

29. The compound of claim 1, which is a compound of Formula (IVb):

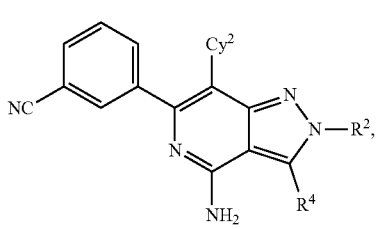

(IVb)

or a pharmaceutically acceptable salt thereof.

30. The compound of claim 1, which is a compound of Formula (V):

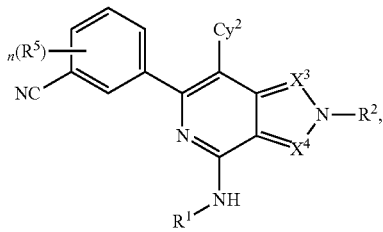

(V)

or a pharmaceutically acceptable salt thereof,
wherein n is 0, 1, or 2.

31. The compound of claim 1, or a pharmaceutically acceptable salt thereof, wherein
    $X^3$ is N or $CR^3$;
    $X^4$ is N or $CR^4$;
    wherein at least one of $X^3$ and $X^4$ is N;
    $Cy^1$ is $C_{6-10}$ aryl optionally substituted with 1, 2, 3, or 4 independently selected $R^5$ substituents;
    $Cy^2$ is selected from 5-10 membered heteroaryl and 4-10 membered heterocycloalkyl, wherein the 5-10 membered heteroaryl and 4-10 membered heterocycloalkyl of $Cy^2$ are each optionally substituted with 1, 2, 3, or 4 independently selected $R^6$ substituents;
    $R^1$ is selected from H and $C_{1-6}$ alkyl;
    $R^2$ is selected from $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R² are each optionally substituted with 1, 2, 3, or 4 independently selected R²ᴬ substituents;

each R²ᴬ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, and OR$^{a21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R²ᴬ are each optionally substituted with 1, 2, 3, or 4 independently selected R²ᴮ substituents;

R$^{a21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl;

each R²ᴮ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, and OR$^{a22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R²ᴮ are each optionally substituted with 1, 2, 3, or 4 independently selected R²ᶜ substituents;

R$^{a22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl;

each R²ᶜ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, and OR$^{a23}$ R$^{a23}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl;

R³ is selected from H and $C_{1-6}$ alkyl;

R⁴ is selected from H and $C_{1-6}$ alkyl;

each R⁵ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO₂, OR$^{a5}$, and NR$^{c5}$R$^{d5}$;

each R$^{a5}$, R$^{c5}$ and R$^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

or, any R$^{c5}$ and R$^{d5}$, attached to the same N atom, together with the N atom to which they are attached, form a 4-10 membered heterocycloalkyl group;

each R⁶ is independently selected from D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO₂, OR$^{a6}$, and NR$^{c6}$R$^{d6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R⁶ are each optionally substituted with 1, 2, 3, or 4 independently selected R$^{6A}$ substituents, or, two R⁶ groups together form an oxo group;

each R$^{a6}$, R$^{c6}$ and R$^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

or, any R$^{c6}$ and R$^{d6}$, attached to the same N atom, together with the N atom to which they are attached, form a 4-10 membered heterocycloalkyl group; and each R$^{6A}$ is independently selected from OH, NO₂, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO-$C_{1-6}$ alkyl, $C_{1-6}$ alkoxy-$C_{1-6}$ alkyl, $C_{1-6}$ cycloalkyl, $C_{1-6}$ alkoxy, $C_{1-6}$ haloalkoxy, amino, and $C_{1-6}$ alkylamino.

32. The compound of claim 1, selected from:

3-(4-amino-2-(pyridin-2-ylmethyl)-7-(pyrimidin-4-yl)-2H-pyrazolo[4,3-c]pyridin-6-yl)benzonitrile;

3-(4-amino-7-(1-ethyl-1H-pyrazol-5-yl)-2-(pyridin-2-ylmethyl)-2H-pyrazolo[4,3-c]pyridin-6-yl)benzonitrile;

3-(4-amino-2-((3-fluoropyridin-2-yl)methyl)-7-(pyrimidin-4-yl)-2H-pyrazolo[4,3-c]pyridin-6-yl)benzonitrile;

3-(4-amino-2-((1-methyl-1H-pyrazol-3-yl)methyl)-7-(pyrimidin-4-yl)-2H-pyrazolo[4,3-c]pyridin-6-yl)benzonitrile;

3-(4-amino-2-((6-methylpyridin-2-yl)methyl)-7-(pyrimidin-4-yl)-2H-pyrazolo[4,3-c]pyridin-6-yl)benzonitrile;

3-(4-amino-2-(pyridin-2-ylmethyl)-7-(pyridin-4-yl)-2H-pyrazolo[4,3-c]pyridin-6-yl)benzonitrile;

3-(4-amino-2-(2-fluorobenzyl)-7-(pyrimidin-4-yl)-2H-pyrazolo[4,3-c]pyridin-6-yl)benzonitrile;

3-(7-amino-2-(pyridin-2-ylmethyl)-4-(pyrimidin-4-yl)-2H-pyrazolo[3,4-c]pyridin-5-yl)benzonitrile;

3-(7-amino-4-(1-ethyl-1H-pyrazol-5-yl)-2-(pyridin-2-ylmethyl)-2H-pyrazolo[3,4-c]pyridin-5-yl)benzonitrile;

3-(7-amino-2-((6-methylpyridin-2-yl)methyl)-4-(pyrimidin-4-yl)-2H-pyrazolo[3,4-c]pyridin-5-yl)benzonitrile;

3-(7-amino-4-(1-ethyl-1H-pyrazol-5-yl)-2-((6-methylpyridin-2-yl)methyl)-2H-pyrazolo[3,4-c]pyridin-5-yl)benzonitrile;

3-(7-amino-4-(4-methyloxazol-5-yl)-2-(pyridin-2-ylmethyl)-2H-pyrazolo[3,4-c]pyridin-5-yl)benzonitrile;

3-(7-amino-4-(4-methyloxazol-5-yl)-2-((6-methylpyridin-2-yl)methyl)-2H-pyrazolo[3,4-c]pyridin-5-yl)benzonitrile;

3-(7-amino-4-(1-ethyl-1 H-pyrazol-5-yl)-2-((3-fluoropyridin-2-yl)methyl)-2H-pyrazolo[3,4-c]pyridin-5-yl)benzonitrile;

3-(7-amino-2-((3-fluoropyridin-2-yl)methyl)-4-(pyrimidin-4-yl)-2H-pyrazolo [3,4-c]pyridin-5-yl)benzonitrile;

3-(4-amino-2-(pyridin-2-ylmethyl)-7-(pyrimidin-4-yl)-2H-[1,2,3]triazolo [4,5-c]pyridin-6-yl)benzonitrile;

3-(4-amino-7-(4-methyloxazol-5-yl)-2-(pyridin-2-ylmethyl)-2H-[1,2,3]triazolo [4,5-c]pyridin-6-yl)benzonitrile;

3-(4-amino-7-(1-ethyl-1 H-pyrazol-5-yl)-2-(pyridin-2-ylmethyl)-2H- [1,2,3]triazolo [4,5-c]pyridin-6-yl)benzonitrile;

3-(4-amino-7-(3-methylpyridin-4-yl)-2-(pyridin-2-ylmethyl)-2H-[1,2,3]triazolo [4,5-c]pyridin-6-yl)benzonitrile;

3-(4-amino-7-(4-(hydroxymethyl)-2-methyloxazol-5-yl)-2-(pyridin-2-ylmethyl)-2H-[1,2,3]triazolo [4,5-c]pyridin-6-yl)benzonitrile;

3-(4-amino-7-(oxazol-5-yl)-2-(pyridin-2-ylmethyl)-2H-[1,2,3]triazolo [4,5-c]pyridin-6-yl)benzonitrile;

3-(4-amino-2-(pyridin-2-ylmethyl)-7-(quinolin-6-yl)-2H-[1,2,3]triazolo [4,5-c]pyridin-6-yl)benzonitrile;

3-(4-amino-2-(pyridin-2-ylmethyl)-7-(quinoxalin-6-yl)-2H-[1,2,3]triazolo [4,5-c]pyridin-6-yl)benzonitrile;

3-(4-amino-2-((6-methylpyridin-2-yl)methyl)-7-(pyrimidin-4-yl)-2H-[1,2,3]triazolo [4,5-c]pyridin-6-yl)benzonitrile;

3-(4-amino-2-((6-methylpyridin-2-yl)methyl)-7-(pyridin-4-yl)-2H-[1,2,3]triazolo [4,5-c]pyridin-6-yl)benzonitrile;

3-(4-amino-2-((6-methylpyridin-2-yl)methyl)-7-(3-methylpyridin-4-yl)-2H-[1,2,3]triazolo [4,5-c]pyridin-6-yl)benzonitrile;

3-(4-amino-7-(1-methyl-6-oxo-1, 6-dihydropyridin-3-yl)-24(6-methylpyridin-2-yl)methyl)-2H41,2,3]triazolo [4,5-c]pyridin-6-yl)benzonitrile;

3-(4-amino-7-(1-ethyl-1 H-pyrazol-5-yl)-24(6-methylpyridin-2-yl)methyl)-2H-[1,2,3]triazolo [4,5-c]pyridin-6-yl)benzonitrile;

3-(4-amino-7-(4-methyloxazol-5-yl)-24(6-methylpyridin-2-yl)methyl)-2H-[1,2,3]triazolo [4,5-c]pyridin-6-yl)benzonitrile;

3-(4-amino-2-((3-fluoropyridin-2-yl)methyl)-7-(pyrimidin-4-yl)-2H-[1,2,3]triazolo [4,5-c]pyridin-6-yl)benzonitrile;

3-(4-amino-2-((3-fluoropyridin-2-yl)methyl)-7-(pyridin-4-yl)-2H-[1,2,3]triazolo [4,5-c]pyridin-6-yl)benzonitrile;

3-(4-amino-2-((3-fluoropyridin-2-yl)methyl)-7-(1-methyl-6-oxo-1,6-dihydropyridin-3-yl)-2H- [1,2,3]triazolo [4,5-c]pyridin-6-yl)benzonitrile;

3-(4-amino-7-(1-ethyl-1 H-pyrazol-5-yl)-24(3-fluoropyridin-2-yl)methyl)-2H-[1,2,3]triazolo [4,5-c]pyridin-6-yl)benzonitrile;

3-(4-amino-2-((3-fluoropyridin-2-yl)methyl)-7-(1-isopropyl-1H-pyrazol-5-yl)-2H-[1,2,3]triazolo [4,5-c]pyridin-6-yl)benzonitrile;

3-(4-amino-2-((3-fluoropyridin-2-yl)methyl)-7-(1-methyl-1H-pyrazol-5-yl)-2H-[1,2,3]triazolo [4,5-c]pyridin-6-yl)benzonitrile;

3-(4-amino-2-((3-fluoropyridin-2-yl)methyl)-7-(4-methyloxazol-5-yl)-2H-[1,2,3]triazolo [4,5-c]pyridin-6-yl)benzonitrile;

3-(4-amino-2-((3-fluoropyridin-2-yl)methyl)-7-(quinoxalin-6-yl)-2H-[1,2,3]triazolo [4,5-c]pyridin-6-yl)benzonitrile;

3-(4-amino-7-(1-ethyl-1 H-pyrazol-5-yl)-2-(pyridin-2-ylmethyl)-2H- [1,2,3]triazolo [4,5-c]pyridin-6-yl)-2-fluorobenzonitrile;

3-(4-amino-7-(1-methyl-1 H-pyrazol-5-yl)-2-(pyridin-2-ylmethyl)-2H-[1,2,3]triazolo [4,5-c]pyridin-6-yl)-2-fluorobenzonitrile;

3-(4-amino-7-(1-isopropyl-1H-pyrazol-5-yl)-2-(pyridin-2-ylmethyl)-2H-[1,2,3]triazolo [4,5-c]pyridin-6-yl)-2-fluorobenzonitrile;

3-(4-amino-7-(4-methyloxazol-5-yl)-2-(pyridin-2-ylmethyl)-2H-[1,2,3]triazolo [4,5-c]pyridin-6-yl)-2-fluorobenzonitrile;

3-(4-amino-7-(4-(hydroxymethyl)-2-methyloxazol-5-yl)-2-(pyridin-2-ylmethyl)-2H-[1,2,3]triazolo [4,5-c]pyridin-6-yl)-2-fluorobenzonitrile;

3-(4-amino-2-(pyridin-2-ylmethyl)-7-(quinoxalin-6-yl)-2H-[1,2,3]triazolo [4,5-c]pyridin-6-yl)-2-fluorobenzonitrile;

3-(4-amino-2-((1-methyl-1H-pyrazol-3-yl)methyl)-7-(pyrimidin-4-yl)-2H-[1,2,3]triazolo [4,5-c]pyridin-6-yl)benzonitrile;

3-(4-amino-2-((1-methyl-1H-pyrazol-3-yl)methyl)-7-(4-methyloxazol-5-yl)-2H-[1,2,3]triazolo [4,5-c]pyridin-6-yl)benzonitrile;

3-(4-amino-7-(4-methyloxazol-5-yl)-2-(1-(pyridin-2-yl)ethyl)-2H-[1,2,3]triazolo [4,5-c]pyridin-6-yl)benzonitrile;

3-(4- amino-2-(1-(pyridin-2-yl) ethyl)-7-(pyrimidin-4-yl)-2H41,2,3]triazolo [4,5-c]pyridin-6-yl)benzonitrile;

3-(4- amino-7-(4-methyloxazol-5-yl)-2-(2-(pyridin-2-yl) ethyl)-2H- [1,2,3]triazolo [4,5-c]pyridin-6-yl)benzonitrile; and 3-(4- amino-7-(4-methyloxazol-5-yl)-2-(2-(pyridin-2-yl) ethyl)-2H- [1,2,3]triazolo [4,5-c]pyridin-6-yl)-2-fluorobenzonitrile, or a pharmaceutically acceptable salt thereof.

33. A pharmaceutical composition comprising a compound of claim 1, or a pharmaceutically acceptable salt thereof, and a pharmaceutically acceptable excipient or carrier.

34. A method of inhibiting an activity of an adenosine receptor, comprising contacting the receptor with a compound of claim 1 or a pharmaceutically acceptable salt thereof.

35. A method of treating a disease or disorder selected from head and neck squamous cell carcinoma, non-small cell lung cancer (NSCLC), ovarian cancer, prostate cancer, breast cancer, and bladder cancer in a patient comprising administering to said patient a therapeutically effective amount of a compound of claim 1, or a pharmaceutically acceptable salt thereof.

36. The method of claim 35, wherein the disease or disorder is head and neck squamous cell carcinoma.

37. The method of claim 35, wherein the disease or disorder is non-small cell lung cancer (NSCLC).

38. The method of claim 35, wherein the disease or disorder is ovarian cancer.

39. The method of claim 35, wherein the disease or disorder is prostate cancer.

40. The method of claim 35, wherein the disease or disorder is breast cancer.

41. The method of claim 35, wherein the disease or disorder is bladder cancer.

42. The compound of claim 1, which is 3-(4-amino-2-((3-fluoropyridin-2-yl)methyl)-7-(pyrimidin-4-yl)-2H-[1,2,3]triazolo[4,5-c]pyridin-6-yl)benzonitrile, or a pharmaceutically acceptable salt thereof.

* * * * *

UNITED STATES PATENT AND TRADEMARK OFFICE
CERTIFICATE OF CORRECTION

PATENT NO. : 11,390,624 B2
APPLICATION NO. : 16/774086
DATED : July 19, 2022
INVENTOR(S) : Taisheng Huang and Xiaozhao Wang It is certified that error appears in the above-identified patent and that said Letters Patent is hereby corrected as shown below:

In the Claims

Column 103, Line 25, Claim 1, delete "$C_{3\text{-}10}$" and insert -- $C_{3\text{-}10}$ --;

Column 103, Line 28, Claim 1, delete "$C_{1\text{-}6}$alkyl-," and insert -- $C_{1\text{-}6}$ alkyl-, --;

Column 103, Line 29, Claim 1, delete "heterocycloalkly)-$C_{1\text{-}6}$alkyl-," and insert -- heterocycloalkyl)-$C_{1\text{-}6}$ alkyl-, --;

Column 103, Line 32, Claim 1, delete "$C_{1\text{-}6}$alkyl, $C_{2\text{-}6}$alkenyl," and insert -- $C_{1\text{-}6}$ alkyl, $C_{2\text{-}6}$ alkenyl, --;

Column 103, Line 33, Claim 1, delete "$C_{3\text{-}10}$cycloalkyl," and insert -- $C_{3\text{-}10}$ cycloalkyl, --;

Column 103, Line 36, Claim 1, delete "$C_{1\text{-}6}$alkyl-," and insert -- $C_{1\text{-}6}$ alkyl-, --;

Column 103, Line 45, Claim 1, delete "$C_{1\text{-}6}$, alkyl-," and insert -- $C_{1\text{-}6}$ alkyl-, --;

Column 103, Line 52, Claim 1, delete "$R^{d2}$" and insert -- $R^{d2}$, --;

Column 104, Line 12, Claim 1, delete "$S(O)NR^{c21}, R^{d21}$," and insert -- $S(O)NR^{c21}R^{d21}$, --;

Column 104, Line 13, Claim 1, delete "$(S)(O)(=NR^{e21})R^{b21}$," and insert -- $OS(O)(=NR^{e21})R^{b21}$, --;

Column 104, Line 24, Claim 1, delete "Each" and insert -- each --;

Column 105, Line 11, Claim 1, delete "$C(O)R^{b22} C(O)NR^{c22}R_{d22}$," and insert -- $C(O)R^{b22}$, $C(O)NR^{c22}R^{d22}$, --;

Column 105, Line 20, Claim 1, delete "$S(O)_2NR^{c22}R^{b22}$," and insert -- $S(O)_2NR^{c22}R^{d22}$, --;

Signed and Sealed this
Twenty-sixth Day of September, 2023

Katherine Kelly Vidal
*Director of the United States Patent and Trademark Office*

Column 105, Line 30, Claim 1, delete "$R^{2c}$" and insert -- $R^{2C}$ --;

Column 105, Line 45, Claim 1, delete "$R^{2c}$" and insert -- $R^{2C}$ --;

Column 105, Line 51, Claim 1, delete "$R^{2c}$" and insert -- $R^{2C}$ --;

Column 105, Line 54, Claim 1, delete "$C_{2-10}$ alkenyl," and insert -- $C_{2-6}$ alkenyl, --;

Column 106, Line 11, Claim 1, delete "$R^{2c}$" and insert -- $R^{2C}$ --;

Column 106, Line 19, Claim 1, delete "$C(O)OR^{b23}$," and insert -- $C(O)R^{b23}$, --;

Column 106, Line 22, Claim 1, delete "$NR^{c23}C(O)OR^{a23}NR^{c23}C(O)$" and insert -- $NR^{c23}C(O)OR^{a23}$, $NR^{c23}C(O)$ --;

Column 106, Line 24, Claim 1, delete "$NR^{c23}R^{d23}NR^{c23}$" and insert -- $NR^{c23}R^{d23}$, $NR^{c23}$ --;

Column 106, Line 36, Claim 1, delete "$R^{2c}$" and insert -- $R^{2C}$ --;

Column 106, Line 39, Claim 1, delete "$R_{d23}$" and insert -- $R^{d23}$ --;

Column 106, Line 51, Claim 1, delete "$R^{a23}R^{b23}$," and insert -- $R^{a23}$, $R^{b23}$, --;

Column 107, Line 4, Claim 1, delete "$R^{b23}$" and insert -- $R^{h23}$ --;

Column 107, Line 30, Claim 1, delete "$C(=NR^{e23})R^{b24}$," and insert -- $C(=NR^{e24})R^{b24}$, --;

Column 108, Line 30, Claim 1, delete "C3-5" and insert -- $C_{3-5}$ --;

Column 108, Line 31, Claim 1, delete "alkyl)amino," and insert -- di($C_{1-3}$ alkyl)amino, --;

Column 108, Lines 33-34, Claim 1, delete "alkyl)carbamyl," and insert -- di($C_{1-3}$ alkyl)carbamyl, --;

Column 108, Line 40, Claim 1, delete "amino sulfonylamino," and insert -- aminosulfonylamino, --;

Column 108, Line 60, Claim 1, delete "$C_{2-6}$" and insert -- $C_{1-3}$ --;

Column 108, Line 65, Claim 1, delete "cyano-$C_{1-6}$" and insert -- cyano-$C_{1-3}$ --;

Column 109, Lines 23-24, Claim 1, delete "$NR^{c5}NR^{d5}R^{d5}$, $NR^{c5}C(O)R^{b5}NR^{c5}C(O)NR^{c5}R^{d5}$," and insert -- $NR^{c5}NR^{c5}R^{d5}$, $NR^{c5}C(O)R^{b5}$, $NR^{c5}(O)OR^{a5}$, $NR^{c5}C(O)NR^{c5}R^{d5}$, --;

Column 109, Line 31, Claim 1, delete "$BR^{-j5}R^{k5}$," and insert -- $BR^{j5}R^{k5}$, --;

Column 110, Line 24, Claim 1, delete "C1-6" and insert -- $C_{1-6}$ --;

CERTIFICATE OF CORRECTION (continued)
U.S. Pat. No. 11,390,624 B2

Column 110, Line 28, Claim 1, delete "C1-6" and insert -- $C_{1-6}$ --;

Column 110, Line 46, Claim 1, delete "$NR^{c6}CO)R^{b6}$," and insert -- $NR^{c6}C(O)R^{b6}$, --;

Column 110, Line 47, Claim 1, delete "$NR^{c6}C(O)NR^{c6}R^{d6}C$" and insert -- $NR^{c6}C(O)NR^{c6}R^{d6}$, C --;

Column 110, Line 53, Claim 1, delete "$(OR^{i6})$" and insert -- $(OR^{i6})$, --;

Column 111, Line 8, Claim 1, delete "$C_{1-6}$ alkyl-" and insert -- $C_{1-6}$ alkyl- of --;

Column 113, Line 5, Claim 12, delete "$NR^{c6}S(O)^2R^{b6}$," and insert -- $NR^{c6}S(O)_2R^{b6}$, --;

Column 113, Line 7, Claim 14, delete "$S(O)^2R^{b6}$," and insert -- $S(O)_2R^{b6}$ --;

Column 113, Line 30, Claim 14, delete "1- methyl-1H-pyrazol-5-yl," and insert -- 1-methyl-1H-pyrazol-5-yl, --;

Column 117, Line 36, Claim 31, delete "$R^{2c}$" and insert -- $R^{2C}$ --;

Column 117, Line 41, Claim 31, delete "$R^{2c}$" and insert -- $R^{2C}$ --;

Column 118, Line 33, Claim 31, delete "$C_{1-6}$ cycloalkyl," and insert -- $C_{3-6}$ cycloalkyl, --;

Column 118, Line 65, Claim 32, delete "1 H" and insert -- 1H --;

Column 119, Line 2, Claim 32, delete "pyrazolo [3,4-c]" and insert -- pyrazolo[3,4-c] --;

Column 119, Line 5, Claim 32, delete "triazolo [4,5-c]" and insert -- triazolo[4,5-c] --;

Column 119, Line 7, Claim 32, delete "triazolo [4,5-c]" and insert -- triazolo[4,5-c] --;

Column 119, Line 9, Claim 32, delete "1 H" and insert -- 1H --;

Column 119, Line 10, Claim 32, delete "2H- [1,2,3]triazolo [4,5-c]" and insert -- 2H-[1,2,3]triazolo[4,5-c] --;

Column 119, Line 13, Claim 32, delete "triazolo [4,5-c]" and insert -- triazolo[4,5-c] --;

Column 119, Line 16, Claim 32, delete "triazolo [4,5-c]" and insert -- triazolo[4,5-c] --;

Column 119, Line 20, Claim 32, delete "triazolo [4,5-c]" and insert -- triazolo[4,5-c] --;

Column 119, Line 22, Claim 32, delete "triazolo [4,5-c]" and insert -- triazolo[4,5-c] --;

Column 119, Line 24, Claim 32, delete "triazolo [4,5-c]" and insert -- triazolo[4,5-c] --;

CERTIFICATE OF CORRECTION (continued)
U.S. Pat. No. 11,390,624 B2

Column 119, Line 26, Claim 32, delete "triazolo [4,5-c]" and insert -- triazolo[4,5-c] --;

Column 119, Line 29, Claim 32, delete "triazolo [4,5-c]" and insert -- triazolo[4,5-c] --;

Column 119, Line 32, Claim 32, delete "triazolo [4,5-c]" and insert -- triazolo[4,5-c] --;

Column 119, Line 34, Claim 32, delete "1, 6" and insert -- 1,6 --;

Column 119, Line 35, Claim 32, delete "24(6-methylpyridin" and insert -- 2-((6-methylpyridin --;

Column 119, Line 35, Claim 32, delete "2H41,2,3]" and insert -- 2H-[1,2,3] --;

Column 119, Line 37, Claim 32, delete "1 H" and insert -- 1H --;

Column 119, Lines 37-38, Claim 32, delete "24(6-methylpyridin" and insert -- 2-((6-methylpyridin --;

Column 119, Line 38, Claim 32, delete "triazolo [4,5-c]" and insert -- triazolo[4,5-c] --;

Column 119, Lines 41-42, Claim 32, delete "24(6-methylpyridin" and insert -- 2-((6-methylpyridin --;

Column 119, Line 42, Claim 32, delete "triazolo [4,5-c]" and insert -- triazolo[4,5-c] --;

Column 119, Line 45, Claim 32, delete "triazolo [4,5-c]" and insert -- triazolo[4,5-c] --;

Column 119, Line 48, Claim 32, delete "triazolo [4,5-c]" and insert -- triazolo[4,5-c] --;

Column 119, Lines 51-52, Claim 32, delete "2H- [1,2,3]triazolo [4,5-c]" and insert
-- 2H-[1,2,3]triazolo[4,5-c] --;

Column 119, Line 53, Claim 32, delete "1 H" and insert -- 1H --;

Column 119, Lines 53-54, Claim 32, delete "24(3-fluoropyridin" and insert -- 2-((3-fluoropyridin --;

Column 119, Line 54, Claim 32, delete "triazolo [4,5-c]" and insert -- triazolo[4,5-c] --;

Column 119, Line 57, Claim 32, delete "triazolo [4,5-c]" and insert -- triazolo[4,5-c] --;

Column 119, Line 60, Claim 32, delete "triazolo [4,5-c]" and insert -- triazolo[4,5-c] --;

Column 119, Line 63, Claim 32, delete "triazolo [4,5-c]" and insert -- triazolo[4,5-c] --;

Column 119, Line 66, Claim 32, delete "triazolo [4,5-c]" and insert -- triazolo[4,5-c] --;

Column 120, Line 1, Claim 32, delete "1 H" and insert -- 1H --;

Column 120, Line 2, Claim 32, delete "2H- [1,2,3]triazolo [4,5-c]" and insert

-- 2H-[1,2,3]triazolo[4,5-c] --;

Column 120, Line 4, Claim 32, delete "1 H" and insert -- 1H --;

Column 120, Line 5, Claim 32, delete "triazolo [4,5-c]" and insert -- triazolo[4,5-c] --;

Column 120, Line 8, Claim 32, delete "triazolo [4,5-c]" and insert -- triazolo[4,5-c] --;

Column 120, Line 11, Claim 32, delete "triazolo [4,5-c]" and insert -- triazolo[4,5-c] --;

Column 120, Line 15, Claim 32, delete "triazolo [4,5-c]" and insert -- triazolo[4,5-c] --;

Column 120, Line 18, Claim 32, delete "triazolo [4,5-c]" and insert -- triazolo[4,5-c] --;

Column 120, Line 21, Claim 32, delete "triazolo [4,5-c]" and insert -- triazolo[4,5-c] --;

Column 120, Line 24, Claim 32, delete "triazolo [4,5-c]" and insert -- triazolo[4,5-c] --;

Column 120, Line 27, Claim 32, delete "triazolo [4,5-c]" and insert -- triazolo[4,5-c] --;

Column 120, Line 30, Claim 32, delete "3-(4- amino" and insert -- 3-(4-amino --;

Column 120, Line 30, Claim 32, delete "(pyridin-2-yl) ethyl)" and insert -- (pyridin-2-yl)ethyl) --;

Column 120, Line 31, Claim 32, delete "2H41,2,3]triazolo [4,5-c]" and insert -- 2H-[1,2,3]triazolo[4,5-c] --;

Column 120, Line 32, Claim 32, delete "3-(4- amino" and insert -- 3-(4-amino --;

Column 120, Line 33, Claim 32, delete "2H- [1,2,3]triazolo [4,5-c]" and insert -- 2H-[1,2,3]triazolo[4,5-c] --;

Column 120, Line 35, Claim 32, delete "3-(4- amino" and insert -- 3-(4-amino --;

Column 120, Line 36, Claim 32, delete "2H- [1,2,3]triazolo [4,5-c]" and insert -- 2H-[1,2,3]triazolo[4,5-c] --.